United States Patent
Cejas et al.

(10) Patent No.: US 12,252,678 B2
(45) Date of Patent: Mar. 18, 2025

(54) SYSTEMS AND METHODS FOR BIOPROCESSING

(71) Applicant: MicrofluidX Ltd, Stevenage (GB)

(72) Inventors: Cesare M. Cejas, Edgware (GB);
Antonio de Grazia, St. Albans (GB);
Manjari Ghanshyam, Hatfield (GB);
James Kusena, Hempstead (GB);
Sreedhar Mareddy, Chelmsford (GB)

(73) Assignee: MicrofluidX Ltd, Stevenage (GB)

( * ) Notice: Subject to any disclaimer, the term of this patent is extended or adjusted under 35 U.S.C. 154(b) by 0 days.

(21) Appl. No.: 17/953,016

(22) Filed: Sep. 26, 2022

(65) Prior Publication Data
US 2023/0167392 A1 Jun. 1, 2023

Related U.S. Application Data

(60) Provisional application No. 63/285,062, filed on Dec. 1, 2021.

(51) Int. Cl.
*B01L 3/00* (2006.01)
*C12M 1/00* (2006.01)
(Continued)

(52) U.S. Cl.
CPC ....... *C12M 23/16* (2013.01); *B01L 3/502715* (2013.01); *B01L 3/50273* (2013.01);
(Continued)

(58) Field of Classification Search
None
See application file for complete search history.

(56) References Cited

U.S. PATENT DOCUMENTS

| 2,656,508 A | 10/1953 | Coulter |
| 7,312,085 B2 | 12/2007 | Chou et al. |

(Continued)

FOREIGN PATENT DOCUMENTS

| CN | 102876628 A | 1/2013 |
| CN | 202688332 U | 1/2013 |

(Continued)

OTHER PUBLICATIONS

Abdolvand et al. Long-Term Retinal Differentiation of Human Induced Pluripotent Stem Cells in a Continuously Perfused Microfluidic Culture Device. Biotechnol. J. 2019, 14, 1800323. Copyright 2018. 13 pages.
(Continued)

*Primary Examiner* — Brian R Gordon
(74) *Attorney, Agent, or Firm* — Wilson Sonsini Goodrich & Rosati

(57) ABSTRACT

The present disclosure provides systems and methods for bioprocessing. The systems and methods can be implemented using a chip (solid support comprising a bioprocessing chamber). The bioprocessing chamber can be fluidically connected to a feeding input channel. The chip can permit a fluid to flow from the feeding input channel through the bioprocessing chamber for cell seeding, perfusion, and/or expansion. The bioprocessing chamber can be in fluidic communication with a collection output. The cells can be harvested from the bioprocessing chamber through the collection output.

15 Claims, 41 Drawing Sheets

(51) Int. Cl.
*C12M 1/32* (2006.01)
*C12M 3/06* (2006.01)

(52) U.S. Cl.
CPC ....... *B01L 3/502761* (2013.01); *C12M 23/12* (2013.01); *C12M 29/04* (2013.01); *C12M 29/10* (2013.01); *B01L 2400/0487* (2013.01)

(56) References Cited

U.S. PATENT DOCUMENTS

| | | | |
|---|---|---|---|
| 7,452,726 | B2 | 11/2008 | Chou et al. |
| 8,333,935 | B2 | 12/2012 | Lee et al. |
| 8,658,418 | B2 | 2/2014 | Daridon |
| 9,121,847 | B2 | 9/2015 | Kamm et al. |
| 9,134,207 | B2 | 9/2015 | Zhou et al. |
| 9,200,335 | B2 | 12/2015 | Niazi |
| 9,260,688 | B2 | 2/2016 | Hung et al. |
| 9,273,276 | B2 | 3/2016 | Shuler et al. |
| 9,422,409 | B2 | 8/2016 | Lee et al. |
| 9,469,840 | B2 | 10/2016 | Le Berre et al. |
| 9,506,846 | B2 | 11/2016 | Rubner et al. |
| 9,732,316 | B2 | 8/2017 | Shuler et al. |
| 9,879,308 | B2 | 1/2018 | Holton et al. |
| 9,909,102 | B2 | 3/2018 | Baruch et al. |
| 9,926,521 | B2 | 3/2018 | Daridon |
| 9,969,963 | B2 | 5/2018 | Hung et al. |
| 10,012,640 | B2 | 7/2018 | Pant et al. |
| 10,023,832 | B2 | 7/2018 | Wikswo et al. |
| 10,078,075 | B2 | 9/2018 | Wikswo et al. |
| 10,324,011 | B2 | 6/2019 | D'Silva et al. |
| 10,444,223 | B2 | 10/2019 | Wikswo et al. |
| 10,450,540 | B2 | 10/2019 | Gebauer et al. |
| 10,577,574 | B2 | 3/2020 | Wikswo et al. |
| 10,690,255 | B2 | 6/2020 | Juncker et al. |
| 11,007,520 | B2 | 5/2021 | Lowe, Jr. et al. |
| 2002/0187072 | A1 | 12/2002 | Karp et al. |
| 2004/0132175 | A1 | 7/2004 | Vetillard et al. |
| 2006/0154361 | A1 | 7/2006 | Wikswo et al. |
| 2011/0117634 | A1 | 5/2011 | Halamish et al. |
| 2012/0322097 | A1 | 12/2012 | Charest et al. |
| 2013/0287613 | A1 | 10/2013 | Gould et al. |
| 2014/0004501 | A1* | 1/2014 | Talebpour ............... C12N 13/00 435/173.6 |
| 2014/0228250 | A1 | 8/2014 | Wang et al. |
| 2014/0349279 | A1 | 11/2014 | Berthelot et al. |
| 2016/0025761 | A1 | 1/2016 | West et al. |
| 2016/0047735 | A1 | 2/2016 | Grisham et al. |
| 2016/0103044 | A1 | 4/2016 | Kopf-Sill |
| 2016/0281126 | A1 | 9/2016 | Qin et al. |
| 2016/0340632 | A1 | 11/2016 | Breinlinger et al. |
| 2017/0209864 | A1 | 7/2017 | Grisham et al. |
| 2017/0292104 | A1 | 10/2017 | Ebrahimi Warkiani et al. |
| 2017/0333900 | A1 | 11/2017 | Grisham et al. |
| 2018/0001231 | A1 | 1/2018 | Puleo et al. |
| 2018/0120294 | A1 | 5/2018 | Collins |
| 2018/0229241 | A1 | 8/2018 | Bishop et al. |
| 2018/0361053 | A1 | 12/2018 | Fiering et al. |
| 2019/0064148 | A1 | 2/2019 | Beckwith et al. |
| 2019/0106664 | A1 | 4/2019 | Hung et al. |
| 2019/0137369 | A1 | 5/2019 | D'Silva et al. |
| 2019/0169572 | A1 | 6/2019 | Shi et al. |
| 2019/0177678 | A1 | 6/2019 | Bigliardi et al. |
| 2019/0249130 | A1 | 8/2019 | Griffin et al. |
| 2020/0095525 | A1* | 3/2020 | Chou ..................... C12M 23/34 |
| 2020/0231918 | A1 | 7/2020 | Kozbial |
| 2021/0054324 | A1 | 2/2021 | Pompano et al. |
| 2021/0115375 | A1 | 4/2021 | Murthy et al. |
| 2021/0148895 | A1 | 5/2021 | Hewitt et al. |
| 2021/0205810 | A1 | 7/2021 | Haun et al. |
| 2021/0238523 | A1 | 8/2021 | Thon et al. |
| 2021/0299675 | A1* | 9/2021 | Horiike ............... G01N 30/0005 |
| 2021/0355426 | A1 | 11/2021 | Cejas et al. |
| 2021/0403847 | A1 | 12/2021 | Takayama et al. |
| 2022/0074831 | A1* | 3/2022 | Xu ..................... G01N 1/4005 |
| 2022/0161258 | A1* | 5/2022 | Obermann ......... G01N 15/0826 |
| 2022/0204903 | A1* | 6/2022 | Nordon ................. C12M 29/10 |
| 2022/0249761 | A1* | 8/2022 | Haun ..................... A61M 1/892 |
| 2022/0282212 | A1 | 9/2022 | Shi et al. |
| 2022/0282213 | A1 | 9/2022 | Shi et al. |
| 2022/0282214 | A1 | 9/2022 | Shi et al. |
| 2023/0167392 | A1 | 6/2023 | Cejas et al. |

FOREIGN PATENT DOCUMENTS

| | | |
|---|---|---|
| CN | 106232801 A | 12/2016 |
| CN | 113388583 A | 9/2021 |
| EP | 1297389 A2 | 4/2003 |
| EP | 1392814 B1 | 6/2007 |
| EP | 2012923 A1 | 1/2009 |
| EP | 2721141 A1 | 4/2014 |
| EP | 2758521 A1 | 7/2014 |
| EP | 2914379 A1 | 9/2015 |
| EP | 2920574 A1 | 9/2015 |
| EP | 2971279 A2 | 1/2016 |
| EP | 2971287 A2 | 1/2016 |
| EP | 3029135 A1 | 6/2016 |
| EP | 3071327 A1 | 9/2016 |
| EP | 3148697 A1 | 4/2017 |
| EP | 3169626 A1 | 5/2017 |
| EP | 3174976 A1 | 6/2017 |
| EP | 3190172 A2 | 7/2017 |
| EP | 3230717 A2 | 10/2017 |
| EP | 3285927 A2 | 2/2018 |
| EP | 3286296 A1 | 2/2018 |
| EP | 3286298 A1 | 2/2018 |
| EP | 3402814 A1 | 11/2018 |
| EP | 3430131 A1 | 1/2019 |
| EP | 3484991 A1 | 5/2019 |
| EP | 3541516 A1 | 9/2019 |
| EP | 3549099 A1 | 10/2019 |
| EP | 2331954 B1 | 3/2020 |
| EP | 3647405 A1 | 5/2020 |
| EP | 3662056 A2 | 6/2020 |
| EP | 3676004 A1 | 7/2020 |
| EP | 3703859 A1 | 9/2020 |
| EP | 3737505 A1 | 11/2020 |
| EP | 3790662 A1 | 3/2021 |
| EP | 3793735 A1 | 3/2021 |
| EP | 3803341 A2 | 4/2021 |
| EP | 3839037 A1 | 6/2021 |
| EP | 3850336 A1 | 7/2021 |
| EP | 3981867 A1 | 4/2022 |
| EP | 3839037 B1 | 8/2022 |
| EP | 4058563 A1 | 9/2022 |
| JP | 2010161238 A | 7/2010 |
| JP | 2013255487 A | 12/2013 |
| JP | 2014510539 A | 5/2014 |
| WO | WO-9015859 A1 | 12/1990 |
| WO | WO-02053193 A2 | 7/2002 |
| WO | WO-2007024701 A3 | 5/2009 |
| WO | WO-2010042784 A2 | 4/2010 |
| WO | WO-2011027832 A1 | 3/2011 |
| WO | WO-2013019491 A1 | 2/2013 |
| WO | WO-2013036997 A1 | 3/2013 |
| WO | WO-2014145075 A2 | 9/2014 |
| WO | WO-2015200857 A1 | 12/2015 |
| WO | WO-2016019393 A1 | 2/2016 |
| WO | WO-2017059273 A1 | 4/2017 |
| WO | WO-2018015561 A1 | 1/2018 |
| WO | WO-2018085453 A1 | 5/2018 |
| WO | WO-2019046766 A2 | 3/2019 |
| WO | WO-2019219841 A1 | 11/2019 |
| WO | WO-2019232473 A2 | 12/2019 |
| WO | WO-2019243598 A1 | 12/2019 |
| WO | WO-2020089487 A1 | 5/2020 |
| WO | WO-2020227772 A1 | 11/2020 |
| WO | WO-2021096850 A1 | 5/2021 |
| WO | WO-2021110896 A1 | 6/2021 |
| WO | WO-2021255463 A1 | 12/2021 |
| WO | WO-2022073754 A1 | 4/2022 |
| WO | WO-2023099898 A1 | 6/2023 |
| WO | WO-2023099899 A2 | 6/2023 |
| WO | WO-2024052678 A1 | 3/2024 |
| WO | WO-2024052679 A1 | 3/2024 |

(56) References Cited

FOREIGN PATENT DOCUMENTS

| WO | WO-2024074828 A1 | 4/2024 |
|---|---|---|
| WO | WO-2024153915 A2 | 7/2024 |
| WO | WO-2024153916 A2 | 7/2024 |

OTHER PUBLICATIONS

Agostini et al. Polydimethylsiloxane (PDMS) irreversible bonding to untreated plastics and metals for microfluidics applications. APL Mater. 7, 081108 (2019). Published Online: Aug. 14, 2019. 7 pages.
Akagi et al. Miniaturized Embryo Array for Automated Trapping, Immobilization and Microperfusion of Zebrafish Embryos. PLoS One, vol. 7, Issue 5, e36630 (May 14, 2012). 13 pages.
Arayanarakool et al. Low-temperature, simple and fast integration technique of microfluidic chips by using a UV-curable adhesive. Lab Chip, 2010, 10, 2115-2121.
Awaja et al. Lab-on-a-chip device made by autohesion-bonded polymers. Biomedical Microdevices (2018) 20: 7. Published online: Dec. 18, 2017. 9 pages.
Baudoin et al. Behavior of HepG2/C3A cell cultures in a microfluidic bioreactor. Biochemical Engineering Journal 53 (2011) 172-181.
Beal et al. A rapid, inexpensive surface treatment for enhanced functionality ofpolydimethylsiloxane microfluidic channels. Biomicrofluidics 6, 036503 (2012). Published online Jul. 30, 2012. 11 pages.
Becker et al. Microfluidic devices for cell culture and handling in organ-on-a-chip applications. Proc. of SPIE, vol. 8976 (2014). 7 pages.
Bruijns et al. Cyclic Olefin Copolymer Microfluidic Devices for Forensic Applications. Biosensors (Basel). Biosensors 9, 85 (Jul. 4, 2019). 14 pages.
Bévierre. Gene therapy: the challenge of biomanufacturing (Nov. 6, 2017). Retrieved Feb. 14, 2022 at URL: https://www.linkedin.com/pulse/gene-therapy-challenge-biomanufacturing-marc-olivier-b%C3%A9vierre. 7 pages.
Cejas et al. Particle Deposition Kinetics of Colloidal Suspensions in Microchannels at High Ionic Strength. Langmuir 33, 6471-6480 (Jun. 12, 2017).
Cejas et al. Universal diagram for the kinetics of particle deposition in microchannels. Phys. Rev. E 98, 062606 (Dec. 10, 2018). 12 pages.
Chen et al. High-Throughput Cancer Cell Sphere Formation for Characterizing the Efficacy of Photo Dynamic Therapy in 3D Cell Cultures. Scientific Reports 5:12175 (Jul. 8, 2015). 12 pages.
Cheong et al. Using a Microfluidic Device for High-Content Analysis of Cell Signaling. Sci Signal. Jun. 16, 2009;2(75):pl2. 31 pages.
Choi et al. Microfluidic parallel circuit for measurement of hydraulic resistance. Biomicrofluidics 4, 034110 (2010). Published online Aug. 31, 2010. 9 pages.
Ciftlik et al. Microfluidic processor allows rapid HER2 immunohistochemistry of breast carcinomas and significantly reduces ambiguous (2+) read-outs. PNAS, vol. 110, No. 14, pp. 5363-5368 (Apr. 2, 2013).
Coluccio et al. Microfluidic platforms for cell cultures and investigations. Microelectronic Engineering 208 (2019) 14-28. Available online Jan. 28, 2019.
Crane et al. A Microfluidic System for Studying Ageing and Dynamic Single-Cell Responses in Budding Yeast. PLoS One 9(6): e100042 (Jun. 20, 2014). 10 pages.
Cui et al. Application of microfluidic chip technology in pharmaceutical analysis: A review. Journal of Pharmaceutical Analysis 9 (2019) 238-247. Available online Dec. 6, 2018.
Deng. Microfluidic Approaches for Probing Protein Phosphorylation in Cells. Dissertation. Virginia Polytechnic Institute and State University, Blacksburg, Virginia (May 24, 2018). Retrieved Sep. 29, 2021 at: https://vtechworks.lib.vt.edu/bitstream/handle/10919/96545/Deng_J_D_2018.pdf?sequence=1&isAllowed=y. 178 pages.
Di Carlo et al. Dynamic single cell culture array. Lab Chip 6, 1445-1449 (2006). Published online Sep. 4, 2006.
Di Carlo et al. Dynamic Single-Cell Analysis for Quantitative Biology. Analytical Chemistry, pp. 7920-7925 (Dec. 1, 2006).
Di Carlo et al. Single-Cell Enzyme Concentrations, Kinetics, and Inhibition Analysis Using High-Density Hydrodynamic Cell Isolation Arrays. Anal. Chem. vol. 78, No. 14, pp. 4925-4930 (2006).
Dura et al. Deformability-based microfluidic cell pairing and fusion. Lab Chip, 2014, 14, 2783-2790.
El-Ali et al. Cells on chips. Nature, vol. 442, pp. 403-411 (Jul. 27, 2006).
EP18306441 European Search Report dated Apr. 12, 2019.
EP18306441.9 Communication Pursuant to Rule 114(2) EPC dated Nov. 13, 2020.
EP18306441.9 Extended European Search Report dated Apr. 18, 2019.
Faley, et al. Microfluidic platform for real-time signaling analysis of multiple single T cells in parallel. Lab on a Chip 8.10 (2008): 1700-1712.
Frenz et al. Microfluidic production of droplet pairs. Langmuir 2008, 24, 12073-12076. Published on Web Sep. 27, 2008.
Frick et al. Nano-scale microfluidics to study 3Dchemotaxis at the single cell level. PLoS One 13(6): e0198330 (Jun. 7, 2018). 17 pages.
Frimat et al. A microfluidic array with cellular valving for single cell co-culture. Lab Chip, 11, 231-237 (2011).
Gao et al. A versatile valve-enabled microfluidic cell co-culture platform and demonstration of its applications to neurobiology and cancer biology. Biomed Microdevices (2011) 13:539-548. Published online: Mar. 19, 2011.
Gómez-Sjöberg et al. Versatile, Fully Automated, Microfluidic Cell Culture System. Anal. Chem. 2007, 79, 22, 8557-8563. Published on Web Oct. 23, 2007. With Supporting Information, pp. S1-S13.
Grimes et al. Shrinky-Dink microfluidics: rapid generation of deep and rounded patterns. Lab Chip, 2008, 8, 170-172. Published online Nov. 20, 2007.
Gu et al. Chemical-Assisted Bonding of Thermoplastics/Elastomer for Fabricating Microfluidic Valves. Anal Chem. Jan. 1, 2011; 83(1): 446-452.
Gu et al. Computerized microfluidic cell culture using elastomeric channels and Braille displays. PNAS, vol. 101, No. 45, pp. 15861-15866 (Nov. 9, 2004).
Guidance for Industry: Current Good Tissue Practice (CGTP) and Additional Requirements for Manufacturers of Human Cells, Tissues, and Cellular and Tissue-Based Products (HCT/Ps). U.S. Department of Health and Human Services, Food and Drug Administration, Center for Biologics Evaluation and Research (Dec. 2011). 67 pages. Retrieved Feb. 4, 2022 at URL: https://www.fda.gov/media/82724/download.
Guild et al. Embryonic Stem Cells Cultured in Microfluidic Chambers Take Control of Their Fate by Producing Endogenous Signals Including LIF. Stem Cells 34:1501-1512 (2016).
Guo et al. Deformability based Cell Sorting using Microfluidic Ratchets Enabling Phenotypic Separation of Leukocytes Directly from Whole Blood. Scientific Reports, vol. 7, Article No. 6627 (2017). Published online Jul. 16, 2017. 11 pages. With Supplemental Information (6 pages).
Halldorsson et al. Advantages and challenges of microfluidic cell culture in polydimethylsiloxane devices. Biosensors and Bioelectronics 63 (2015) 218-231. Available online Jul. 19, 2014.
Hansen et al. High-throughput microfluidics to control and measure signaling dynamics in single yeast cells. Nature Protocols, vol. 10, No. 8, pp. 1181-1197 (2015). Published online Jul. 9, 2015.
Hansen et al. Systematic investigation of protein phase behavior with a microfluidic formulator. PNAS, vol. 101, No. 40, pp. 14431-14436 (Oct. 5, 2004).
Huebner et al. Static microdroplet arrays: a microfluidic device for droplet trapping, incubation and release for enzymatic and cell-based assays. Lab Chip, 2009, 9, 692-698. Published online Nov. 27, 2008.
Hung et al. Continuous Perfusion Microfluidic Cell Culture Array for High-Throughput Cell-Based Assays. Biotechnology and Bioengineering, vol. 89, No. 1 (Jan. 5, 2005). Published online Dec. 3, 2004 in Wiley InterScience. 8 pages.

(56) References Cited

OTHER PUBLICATIONS

Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1 to 12822-12. doi: 10.1063/1.3682098. Epub Mar. 15, 2012.

Jeon et al. Hot embossing for fabrication of a microfluidic 3D cell culture platform. Biomed Microdevices. Apr. 2011 ; 13(2): 325-333.

Jin et al. A microfluidic device enabling high-efficiency single cell trapping. Biomicrofluidics 9, 014101 (2015). Published online Jan. 7, 2015. 16 pages.

Kaminski et al. Droplet microfluidics for microbiology: techniques, applications and challenges. Lab on a Chip (2006). 20 pages.

Kim et al. 1600 Parallel Microchamber Microfluidic Device for Fast Sample Array Preparation Using the Immiscibility of Two Liquids. Micromachines 8, 63 (Feb. 23, 2017). 6 pages.

Kim et al. A high-throughput microfluidic single-cell screening platform capable of selective cell extraction. Lab Chip, 2015, 15, 2467-2475.

Kim et al. A practical guide to microfluidic perfusion culture of adherent mammalian cells. Lab Chip, 2007, 7, 681-694. Published online May 11, 2007.

Kim et al. Generating steep, shear-free gradients of small molecules for cell culture. Biomed Microdevices (2009) 11:65-73. Published online: Aug. 8, 2008.

Kim et al. Integration of a microfluidic chip with a size-based cell bandpass filter for reliable isolation of single cells. Lab Chip, 2015, 15, 4128-4132.

Kneale. Medical Plastics 101: Cyclic Olefin Copolymer Fulfills Complex Medtech Performance Requirements. plasticstoday.com website. Feb. 2, 2021. Retrieved Aug. 23, 2022 at URL: https://www.plasticstoday.com/medical/medical-plastics-101-cyclic-olefin-copolymer-fulfills-complex-medtech-performance. 14 pages.

Kusuma et al. Effect of the Microenvironment on Mesenchymal Stem Cell Paracrine Signaling: Opportunities to Engineer the Therapeutic Effect. Stem Cells and Development, vol. 26, No. 9, pp. 617-631 (2017). Prepublished on Liebert Instant Online Feb. 10, 2017.

Kwapiszewska et al. A microfluidic-based platform for tumour spheroid culture, monitoring and drug screening. Lab Chip, 2014, 14, 2096-2104.

Lazar et al. Microfluidic reactors for advancing the MS analysis of fast biological responses. Microsystems & Nanoengineering ( 2019) 5:7. 16 pages.

Lecault et al. High-throughput analysis of single hematopoietic stem cell proliferation in microfluidic cell culture arrays. Nature Methods, vol. 8, No. 7, pp. 581-586 (Jul. 2011). Published online May 22, 2011. Corrected online Jun. 3, 2011. With Online Methods (3 pages).

Lin et al. A microfluidic dual-well device for high throughput single-cell capture and culture. Lab Chip, 2015, 15, 2928-2938.

Liu et al. Characterization of Bonding Between Poly(dimethylsiloxane) and Cyclic Olefin Coplymer Using Corona Discharge Induced Grafting Polymerization. J Colloid Interface Sci. Jan. 1, 2012; 365(1): 289-295.

Lu et al. Designing compartmentalized hydrogel microparticles for cell encapsulation and scalable 3D cell culture. J. Mater. Chem. B, 2015, 3, 353-360.

Macown et al. Robust, microfabricated culture devices with improved control over the soluble microenvironment for the culture of embryonic stem cells. Biotechnol. J. 2014, 9, 805-813.

Marcy et al. Nanoliter reactors improve multiple displacement amplification of genomes from single cells. PLoS Genet. Sep. 2007; 3(9): e155. Published online Sep. 21, 2007.

Mehling et al. Microfluidic cell culture. Curr Opin Biotechnol. 2014, 25:95-102. Available online Nov. 12, 2013.

Moore et al. Cell therapy manufacturing. BioProcess International website (Mar. 1, 2014). Retrieved Feb. 11, 2022 at URL: https://bioprocessintl.com/manufacturing/cell-therapies/cell-therapy-manufacturing-350564/. 10 pages.

Occhetta et al. Stoichiometric control of live cell mixing to enable fluidically-encoded co-culture models in perfused microbioreactor arrays. Integr. Biol., 2016, 8, 194-204.

Ogilvie et al. Solvent Processing of PMMA and COC Chips for Bonding Devices with Optical Quality Surfaces. 14th International Conference on Miniaturized Systems for Chemistry and Life Sciences, Groningen, The Netherlands, pp. 1244-1246 (Oct. 3-7, 2010).

Ogończyk et al. Bonding of microfluidic devices fabricated in polycarbonate. Lab Chip, 2010, 10, 1324-1327.

Oh et al. Design of pressure-driven microfluidic networks using electric circuit analogy. Lab Chip, 2012, 12, 515-545.

Park et al. Radial Flow Hepatocyte Bioreactor Using Stacked Microfabricated Grooved Substrates. Biotechnology and Bioengineering, vol. 99, No. 2, pp. 455-467 (Feb. 1, 2008). Published online Jul. 11, 2007 in Wiley InterScience.

PCT/EP2019/080127 International Preliminary Report on Patentability dated Apr. 27, 2021.

PCT/EP2019/080127 International Search Report and Written Opinion dated Feb. 17, 2020.

Peng et al. Roll-to-roll hot embossing system with shape preserving mechanism for the large area fabrication of microstructures. Rev. Sci. Instrum. 87, 105120 (2016). Published online Oct. 19, 2016. 13 pages.

Petricciani et al. Scientific considerations for the regulatory evaluation of cell therapy products. Biologicals 50 (2017) 20-26. Available online Sep. 6, 2017.

Pitingolo et al. An automatic cell culture platform for differentiation of human induced pluripotent stem cells. Microelectronic Engineering 231 (2020) 111371. Available online Jun. 2, 2020. 7 pages.

Raimes et al. Transfection in perfused microfluidic cell culture devices: A case study. Process Biochemistry 59 (2017) 297-302. Available online Sep. 12, 2016.

Reichen et al. Development of a Multiplexed Microfluidic Platform for the Automated Cultivation of Embryonic Stem Cells. Journal of Laboratory Automation, published online Aug. 22, 2013. 11 pages.

Reichen et al. Microfabricated Modular Scale-Down Device for Regenerative Medicine Process Development. PLOS One, vol. 7, Issue 12, e52246 (Dec. 19, 2012). 12 pages.

Rettig, et al. Large-scale single-cell trapping and imaging using microwell arrays. Anal Chem. Sep. 1, 2005;77(17):5628-34. Published on Web Jul. 30, 2005.

Rousset et al. Simulation-assisted design of microfluidic sample traps for optimal trapping and culture of non-adherent single cells, tissues, and spheroids. Scientific Reports 7:245 (Mar. 21, 2017). 12 pages.

Rubio et al. FT-IR study of the hydrolysis and condensation of 3-(2-amino-ethylamino)propyl-trimethoxy silane. Boletín de la Sociedad Española de Cerámica y Vidrio 57 (2018) 160-168. Available online Dec. 15, 2017.

Russo et al. Advances in microfluidic 3D cell culture for preclinical drug development. Prog Mol Biol Transl Sci, vol. 187, pp. 163-204 (2022).

Samazan et al. AIM Biochips—3D cell culture platform for Immunotherapy and T Cell therapy studies. tebu-bio blog (May 18, 2018). Retrieved Feb. 4, 2022 at URL: https://www.tebu-bio.com/blog/aim-biochips-3d-cell-culture-platform-for-immunotherapy-and-t-cell-therapy-studies/. 4 pages.

Schaerli et al. Continuous-Flow Polymerase Chain Reaction of Single-Copy DNA in Microfluidic Microdroplets. Anal. Chem. 2009, 81, 302-306. Published on Web Dec. 4, 2008.

Shin et al. Microfluidic assay for simultaneous culture of multiple cell types on surfaces or within hydrogels. Nature Protocols, vol. 7, No. 7, pp. 1247-1259 (2012). Published online Jun. 7, 2012.

Skelley et al. Microfluidic Control of Cell Pairing and Fusion. Nat Methods. Feb. 2009 ; 6(2): 147-152.

Sonnen et al. Microfluidics as an Emerging Precision Tool in Developmental Biology. Developmental Cell 48, pp. 293-311 (Feb. 11, 2019).

Super et al. Real-time monitoring of specific oxygen uptake rates of embryonic stem cells in a microfluidic cell culture device. Biotechnol. J. 2016, 11, 1179-1189.

(56) References Cited

OTHER PUBLICATIONS

Supplementary Material, 5 pages for: Arayanarakool et al. Low-temperature, simple and fast integration technique of microfluidic chips by using a UV-curable adhesive. Lab on a Chip, Issue 16 (2010).
Supporting Information for Ciftlik et al. Microfluidic processor allows rapid HER2 immunohistochemistry of breast carcinomas and significantly reduces ambiguous (2+) read-outs. PNAS, vol. 110, No. 14, pp. 5363-5368 (Apr. 2, 2013). Retrieved Feb. 10, 2022 at URL: https://www.pnas.org/highwire/filestream/611979/field_highwire_adjunct_files/0/pnas.201211273SI.pdf. 9 pages.
Szita et al. An automated microfluidic perfusion device for adherent cell reprogramming, expansion and culture condition monitoring. Abstracts / New Biotechnology 44S (2018) S13-S15. One page.
Tan et al. A trap-and-release integrated microfluidic system for dynamic microarray applications. PNAS, vol. 104, No. 4, pp. 1146-1151 (Jan. 23, 2007).
Tang et al. A facile route for irreversible bonding of plastic-PDMS hybrid microdevices at room temperature. Lab Chip, 2010, 10, 1274-1280. Published online Feb. 16, 2010.
Tehranirokh et al. Microfluidic devices for cell cultivation and proliferation. Biomicrofluidics 7, 051502 (2013). Published Online: Oct. 29, 2013. 32 pages.
Titmarsh et al. Full factorial screening of human embryonic stem cell maintenance with multiplexed microbioreactor arrays. Biotechnol. J. 2013, 8, 822-834.
Titmarsh et al. Induction of Human iPSC-Derived Cardiomyocyte Proliferation Revealed by Combinatorial Screening in High Density Microbioreactor Arrays. Scientific Reports 6:24637 (Apr. 21, 2016). 15 pages.
Titmarsh et al. Microbioreactor Arrays for Full Factorial Screening of Exogenous and Paracrine Factors in Human Embryonic Stem Cell Differentiation. PLOS One, vol. 17, Issue 12, e52405 (Dec. 26, 2012). 12 pages.
Titmarsh et al. Optimization of Flowrate for Expansion of Human Embryonic Stem Cells in Perfusion Microbioreactors. Biotechnology and Bioengineering, vol. 108, No. 12, pp. 2894-2904 (Dec. 2011). Published online Jul. 5, 2011 in Wiley Online Library.
Toepke et al. PDMS absorption of small molecules and consequences in microfluidic applications. Lab Chip, 2006, 6, 1484-1486.
Um et al. Mesh-integrated microdroplet array for simultaneous merging and storage of single-cell droplets. Lab Chip, 2012, 12, 1594-1597.
Virumbrales-Muñoz et al. Enabling cell recovery from 3Dcell culture microfluidic devices for tumour microenvironment biomarker profiling. Scientific Reports (2019) 9:6199. Published online Apr. 17, 2019. 14 pages.
Vollertsen et al. Standardized, Modular Parallelization Platform for Microfluidic Large-Scale Integration Cell Culturing Chips. Poster. MicroTAS Conference (2018). One page.
Vyawahare et al. Miniaturization and Parallelization of Biological and Chemical Assays in Microfluidic Devices. Chemistry & Biology 17, pp. 1052-1065 (Oct. 29, 2010).
Wang et al. A microfluidics-based turning assay reveals complex growth cone responses to integrated gradients of substrate-bound ECM molecules and diffusible guidance cues. Lab Chip, 2008, 8, 227-237. Published online Jan. 4, 2008.
Wasay et al. Gecko gaskets for self-sealing and high-strength reversible bonding of microfluidics. Lab Chip, 2015, 15, 2749. 5 pages.
Wu et al. Stem cells in microfluidics. Biomicrofluidics 5, 013401 (2011). Published online Mar. 30, 2011. 26 pages.
Young et al. Fundamentals of microfluidic cell culture in controlled microenvironments. Chem Soc Rev. Mar. 2010 ; 39(3): 1036-1048.
Zhang et al. A novel method of cell culture based on the microfluidic chip for regulation of cell density. Biotechnology and Bioengineering. 2021; 118:852-862.
Zhang et al. Block-Cell-Printing for live single-cell printing. PNAS, vol. 111, No. 8, pp. 2948-2953 (Feb. 25, 2014).
PCT/GB2022/053050 International Search Report and Written Opinion dated May 22, 2023.
PCT/GB2022/053050 Partial Search Report and Provisional Opinion dated Mar. 9, 2023.
PCT/GB2022/053051 Partial Search Report and Provisional Opinion dated Mar. 23, 2023.
PCT/GB2022/053051 International Search Report and Written Opinion dated Jun. 2, 2023.
CN201980085594.1 Office Action and Search Report dated Sep. 21, 2023 (w/ machine translation).
Co-pending U.S. Appl. No. 18/679,064, inventors Cejas; Cesare M. et al., filed on May 30, 2024.
Co-pending U.S. Appl. No. 18/679,196, inventors Cejas; Cesare M. et al., filed on May 30, 2024.
JP2021-524326 Office Action dated Sep. 12, 2023 (w/ machine translation).
JP2021-524326 Search Report dated Aug. 9, 2023 (w/ machine translation).
PCT/GB2022/053050 International Preliminary Report on Patentability dated May 2, 2024.
PCT/GB2022/053051 International Preliminary Report on Patentability dated May 2, 2024.
PCT/GB2023/052310 International Search Report and Written Opinion dated Jan. 5, 2024.
PCT/GB2023/052312 International Search Report and Written Opinion dated Jan. 5, 2024.
U.S. Appl. No. 17/290,394 Office Action dated Feb. 22, 2024.

\* cited by examiner

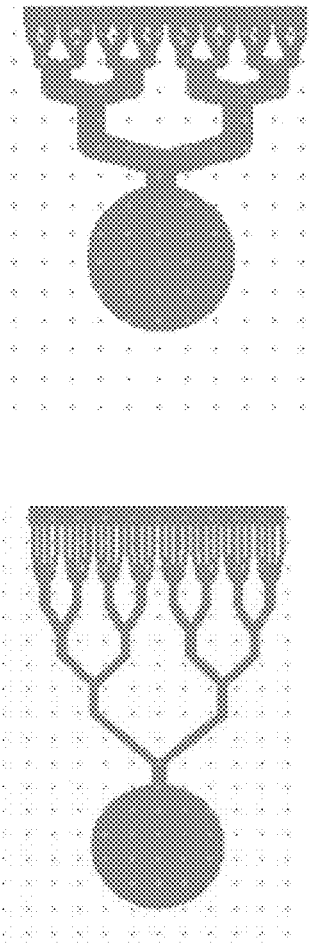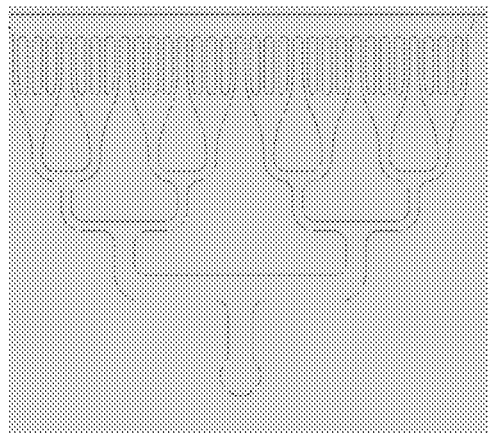
FIG. 5C

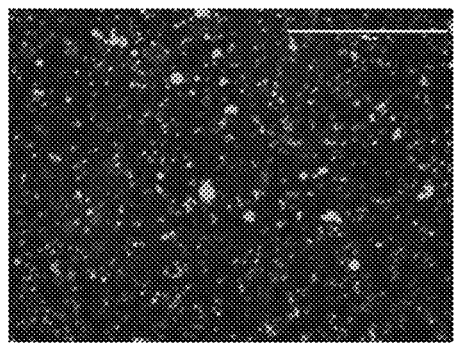
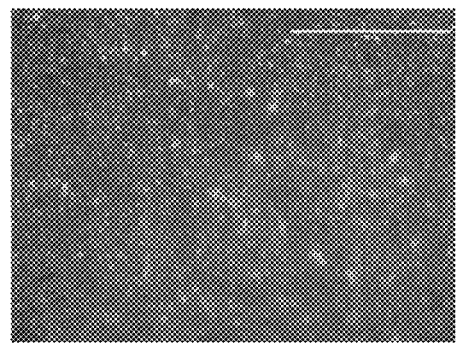
*FIG. 8*  *FIG. 9*
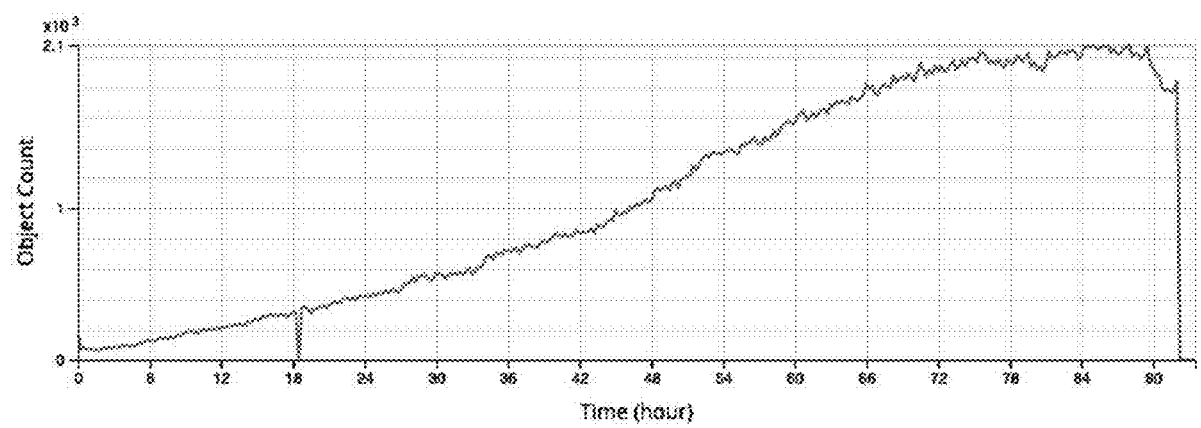
*FIG. 10*

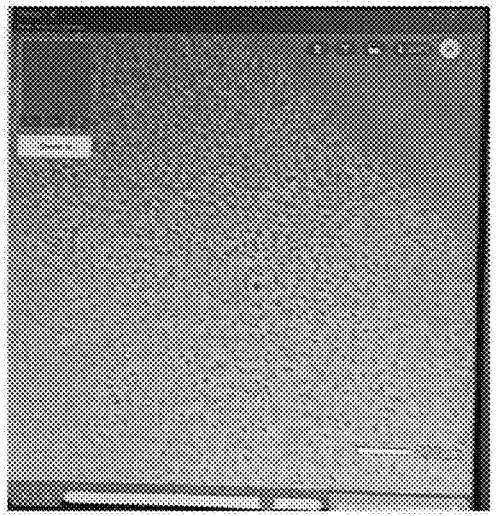
Before Harvest
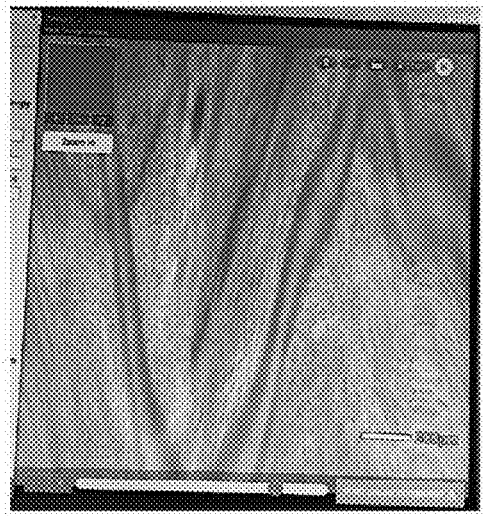
During Harvest & Vortex
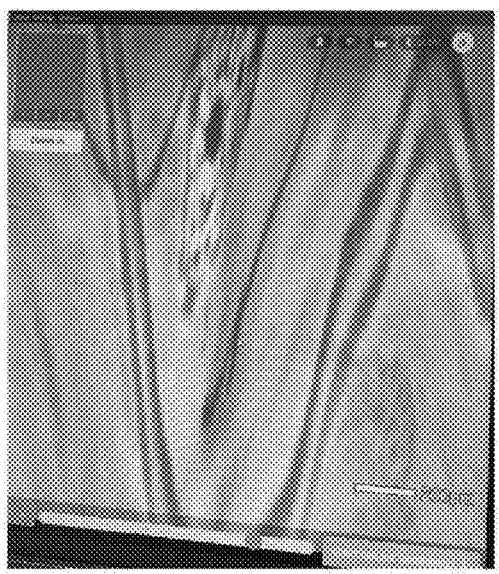
End of Harvest & Vortex
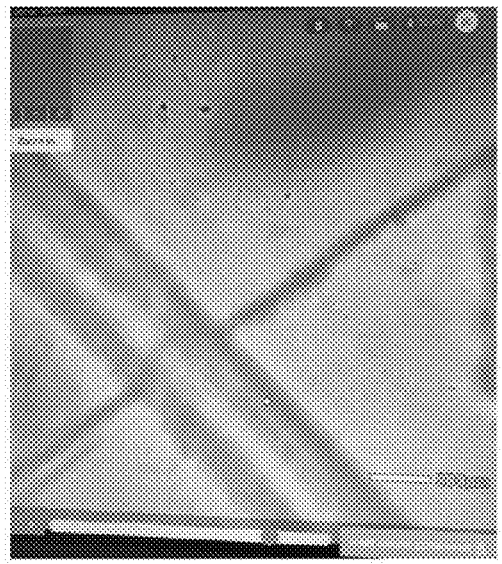
Final View of Chip
*FIG. 21*

2400
TOP VIEW
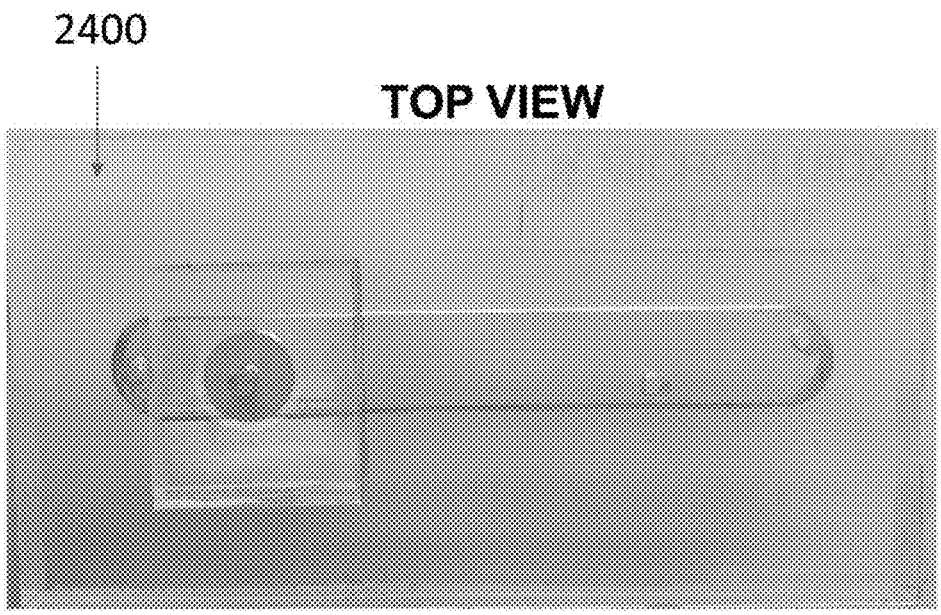
2400
BOTTOM VIEW
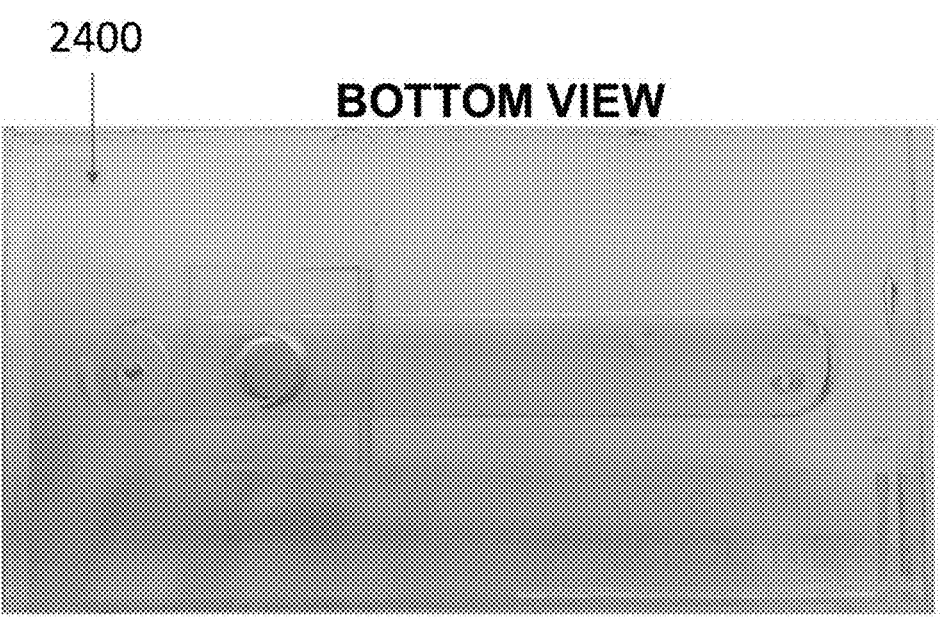
*FIG. 25*

SYSTEMS AND METHODS FOR BIOPROCESSING

CROSS REFERENCE

This application is related to U.S. Provisional Patent Application No. 63/285,062 filed on Dec. 1, 2021, which application is incorporated herein by reference in its entirety.

BACKGROUND

There are various limitations with conventional cell therapy bioprocessing, which can be complex since it can involve (a) the extraction of cells from the patient, (b) the treatment and modification of these cells ex vivo, and then the (c) reintroduction of these cells back inside the body of the patient. High-throughput cell processing destined for cell therapy treatments can involve precise control of flow, collection, growth, and manipulation of biological cells. An aspect to high-throughput cell processing is streamlining the processes involved from seeding all the way to harvesting, with minimal invasive interventions. There is a need for high-throughput multifunctional microfluidic chips capable of carrying out in situ cell processing without invasive interventions, which can limit the risk of cell loss and contamination that would otherwise accrue with multiple transfers.

SUMMARY

The present disclosure provides a multifunctional microfluidic-based system that permits streamlined non-invasive in situ bioprocessing operations for adherent and suspension cells. The system can comprise one or more microfluidic chips and microfluidic connections to miniaturize culture devices and increase throughput.

The one or more microfluidic chips (solid supports) can be designed to optimize the bioprocessing operations involved in cell production for cell therapy applications. These operations aimed for cell production can include, for example, seeding, activation, viral or non-viral transduction, proliferation and/or differentiation, washing and/or purification, sampling, and harvesting—all of which can be performed within a bioprocessing chamber of the chip without the need of external transplants and/or invasive interventions.

In one aspect, the present disclosure provides a solid support comprising a microfluidic feeding input channel; a bioprocessing chamber comprising a bottom surface, wherein the bioprocessing chamber is fluidically connected to the feeding input channel; and a collection output fluidically connected to the bioprocessing chamber via the bottom or top surface. In some embodiments, the collection output is not orthogonal to the bottom surface. In some embodiment, the collection output is orthogonal to the bottom surface In some embodiments, the collection output is orthogonal to the bottom surface or top surface. In some embodiments, the collection output is parallel to the bottom or top surface.

In some embodiments, a flow path comprising the microfluidic feeding input channel, the bioprocessing chamber and (i) a feeding outlet or (ii) the collection is closed. In some embodiments, a flow path comprising the microfluidic feeding input channel, the bioprocessing chamber and the collection output is closed during a seeding or perfusion operation. In some embodiments, a flow path comprising the microfluidic feeding input channel, the bioprocessing chamber and (i) a feeding outlet or (ii) the collection output is open.

In some embodiments, the bioprocessing chamber is elongated and comprises a first end wall and a second end wall opposite the first end wall. In some embodiments, the bottom surface is substantially orthogonal to the first end wall and the second end wall.

In some embodiments, the microfluidic feeding input channel is fluidically connected to the first end wall of the bioprocessing chamber and the collection output is fluidically connected to (i) the feeding outlet and/or (ii) the bottom or top surface nearer the second wall end of the bioprocessing chamber than the first end wall.

In some embodiments, the solid support comprises a valve that regulates fluid flow from the bioprocessing chamber into the collection output. In some non-limiting embodiments, the solid support does not comprise a valve that regulates fluid flow from the bioprocessing chamber into the collection output.

In another aspect, the present disclosure provides a solid support, comprising: a bioprocessing chamber comprising a bottom surface; and a collection output fluidically connected to the bioprocessing chamber via the bottom surface, wherein the solid support comprises no valve that regulates fluid flow from the bioprocessing chamber into the collection output.

In some embodiments, the collection output is not orthogonal to the bottom or top surface. In some embodiments, the collection output is orthogonal to the bottom or top surface.

In another aspect, the present disclosure provides a solid support comprising a bioprocessing chamber comprising a ceiling; a feeding output channel fluidically connected to the bioprocessing chamber via the ceiling; and a filter that selectively prevents solid particles from passing from the bioprocessing chamber to the feeding output channel. In some embodiments, the filter comprises a filter membrane that comprises a hydrophilic material, optionally, wherein the hydrophilic material comprises polyethersulfone (PES), polycarbonate, or polyester. In some embodiments, the filter comprises a filter membrane that comprises a pore size of less than 10 µm, less than 7.5 µm, less than 5 µm, or less than 2.5 µm. In some embodiments, the filter comprises a filter membrane that is rectangular or circular.

In some embodiments, the solid support comprises a second feeding output channel. In some cases, the second feeding output cannel is separate from the first feeding output channel that is connected to the filter. In some cases, the second feeding output channel is located upstream or downstream of the first feeding output channel. In some embodiments, the second feeding output channel is closed while the first feeding output channel is used with a filter that prevents solids from the bioprocessing chamber from passing through the feeding output channel. In another embodiment, the first feeding output channel is closed while the second feeding output channel is open and used to allow fluids to exit during a perfusion run. In another embodiment, the second feeding output channel may also serve as the collection output when positioned at the top surface.

In some embodiments, the solid support further comprises a microfluidic feeding input channel. In some embodiments, the bioprocessing chamber is fluidically coupled to the microfluidic feeding input channel.

In some embodiments, a flow path comprising the microfluidic feeding input channel, the bioprocessing chamber, and the feeding output channel/s is/are closed.

In some embodiments, the bioprocessing chamber is elongated and comprises a first end wall and a second end wall opposite the first end wall. In some embodiments, the ceiling is substantially orthogonal to the first end wall and the second end wall. In some embodiments, the bioprocessing chamber comprises a fillet on a portion of the chamber. The portion of the chamber may be, for example, an upper perimeter of the chamber.

In some embodiments, the microfluidic feeding input channel is fluidically connected to the first end wall of the bioprocessing chamber and feeding output channel is fluidically connected to the ceiling nearer the second end wall of the bioprocessing chamber than the first end wall.

In another aspect, the present disclosure provides a solid support comprising a bioprocessing chamber comprising a bottom surface and a ceiling; a collection output fluidically connected to the bioprocessing chamber via the bottom or top surface; and a feeding output channel fluidically connected to the bioprocessing chamber via the ceiling.

In some embodiments, the collection output is positioned directly below the feeding output channel. In some embodiments, the collection output is not positioned directly below feeding output channel.

In some embodiments, the solid support further comprises a filter membrane that selectively prevents solid particles from passing from the bioprocessing chamber to the feeding output channel. In some embodiments, the solid support further comprises a feeding input channel, wherein the bioprocessing chamber is fluidically connected to the feeding input channel. In some embodiments, the feeding input channel is a single channel. In some embodiments, the feeding input channel comprises a plurality of feeding input channels. In some embodiments, the plurality of feeding input channels comprises a binary tree network.

In some embodiments, the solid support further comprises a feeding input fluidically connected to the feeding input channel. In some embodiments, the feeding input is one feeding input. In some embodiments, the feeding input comprises a plurality of feeding inputs. In some embodiments, the feeding input channel comprises a length dimension parallel to a length dimension of the bioprocessing chamber.

In some embodiments, the bottom surface is on a first plane, wherein the feeding input channel is on a second plane, wherein the first plane and the second plane are different, and the first plane is below the second plane. In some embodiments, a length dimension of the bioprocessing chamber is at least 2×, 3×, 4×, 5×, 10×, 15×, or 20× a width dimension of the bioprocessing chamber. In some embodiments, the bioprocessing chamber comprises a curved edge. In some embodiments, the curved edge is at an end or both ends of the bioprocessing chamber. In some embodiments, the bottom surface comprises a material that is classified as a United States Pharmacopeia (USP) Class VI material and is ISO 10993 compliant. In some embodiments, the bottom surface comprises cyclic olefin copolymer (COC). In some embodiments, the bioprocessing chamber comprises a wall. In some embodiments, the wall comprises cyclic olefin copolymer (COC). In some embodiments, the ceiling comprises a gas permeable material, optionally, wherein the gas permeable material is polydimethylsiloxane (PDMS), or a cyclic olefin copolymer (COC) membrane, optionally wherein the COC membrane has a thickness of about 100 μm. In some embodiments, the ceiling comprises any gas permeable polymer membrane. In some embodiments, the ceiling comprises COC. In some cases, the ceiling comprises a COC membrane having a thickness of about 100 micrometers. In some embodiments, the bioprocessing chamber comprises a height of at least 0.1 mm, 0.2 mm, 0.3 mm, 0.4 mm, 0.5 mm, 1.0 mm, 2.0 mm, 3.0 mm, 4.0 mm, or 5.0 mm. In some embodiments, the bioprocessing chamber is treated with a coating. In some embodiments, the coating interacts with or adheres to the bottom surface via curing or incubation.

In some embodiments, the solid support further comprises an additional feeding output channel fluidically connected to the bioprocessing chamber. In some embodiments, the additional feeding output channel is located upstream or downstream of the feeding output channel. In some embodiments, the additional feeding output channel is located adjacent or proximal to the feeding output channel. In some embodiments the additional feeding output channel is configured to close while the feeding output channel is used to receive a filtered flow from the bioprocessing chamber. In some embodiments, the feeding output channel is configured to close while the additional feeding output channel is open to allow fluids to exit through the additional feeding output channel during perfusion. In some embodiments, the ceiling comprises a permeable polymer membrane. In some embodiments, the ceiling comprises one or more fillets. In some embodiments, the bioprocessing chamber comprises one or more fillets configured to distribute pressure across a portion of the bioprocessing chamber to reduce a likelihood of fracture or deformation of the bioprocessing chamber. In some embodiments, the one or more fillets are located on an upper perimeter portion of the bioprocessing chamber. In some embodiments, the solid support further comprises a plurality of feeding output channels connected to the bioprocessing chamber via a ceiling of the bioprocessing chamber.

In another aspect, the present disclosure provides a system comprising any of the solid supports described herein. In some cases, the solid supports are coupled to an agitation device.

In another aspect, the present disclosure provides a method comprising: providing a solid support; and flowing a fluid through the microfluidic feeding input channel and the bioprocessing chamber. In some embodiments, the fluid comprises solid particles. In some embodiments, the method further comprises seeding the solid particles in the bioprocessing chamber, thereby providing seeded solid particles. In some embodiments, the method further comprises agitating the solid support to homogenously distribute the solid particles in the bioprocessing chamber. In some embodiments, the seeded solid particles comprise cells. In some embodiments, the method further comprises expanding the cells in the bioprocessing chamber. In some embodiments, the method further comprises harvesting the expanded cells through the collection output. In some embodiments, the harvesting comprises using positive pressure, negative pressure, or both In some embodiments, the harvesting comprises using positive pressure via the inlet channels, negative pressure via the harvesting channels, or both.

In another aspect, the present disclosure provides a method comprising: providing a solid support and flowing a fluid through the bioprocessing chamber and a feeding output channel. In some embodiments, the fluid comprises solid particles, and the solid particles comprise biological materials such as cells. In some embodiments, the filter membrane prevents the cells from entering the feeding output channel during seeding or perfusion. In some embodiments, the cells comprise human cells.

In another aspect, the present disclosure provides a method comprising: providing a solid support; and flowing a fluid through the bioprocessing chamber and the feeding output channel. In some embodiments, the fluid comprises solid particles. In some embodiments, the solid particles comprise cells. In some embodiments, the method further comprises seeding the cells in the bioprocessing chamber, thereby providing seeded cells. In some embodiments, during the flowing of the fluid, the cells do not enter the collection output or the feeding output channel. In some embodiments, the method further comprises contacting the seeded cells with a reagent. In some embodiments, the method further comprises mixing the seeded cells with a reagent.

In another aspect, the present disclosure provides a microfluidic system comprising one or more bioprocessing chambers, wherein the system is configured for i) culturing over 20,000 cells in the one or more bioprocessing chambers and ii) harvesting at least 90% of the cells to yield recovered cells, wherein at least 90% of the recovered cells are viable. In some embodiments, microfluidic system further comprises a feeding input channel, wherein the one or more bioprocessing chambers are fluidically connected to the feeding input channel.

In some embodiments, the microfluidic system further comprises one or more collection outputs fluidically connected to the one or more bioprocessing chambers. In some embodiments, the one or more collection outputs are fluidically connected to the one or more bioprocessing chambers via a bottom surface of the one or more bioprocessing chambers.

In some embodiments, the microfluidic system further comprises one or more filters that selectively prevent solid particles from passing from the one or more bioprocessing chambers to a feeding output channel of the microfluidic system.

In another aspect, the present disclosure provides a microfluidic system comprising one or more bioprocessing chambers, wherein the microfluidic system is configured for: i) culturing over 20,000 cells in the one or more bioprocessing chambers, ii) at greater than 90% cell seeding efficiency in under 5 minutes. In some embodiments the microfluidic system further comprises a feeding input channel, wherein the one or more bioprocessing chambers are fluidically connected to the feeding input channel. In some embodiments, the microfluidic system further comprises one or more collection outputs fluidically connected to the one or more bioprocessing chambers. In some embodiments, the one or more collection outputs are fluidically connected to the one or more bioprocessing chambers via a bottom surface of the one or more bioprocessing chambers. In some embodiments, the microfluidic system further comprises one or more filters that selectively prevent solid particles from passing from the one or more bioprocessing chambers to a feeding output channel of the microfluidic system.

In another aspect, the present disclosure provides a microfluidic system comprising one or more bioprocessing chambers, wherein the system is configured for homogenous cell distribution of at least 20,000 cells in the one or more bioprocessing chambers. In some embodiments, the microfluidic system further comprises a feeding input channel, wherein the one or more bioprocessing chambers are fluidically connected to the feeding input channel. In some embodiments, the microfluidic system further comprises one or more collection outputs fluidically connected to the one or more bioprocessing chambers. In some embodiments, the one or more collection outputs are fluidically connected to the one or more bioprocessing chambers via a bottom surface of the one or more bioprocessing chambers. In some embodiments, the microfluidic system further comprises one or more filters that selectively prevent solid particles from passing from the one or more bioprocessing chambers to a feeding output channel of the microfluidic system.

In another aspect, the present disclosure provides a solid support comprising: a bioprocessing chamber comprising a bottom surface for culturing cells and a ceiling for enclosing at least a portion of the bioprocessing chamber to form a bioprocessing region; a collection output configured for harvesting at least one cell cultured in the bioprocessing chamber, wherein the collection output is fluidically connected to the bioprocessing chamber via the ceiling or the bottom surface of the bioprocessing chamber; a feeding output channel fluidically connected to the bioprocessing chamber via the ceiling, wherein the feeding output channel is configured to receive a flow of a fluid from the bioprocessing chamber; and a flow path for directing the fluid along a streamline from a feeding input channel of the solid support through the bioprocessing chamber to the feeding output channel, wherein the flow path is configured to reduce or minimize (i) a turbulent flow of the fluid and (ii) a shear stress on at least one cell cultured in the bioprocessing chamber. In some embodiments, the solid support further comprises a filter configured to selectively prevent a passage of solid particles from the bioprocessing chamber to the feeding output channel. In some embodiments, the filter is positioned within the feeding output channel or upstream of the feeding output channel. In some embodiments, the filter comprises a filter membrane that comprises a pore size of less than 10 µm, less than 7.5 µm, less than 5 µm, or less than 2.5 µm. In some embodiments, the solid support further comprises a plurality of feeding input channels comprising the feeding input channel, wherein the plurality of feeding input channels is fluidically coupled to the bioprocessing chamber. In some embodiments, the plurality of feeding input channels comprises or form a binary tree network. In some embodiments, the feeding input channel is located on a first plane, and wherein the bottom surface of the bioprocessing chamber is located on a second plane that is different than the first plane. In some embodiments, the second plane is below the first plane. In some embodiments, the collection output is located on a third plane that is below the second plane or above the first plane. In some embodiments, the solid support further comprises an additional feeding output channel fluidically connected to the bioprocessing chamber. In some embodiments, the additional feeding output channel is a collection output. In some embodiments, the additional feeding output channel is located upstream or downstream of the feeding output channel. In some embodiments, the additional feeding output channel is located adjacent or proximal to the main feeding output channel. In some embodiments, the additional feeding output channel is configured to close while the feeding output channel is used to receive the flow from the bioprocessing chamber. In some embodiments, the bioprocessing chamber comprises a rounded or curved edge or surface. In some embodiments, the bioprocessing chamber comprises a fillet configured to distribute pressure due to fluid flow across a portion of the bioprocessing chamber. In some embodiments, the fillet is configured to reduce or minimize a likelihood of fracture or deformation of the bioprocessing chamber due to the fluid flow. In some embodiments, the fillet is located on an upper perimeter portion of the bioprocessing chamber. In some embodiments, the flow path comprises a first flow path between the feeding input channel and the feeding output channel for transporting the fluid or cell medium. In some embodiments, the flow path comprises a second flow path for harvesting the at least one cell through the collection output. In some embodiments, the first flow path and the second flow path extend along a same direction. In some embodiments, the first flow path and the second flow path at least partially coincide. In some embodiments, the bioprocessing region is configured for cell seeding, media perfusion, cell washing, cell expansion, cell culturing, and cell harvesting without requiring a transport of cultured cells to different chambers or to an external chamber. In some embodiments, the solid support is configured for i) culturing over 20,000 cells in the bioprocessing chamber and ii) harvesting at least 90% of the cells to yield recovered cells, wherein at least 90% of the recovered cells are viable. In some embodiments, the microfluidic system is configured for: i) seeding over 20,000 cells in the bioprocessing chamber, ii) at greater than 90% cell retention efficiency, (iii) in under 5 minutes. In some embodiments, the bioprocessing chamber is elongated and comprises a first end wall and a second end wall opposite the first end wall, and wherein the ceiling of the bioprocessing chamber is substantially orthogonal to the first end wall and the second end wall. In some embodiments, the feeding input channel is fluidically connected to the first end wall of the bioprocessing chamber and feeding output channel is fluidically connected to the ceiling nearer the second wall end of the bioprocessing chamber than the first end wall. In some embodiments, a length dimension of the bioprocessing chamber is at most about 60 cm, wherein a width dimension of the bioprocessing chamber is at most about 10 cm, and wherein a height dimension of the bioprocessing chamber is at most about 5 mm. In some embodiments, the bioprocessing chamber is treated with a coating, wherein the coating interacts with or adheres to the bottom surface via curing or incubation. In some embodiments, the cells comprise human cells.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 5A-5C schematically illustrate an exemplary chip and components thereof, in accordance with some embodiments.

FIGS. 8 and 9 show enhanced cell transduction over time.

FIG. 10 shows a plot of fluorescence (object count) tracking transduced cells over time.

FIG. 21 schematically illustrates a series of images of a chip before, during, and after a harvesting procedure, in accordance with some embodiments.

FIGS. 24 and 25 schematically illustrate various components of an exemplary chip as viewed from multiple perspectives, in accordance with some embodiments.

DETAILED DESCRIPTION

Figure 1A:
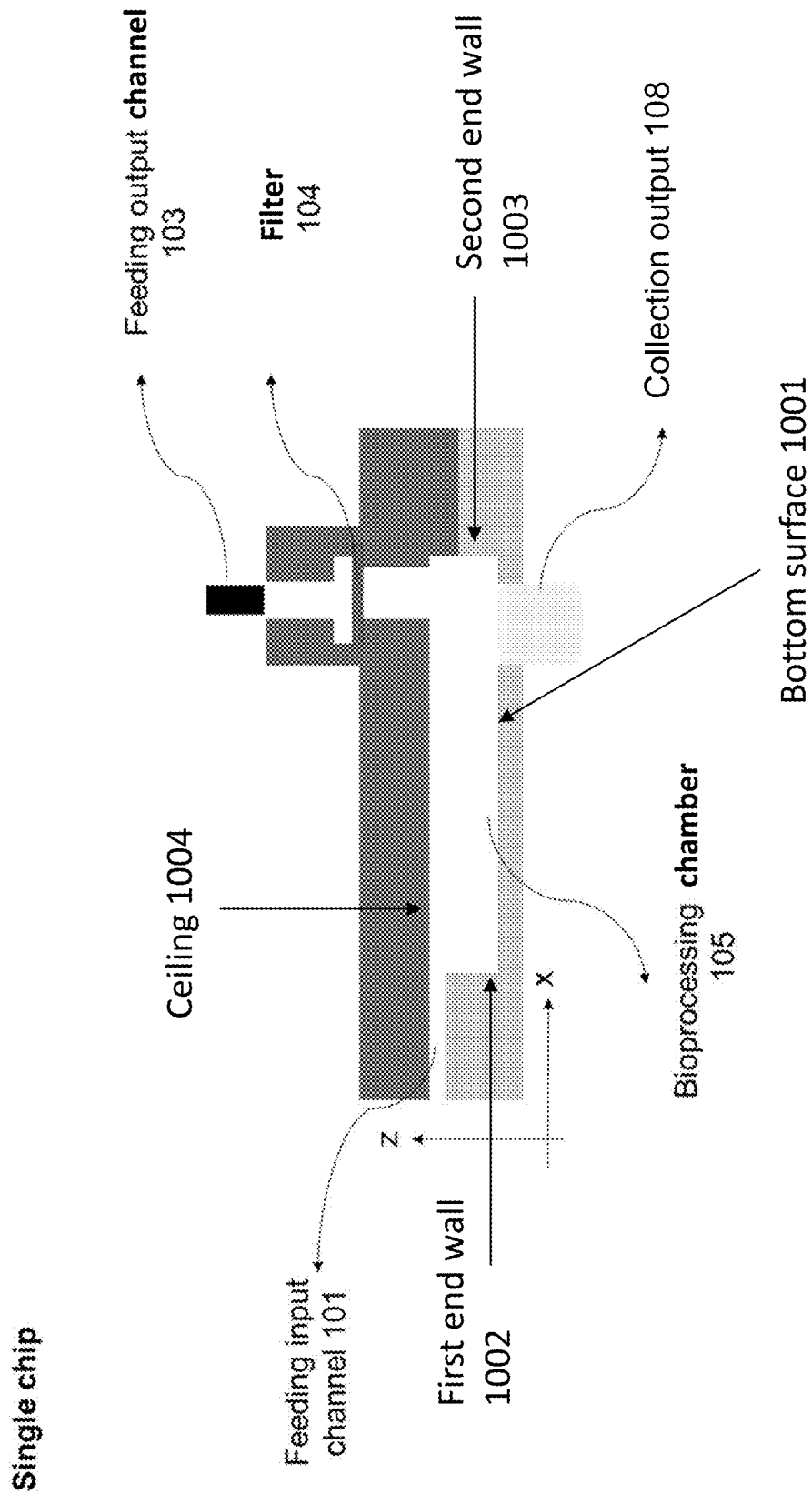
FIG. 1A-1D schematically illustrates single chip designs in accordance with some embodiments.

While various embodiments have been shown and described herein, it will be obvious to those skilled in the art that such embodiments are provided by way of example only. Numerous variations, changes, and substitutions can occur to those skilled in the art without departing from the disclosure. It should be understood that various alternatives to the embodiments described herein can be employed.

Whenever the term "about," "at least," "greater than," or "greater than or equal to" precedes the first numerical value in a series of two or more numerical values, the term "about," "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, mL can refer to milliliter(s) as a unit of measurement for volume or displacement, mm can refer to millimeter(s) as a unit of measurement for distance, cm can refer to centimeter(s) as a unit of measurement for distance, μm can refer to micrometer(s) as a unit of measurement for distance, nm can refer to nanometer(s) as a unit of measurement for distance, and h can refer to hour(s) as a unit of measurement for time.

The terms "collect" and "harvest" are used interchangeably herein.

Overview

The present disclosure provides a multifunctional microfluidic-based system that permits streamlined non-invasive in situ bioprocessing operations for adherent and suspension cells. The system can comprise one or more microfluidic chips (solid supports) as described in further detail below.

The one or more microfluidic chips (solid supports) can be designed to optimize the operations involved in cell production for cell therapy applications. These operations aimed for cell production can include, for example, seeding, treatment, proliferation and/or differentiation, washing and/or purification, sampling, and harvesting—all of which can be performed within the bioprocessing chamber (e.g., on a culture surface or within a volume of the bioprocessing chamber) of the microfluidic chip (solid support) without the need of external transplants and/or invasive interventions.

Cell Therapy

The systems and methods of the present disclosure can be used for cell therapy applications. Cell therapy can be a treatment approach in which functional and healthy cells are administered into or to a subject (e.g., a patient).

The systems of the present disclosure are designed to improve the cell culture process. In one aspect, the present disclosure provides a chip comprising a bioprocessing chamber that is capable of performing bioprocessing operations involved in cell culture. The chip can utilize microfluidics, which can involve manipulating fluids inside channel dimensions of the micrometer range. In some embodiments, the channels described herein (including, for instance, feeding input channels, feeding output channels, input harvest channels, output harvest channels, etc.) can have one or more channel dimensions. The one or more channel dimensions can correspond to one or more of a channel width, a channel length, a channel height, or a channel diameter. The channel dimensions can range from about 1 μm to about 10 cm. In some cases, the channel dimensions can be less than 1 μm. In some cases, the channel dimensions can be greater than 10 cm. In some cases, the channels described herein (including, for instance, feeding input channels, feeding output channels, input harvest channels, output harvest channels, etc.) can have a channel volume. The channel volume can range from 10% of the total chip volume to 90% of the total chip volume. The total chip volume can correspond to the combined internal volume of at least the enclosed channels and the bioprocessing chamber(s) of the chip. In some cases, the channel volume can be less than 10% of the total chip volume. In some cases, the channel volume can be greater than 90% of the total chip volume.

Microfluidic cell culture can provide several advantages, including, for instance: (1) better control of process parameters than other cell culture methods: cells can have equal access to molecules present in the surrounding fluid due to homogenous cell distribution and fluid circulation in microenvironments, which can result in a more homogeneous end product and less process failure (e.g. cell death); (2) better overall cell health: e.g., paracrine effects can be amplified in a small environment (i.e., microscale), which can lead to better cell expansion and phenotype control; (3) a reduction in reactant volume: can be 10-20 fold reduction compared to other conventional microfluidic systems, due to smaller volumes of fluid used in microfluidic chips as well as the ability to recirculate unspent reagent (e.g., growth media (fluid) can be re-enriched and recirculated at defined intervals, e.g., due to rapid oxygen or glucose depletion inside the chip). As used herein, homogenous cell distribution may refer to the distribution of cells such that a density of cells is approximately uniform across a target area. In some cases, a homogenous cell distribution comprises a distribution of cells on a surface of the bioprocessing chamber that is approximately even throughout the length and the width of the chamber such that the cells are spaced apart by a similar or approximately same distance relative to each other. In some non-limiting examples, the distance between the cells is on the order of nanometers to micrometers.

Chip

FIG. 1A-1D schematically illustrate exemplary chips. A chip can be a support or a solid support comprising a bioprocessing chamber, e.g., one bioprocessing chamber. The chip can comprise a feeding input that connects to one or more feeding input channels 101. The feeding input can comprise a single hole or a plurality of holes. The plurality of holes can provide separate inputs for seeding, perfusion, washing, and/or harvesting. In some cases, the feeding input comprises an input for adding or supplying one or more reagents. In some cases, the input is used for a plurality of functions, including, for example, seeding, perfusion, washing, harvesting, and/or the provisioning of one or more reagents. In other cases, multiple discrete inputs are used for different functions (i.e., different inputs are used for seeding, perfusion, washing, harvesting, and/or the provisioning of one or more reagents). These feeding input channels can be used for seeding and perfusion. The input channels 101 can take several forms. It can be a single channel or a plurality of channels in the form of a standard or modified binary tree network.

These input channels 101 can feed into a bioprocessing chamber 105, which can comprise a recess in fluidic communication with the one or more feeding input channels 101. The recess can comprise a vertical depth perpendicular to the flow direction where cells can settle. The recess can be protected from damaging shear stress because of minimal fluid velocity acting on the recess. In some cases, the vertical depth of the recess ranges from about 1 mm to about 1 cm. In some cases, the vertical depth of the recess is greater than about 1 cm. In some cases, a length of the bioprocessing chamber is about, at least, or at most 1.5, 2, 3, 4, 5, 6, 7, 8, 9, 10, 20, 30, 40, 50, or 60 times the vertical depth of the recess. The bioprocessing chamber 105 can be elongated in the primary direction of seeding and perfusion flow, such that the length of the bioprocessing chamber is much greater than the width of the bioprocessing chamber. In some cases, the microfluidic chip or the bioprocessing chamber of the microfluidic chip can have a length that is about, at least, or at most 1.5, 2, 3, 4, 5, 6, 7, 8, 9, 10, 20, 30, 40, 50, or 60 times its width. In some embodiments, the edges of the bioprocessing chamber 105 (e.g., at the ends) can be curved to minimize culture dead zones, for example as shown in FIG. 4B. Having curved edges can also facilitate initial chip wetting as opposed to sharp edges.

In some cases, the microfluidic chip or the bioprocessing chamber of the microfluidic chip comprises a fillet at an interface between the ceiling and the perimeter wall or the bottom surface and the perimeter wall or both. In some cases, the fillet comprises a curved or rounded surface between two surfaces or portions of the bioprocessing chamber. In some cases, the fillet is configured to provide a transitional surface between two surfaces or portions of the bioprocessing chamber.

In some cases, the bioprocessing chamber can comprise a recess with one or more walls that are angled relative to the feeding input channels and/or the feeding output channels. In some non-limiting embodiments, the angle can range from about 45 degrees to about 90 degrees. In some cases, the bioprocessing chamber can have one or more dimensions. The one or more dimensions can comprise, for example, a length, a width, a height, or a depth. The one or more dimensions of the bioprocessing chamber can range from about 1 mm to about 60 cm. In some cases, the dimensions of the bioprocessing chamber can be less than 1 mm. In some cases, the dimensions of the bioprocessing chamber can be greater than about 60 cm. The bioprocessing chamber can comprise a volume of less than 10 mL, 7 mL, 5 mL, 4 mL, 3 mL, 2 mL, 1 mL, or 0.5 mL.

In some cases, the bioprocessing chamber can have a bottom surface, as described elsewhere herein. The bottom surface can be used for cell culturing. The bottom surface can have a surface area ranging from about 1 mm$^2$ to about 300 cm$^2$. In some cases, the surface area can be less than 1 mm$^2$. In some cases, the surface area can be greater than about 300 cm$^2$. The bottom surface can have a surface area of less than 300 cm$^2$, 200 cm$^2$, 100 cm$^2$, 90 cm$^2$, 80 cm$^2$, 70 cm$^2$, 60 cm$^2$, 50 cm$^2$, 40 cm$^2$, 30 cm$^2$, 20 cm$^2$, 10 cm$^2$, 6 cm$^2$, 5 cm$^2$, or 1 cm$^2$.

In some cases, a length dimension of the bioprocessing chamber can be at least 2×, 3×, 4×, 5×, 10×, 15×, or 20× a width dimension of the bioprocessing chamber. In some cases, the bioprocessing chamber has a height of at least 0.1 mm, 0.2 mm, 0.3 mm, 0.4 mm, or 0.5 mm.

The bioprocessing chamber top and front faces can comprise a cross-sectional shape. The cross-sectional shape can be a circle, an oval, an ellipse, a triangle, a square, a rectangle, or any other polygon having three or more sides. The cross-sectional shape can correspond to a horizontal cross-section and/or a vertical cross-section of the bioprocessing chamber.

Towards the downstream end of the bioprocessing chamber 105, there can be at least one outlet positioned above or below the bioprocessing chamber 105. In some embodiments, two outlets can be positioned above and/or below the bioprocessing chamber 105. In some embodiments, at least 2, 3, 4, 5, 6, 7, 8, 9, 10, or more outlets are positioned above and/or below the bioprocessing chamber 105. The upper outlet can connect to a filter 104 (e.g., a filter membrane) and/or a feeding output channel 103. In some cases, the chip may comprise a plurality of upper outlets connected to one or more filters. The one or more filters may be positioned at or near one or more upper outlets. In some cases, the one or more filters may be positioned in front of or within the one or more upper outlets. In some cases, the chip may comprise a plurality of filters that are stacked on top of each other, or arranged side-by side or in series relative to each other. The plurality of filters may have different shapes, composition, sizes, and/or filtering capabilities. In some cases, one or more filters may be provided in each of a plurality of upper outlets. The filter 104 can serve as a barrier to prevent cells from exiting the chamber prematurely, hence increasing seeding efficiency. During perfusion via the feeding input channel, while growth medium can be replenished (e.g., gradually replenished by a fresh batch of fluid) the cells can still be retained in the bioprocessing chamber 105 while the fluid exits through the feeding output channel 103. In some cases, the filter 104 can comprise a filter membrane, and the filter membrane can comprise a hydrophilic material, e.g. polyethersulfone (PES with a pore size structure of about 5 µm. In some cases, the filter 104 comprises a pore size of less than 10 µm, less than 7.5 µm, less than 5 µm, or less than 2.5 µm. The shape of the filter can be rectangular, oval, elliptical, or circular. In some cases, the shape can comprise any regular or irregular shape. In some cases, the shape can comprise any shape having three or more sides. In some cases, a dimension of the filter can range from about 1 µm to about 1 cm. The dimension can correspond to a length, a width, or a thickness of the filter. The lower outlet of the chip can be fluidically connected to a collection output 108 for harvesting or collection purposes. The collection output may be a collection drain. In some cases, the chip may comprise a plurality of collection drains disposed at or near a bottom surface of the bioprocessing chamber. In some cases, the chip may comprise a plurality of lower outlets fluidically connected to the plurality of collection outputs. In some cases, the plurality of lower outlets comprises at least 2, 3, 4, 5, 6, 7, 8, 9, 10, or more lower outlets fluidically connected to the plurality of collection outputs. When the collection drain is open, fluid containing cells can be drawn out of the bioprocessing chamber 105. To improve harvest efficiency, fluid can be pulled via the lower outlet, e.g., via a syringe pump or a suction generated by a negative pressure. Alternatively, fluid can be introduced via the feeding input and/or feeding output to help "push" the fluid out. Alternatively, collecting can also be done via a combination of push and pull actions, where fluid is simultaneously pulled from the lower outlet and pushed via the feeding input and/or output. The collection output 108 can be positioned directly below the filter 104 or at a position away from the filter 104. In some non-limiting embodiments, an inclined/sloped structure can be provided to facilitate the exit of the fluid. In some cases, the inclined/sloped structure can be integrated with the bottom surface of the bioprocessing chamber 105 and can connect the bioprocessing chamber 105 to the collection output 108. Alternatively, the inclined/sloped structure can be formed as part of the collection output 108. In some cases, the collection output may be positioned at or near a bottom portion of one or more walls of the bioprocessing chamber. In some cases, the collection output may be located upstream of a feeding output and/or downstream of a feeding input. In some cases, the collection output may be positioned to the left of the feeding input or feeding output. In other cases, the collection output may be positioned to the right of the feeding input or feeding output.

In some embodiments, the chip comprises a second feeding output channel. The fluid may exit through this second feeding output channel. The chips may have various arrangements of collection output 108 and second feeding output channels. FIG. 1B-1D shows examples of chips with different arrangements of collection outputs and second feeding output channels. FIG. 1B shows a chip with a collection output 108 positioned at a bottom surface of a chip, and a second feeding output positioned at a ceiling or top surface of the chip. FIG. 1C shows a chip with a collection output 108 positioned a ceiling or top surface of the chip, where the second feeding output is the same as the collection output. FIG. 1D shows a chip with a collection output positioned at a second end of the chip, and the second output feeding channel at positioned at a ceiling or top surface of a chip.

In some embodiments, the filter can comprise a pore size which can range from about 1 nm to about 1 mm. In some cases, the filter can comprise a plurality of different pore sizes ranging from about 1 nm to about 1 mm.

In some cases, the filter can comprise a membrane. The membrane can be permeable or semi-permeable. The membrane can comprise, for example, polytetrafluoroethylene (PTFE) or expanded polytetrafluoroethylene (ePTFE), polyethersulfone (PES), modified polyethersulfone (mPES), polysulfone (PS), modified polysulfone (mPS), ceramics, polypropylene (PP), cellulose, regenerated cellulose or a cellulose derivative (e.g. cellulose acetate or combinations thereof), polyolefin, polypropylene, polytetrafluoroethylene, polyvinyl chloride, polyester, or any other type of polymer.

In some non-limiting embodiments, the membrane can comprise a biomedical polymer, e.g., polyurethane, polyethylene, polypropylene, polyester, poly tetra fluoro-ethylene, polyamides, polycarbonate, or polyethylene-terephthalate.

Figure 1B:
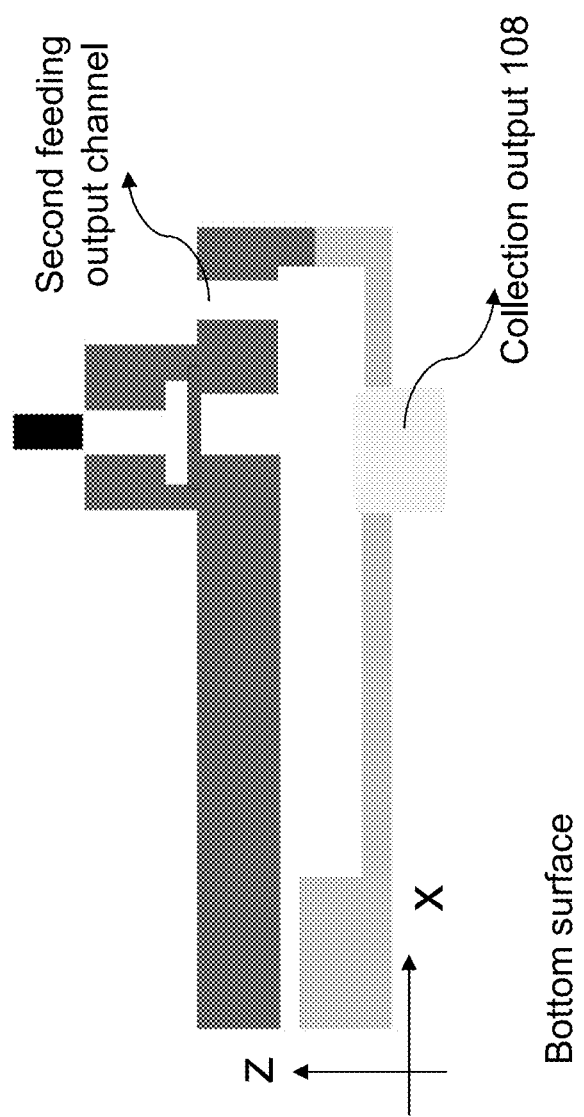
Figure 1C:
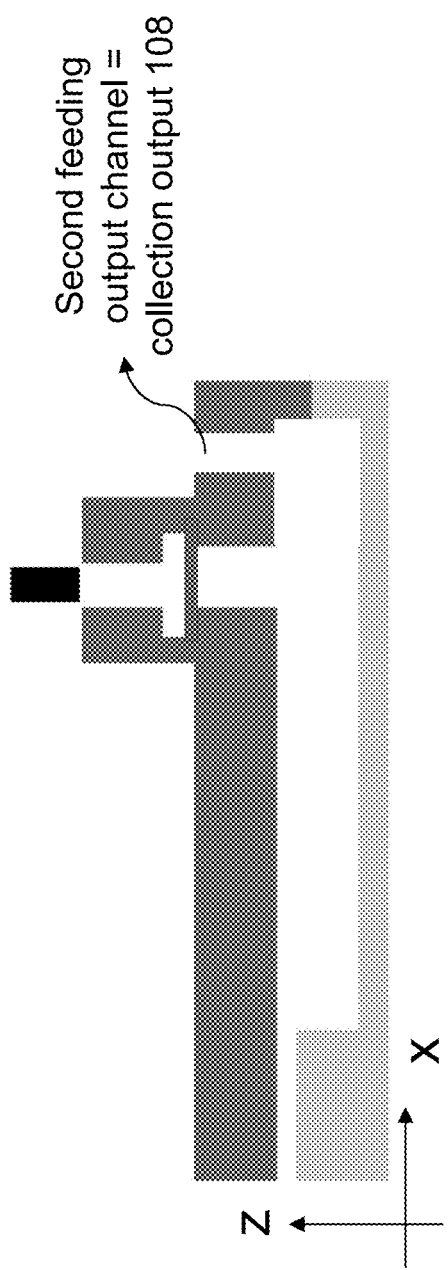
Figure 1D:
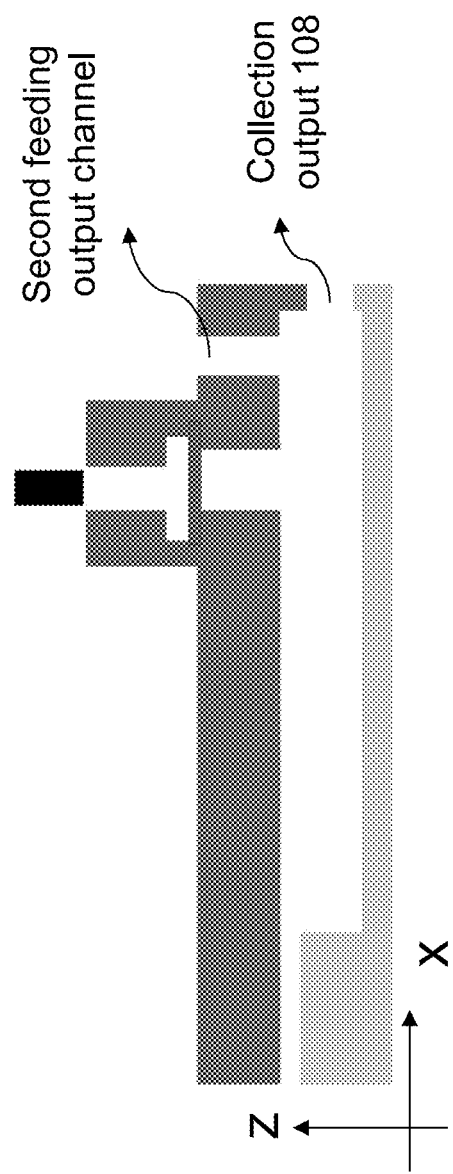
Figure 2:
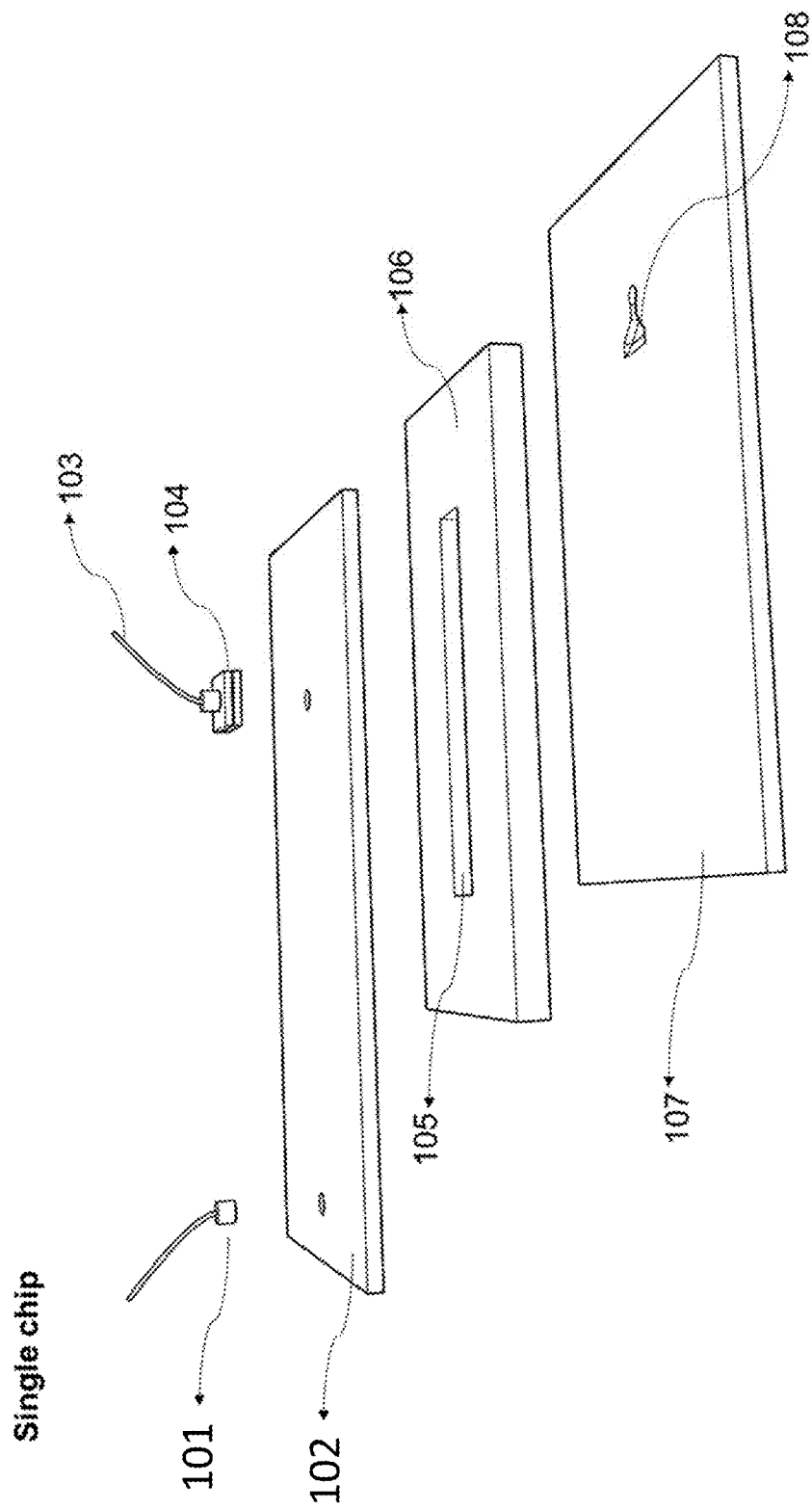
FIG. 2 schematically illustrates an exploded view of a single chip design, in accordance with some embodiments.

FIG. 2 schematically illustrates an exploded view of the components and layers of the exemplary chip shown in FIG. 1A. The chip can comprise one or more feeding input channels 101. The chip can further comprise an upper layer 102 with an aperture for receiving one or more materials (e.g., cells) transported through the one or more feeding input channels 101. The chip can further comprise one or more feeding output channel 103 and a filter 104.

In some embodiments, the chip can comprise a middle layer 106 comprising a bioprocessing chamber 105 that is carved out of the middle layer 106. In some embodiments, the chip can further comprise a bottom layer 107. The bottom layer can comprise a collection/harvest output 108. In one embodiment, the collection output 108 can comprise a circular structure. In some cases, the collection output (e.g., collection drain) may have a cross-sectional shape that is circular, oval, elliptical, square, or rectangular. In some cases, the collection output (e.g., collection drain) may have a cross-sectional shape having three or more sides. The cross-sectional shape may correspond to a regular shape or an irregular shape. In some cases, the bottom layer 107 can have an inclined or sloped structure leading to the collection output 108 to help facilitate the exit of the fluid. In other cases, the inclined or sloped structure can be formed as part of the collection output 108 to help facilitate the exit of the fluid. In some embodiments, the collection output 108 can be fluidically connected to the bioprocessing chamber via the bottom surface of the bioprocessing chamber. In some cases, the collection output 108 may be fluidically connected to the bioprocessing chamber via one or more holes, apertures, channels, or passageways in or through at least a portion of the bottom surface of the bioprocessing chamber.

The cells described herein can comprise a range of sizes. In some cases, the cells can have a size of at least about 1 micrometer, 5 μm, 10 μm, 20 μm, 30 μm, 40 μm, 50 μm, 60 μm, 70 μm, 80 μm, 90 μm, 100 μm, or any size that is between any two of the preceding values. In some cases, the cells can have a size that is less than about 1 μm. In some cases, the cells can have a size that is at most about 1 μm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, or less.

Materials

This microfluidic device can be fabricated in optically transparent material or a combination of different types of materials. The bioprocessing chamber that can be used for cell culture can be made of a USP Class VI Material. Such materials can be transparent so that imaging technology can be coupled. The device can also possess tolerances on the design requirements (e.g. channels) not lower than 5 μm in absolute value for the smallest feature and 5% for larger dimensions. This can ensure that fabrication of these devices can be suitable with standard manufacturing processes (e.g. sheet or roll processing). The device can also comprise usable surface culture space (for the individual chip) that is potentially capable of handling up to at least about 10 million cells, 20 million cells, 30 million cells, 40 million cells, 50 million cells, 60 million cells, 70 million cells, 80 million cells, 90 million cells, 100 million cells, or more.

The device can have certain favorable properties. For example, the device can favor homogenous distribution or collection of solids (i.e., cells) and prevent premature collection of seeded cells. In some embodiments, seeding efficiency (i.e., the number of cells trapped or retained relative to the number of cells initially injected) can be greater than about 90%, 91%, 92%, 93%, 94%, 95%, 96%, 97%, 98%, or 99%. The device can also be versatile for adherent and suspension solids (i.e., cell culture). The fluid flow coming from perfusion can avoid generating high shear stress that would potentially damage the cells. For suspension cells, the flow can circulate and exit the chip without flushing the cells. The device can also favor cell growth with minimal invasion and favor sampling procedures without invasive procedures. In some cases, the device can favor cell/particle extraction from the device at >90% efficiency with very minimal cells still stuck in the system. In some cases, the device can favor cell/particle extraction from the device at about 50%, 60%, 70%, 80%, 90%, or 99% efficiency with very minimal cells still stuck in the system.

The chip can possess usable surface culture area of at least about 1 cm$^2$, which can represent at least about 70% of the total chip footprint.

FIG. 2 schematically illustrates multiple layers of a chip. The chip can comprise an upper layer 102. The chip can further comprise a middle layer 106 comprising a bioprocessing chamber 105. The bioprocessing chamber 105 can be carved out of the middle layer 106 of the chip. The chip can further comprise a bottom layer 107. The bottom layer 107 can comprise or can be in fluidic communication with a collection output 108. As described elsewhere herein, in some cases the bottom layer 107 can have an inclined or sloped structure leading to the collection output 108 to help facilitate the exit of the fluid. In other cases, the inclined or sloped structure can be formed as part of the collection output 108 to help facilitate the exit of the fluid.

In some cases, the upper layer 102 of the chip can interface with one or more feeding input channels at one end and one or more feeding output channels 103 at another end. In some cases, one or more filters 104 can be placed upstream of the one or more feeding output channels 103.

Figure 3:
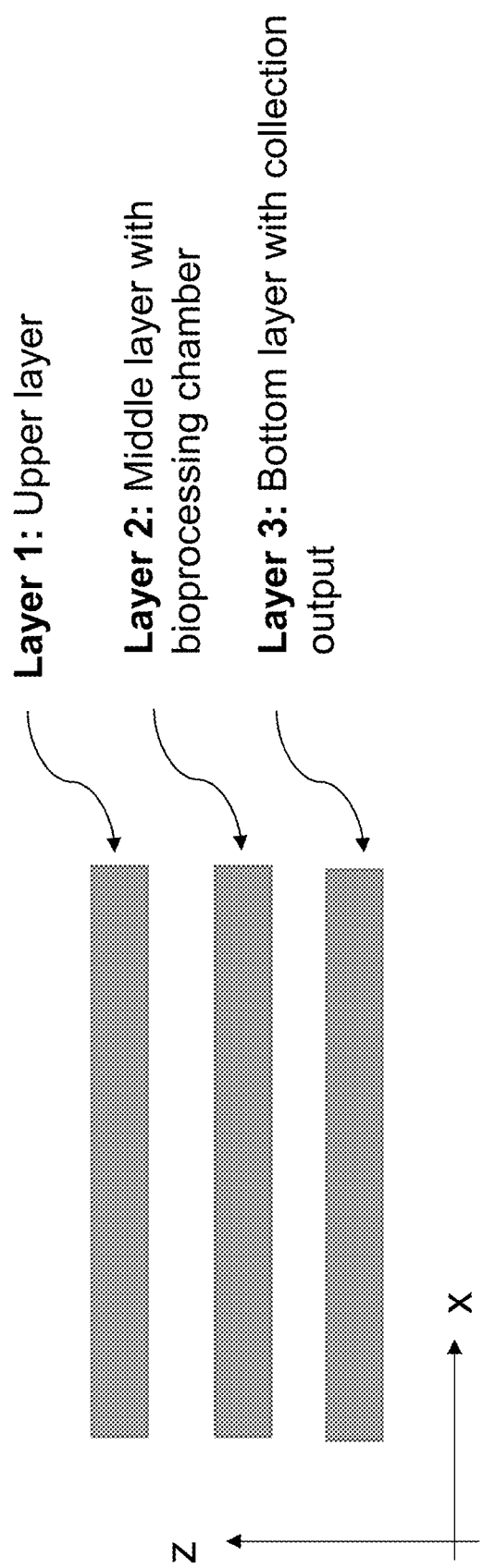
FIG. 3 schematically illustrates various layers of a chip, in accordance with some embodiments.

FIG. 3 shows a schematic for an exemplary chip that comprises 3 layers. The three layer may comprise different components that interface with components in other layers. Layer 1 is an upper layer and may be an upper layer as described in FIG. 2 such as upper layer 102. Layer 2 is an middle layer comprising a bioprocessing chamber and may be an middle layer as described in FIG. 2 such as middle layer 106. Layer 3 is a bottom layer comprising a collection output and may be an bottom layer as described in FIG. 2 such as bottom layer 107.

Figure 4A:
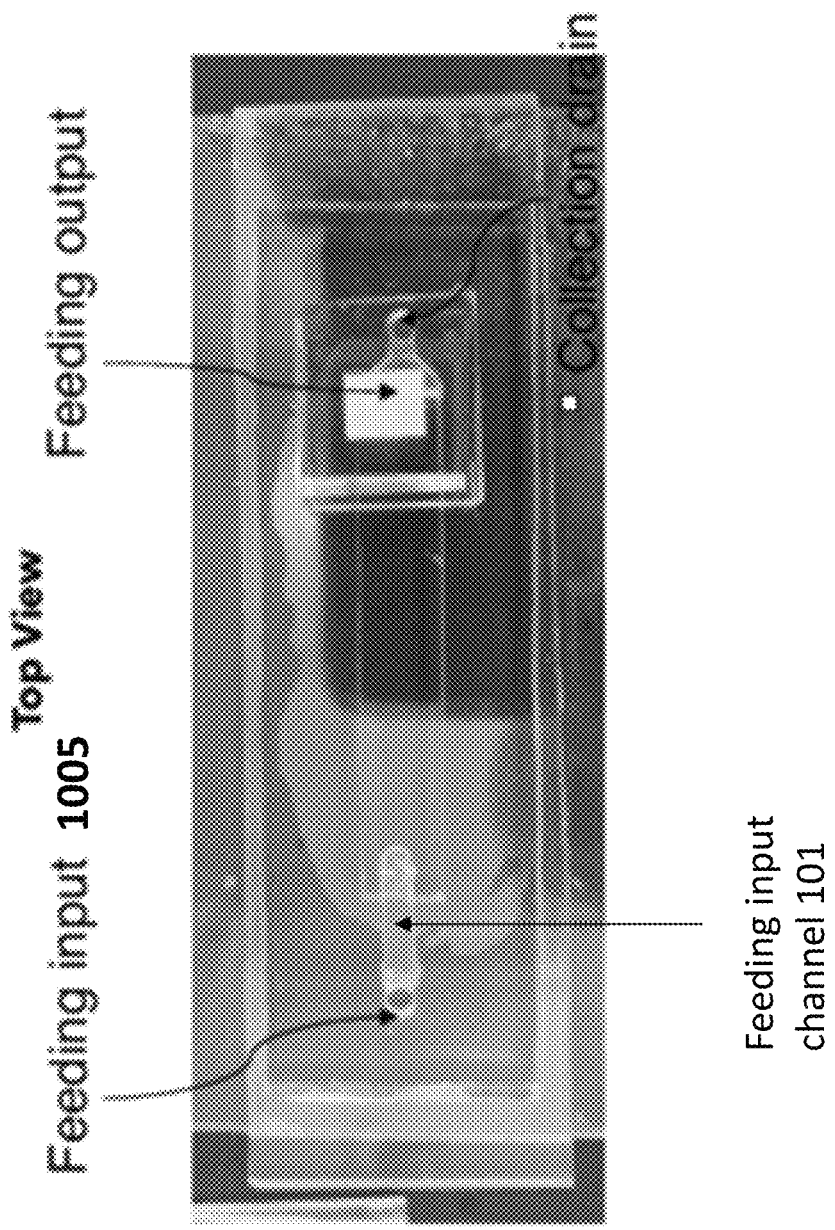
FIGS. 4A, 4B and 4C schematically illustrate a top view of a chip, in accordance with some embodiments.
Figure 4B:
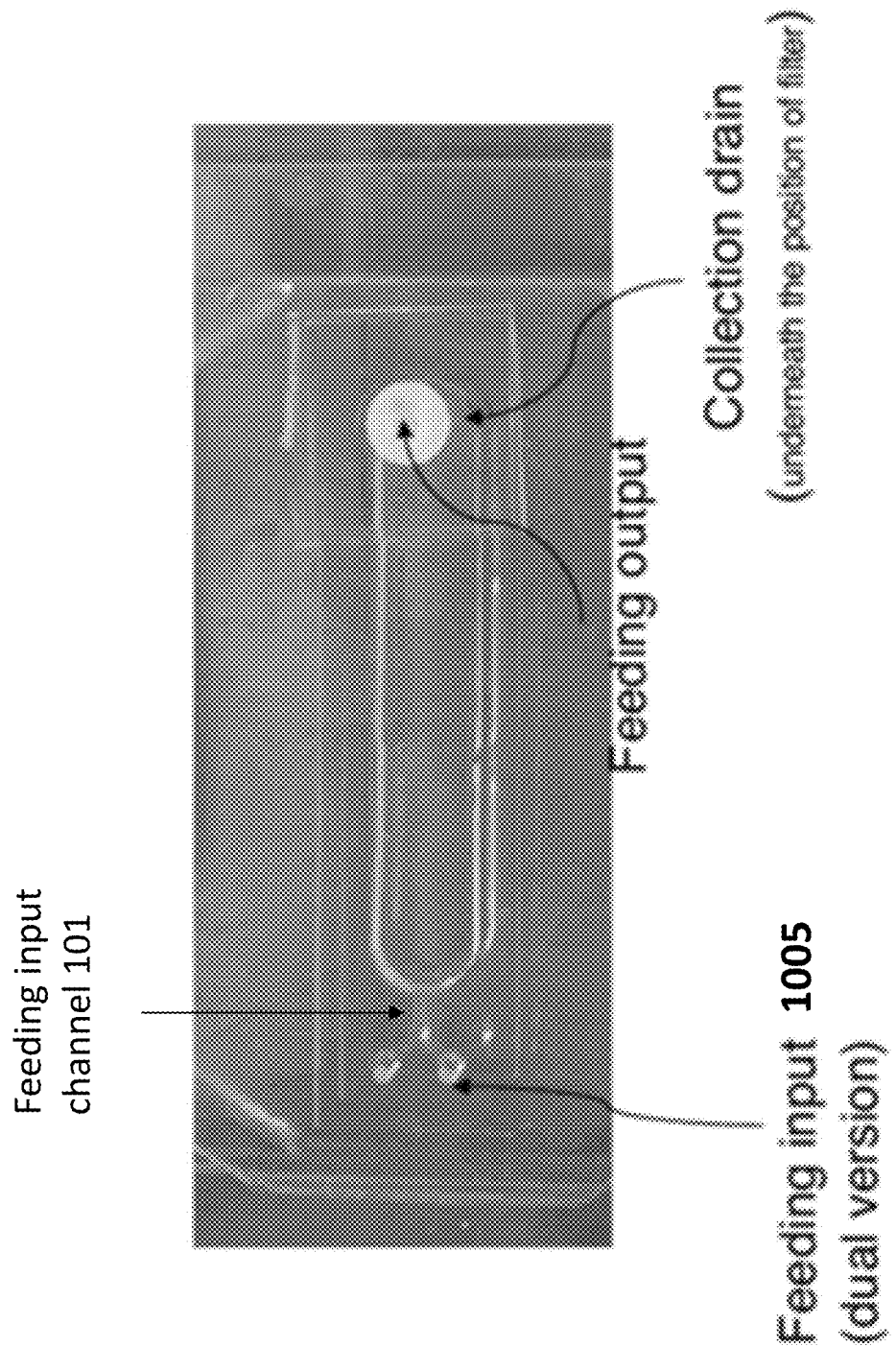
Figure 4C:
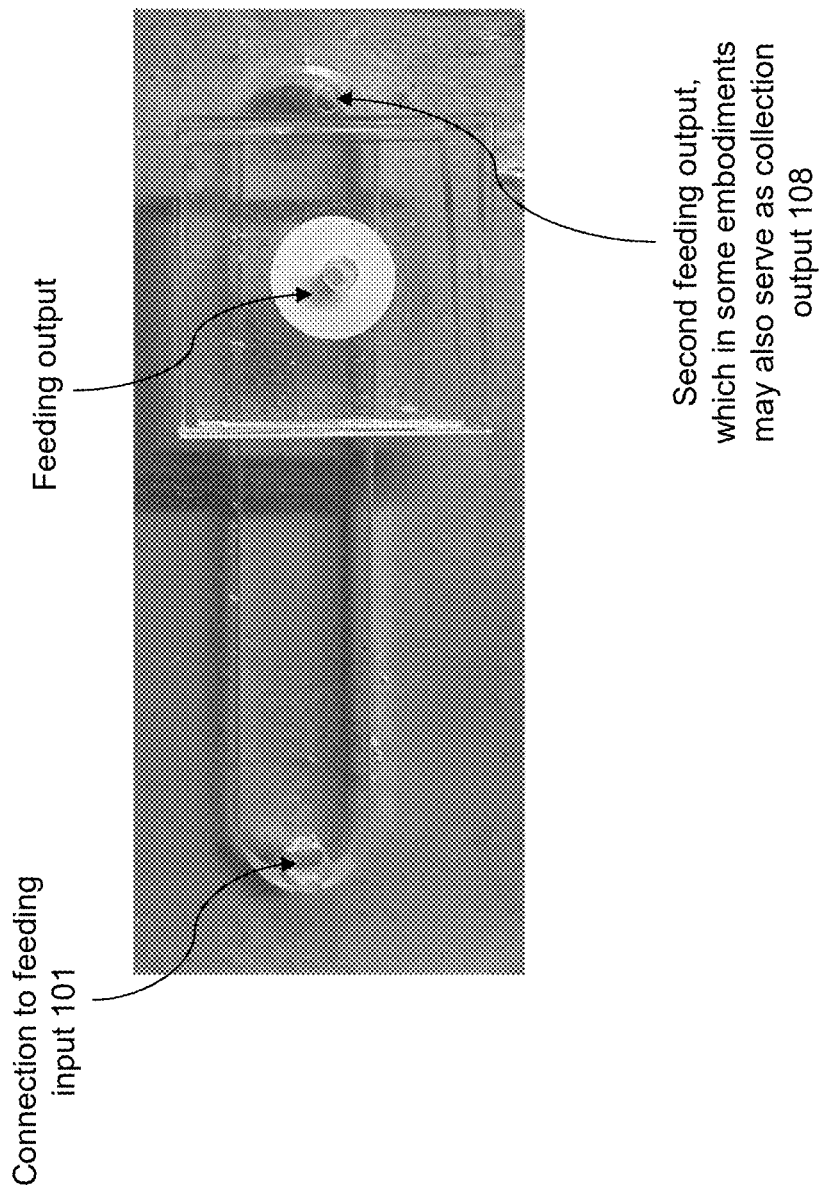

FIGS. 4A, 4B, and 4C schematically illustrate a top view of a chip. The chip can comprise one or more feeding inputs 1005 in a first portion of the chip and one or more feeding outputs on a second portion of the chip. The one or more feeding inputs 1005 can be in fluidic communication with one or more feeding input channels 101 as described elsewhere herein. The chip can further comprise a collection output. The collection output can be located underneath a filter of the chip. The feeding outputs may also serve as a collection output, for example, as shown in FIG. 4C. The filter can be placed proximal to the one or more feeding outputs to prevent the movement or passage of cells through the feeding outputs. In some cases, the feeding outputs can comprise one or more feeding output channels as described elsewhere herein. In other cases, the feeding outputs can be in fluidic communication with one or more feeding output channels.

Figure 4D:
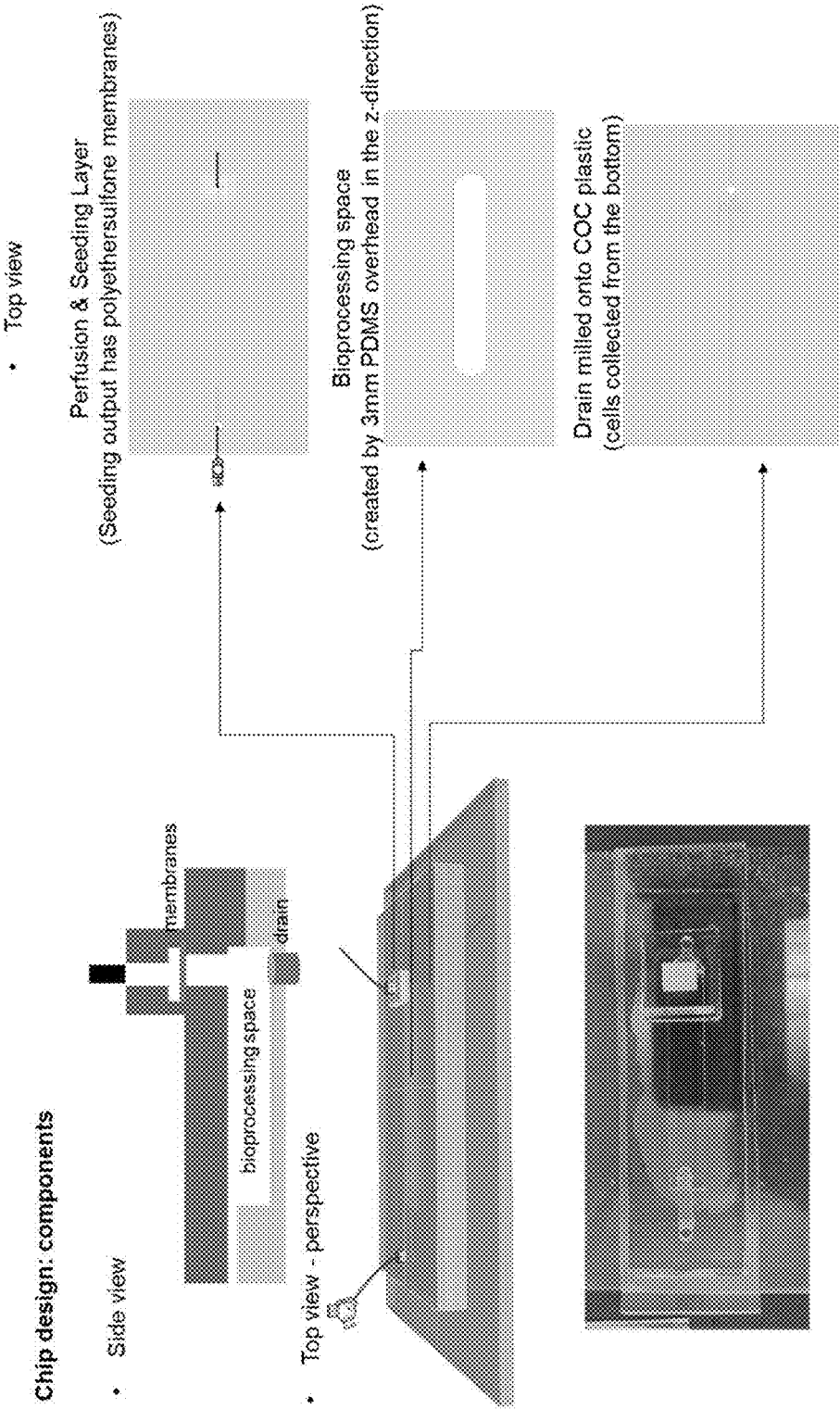
FIG. 4D schematically illustrates a side view and a top view of an exemplary chip, in accordance with some embodiments.

FIG. 4D schematically illustrates a side view and a top view of an exemplary chip. In some embodiments, the chip is formed from a solid support as described elsewhere herein. In some embodiments, the chip may comprise a perfusion and seeding layer comprising a seeding output (also referred to herein as a feeding output). In some cases, the seeding output/feeding output may comprise one or more membranes, which may include, for example, a polyethersulfone membrane. In some embodiments, the chip may comprise another layer comprising a bioprocessing space. In some cases, the bioprocessing space is formed using a PDMS lid. In other cases, the bioprocessing space is formed using a COC lid. In some embodiments, the chip may comprise another layer comprising a collection output (e.g., a collection drain). In some cases, the collection/harvesting output (e.g., a collection drain) may be milled onto or into a COC material or substrate or any other thermoplastic material. The collection output may be a collection drain and may permit collection of one or more cells from or through the bottom surface of the bioprocessing space.

In some embodiments, the chip may comprise one or more feeding outputs located on a top portion or surface of the chip. This may help to mitigate the impact of shear stress on cell growth in the bioprocessing chamber of the chip during perfusion. Shear stress may include any mechanical forces that are imparted on the cells due to a flow of a material through the chip. The shear stress may be directly proportional to the velocity of the flow of the material through the chip. The impact of shear stress may include, for example, changes to cell morphology, cell physiology, or cell behavior. Although some cells may grow well under shear stress, other cells may not respond as well and can even be damaged by shear stress.

Figure 15:
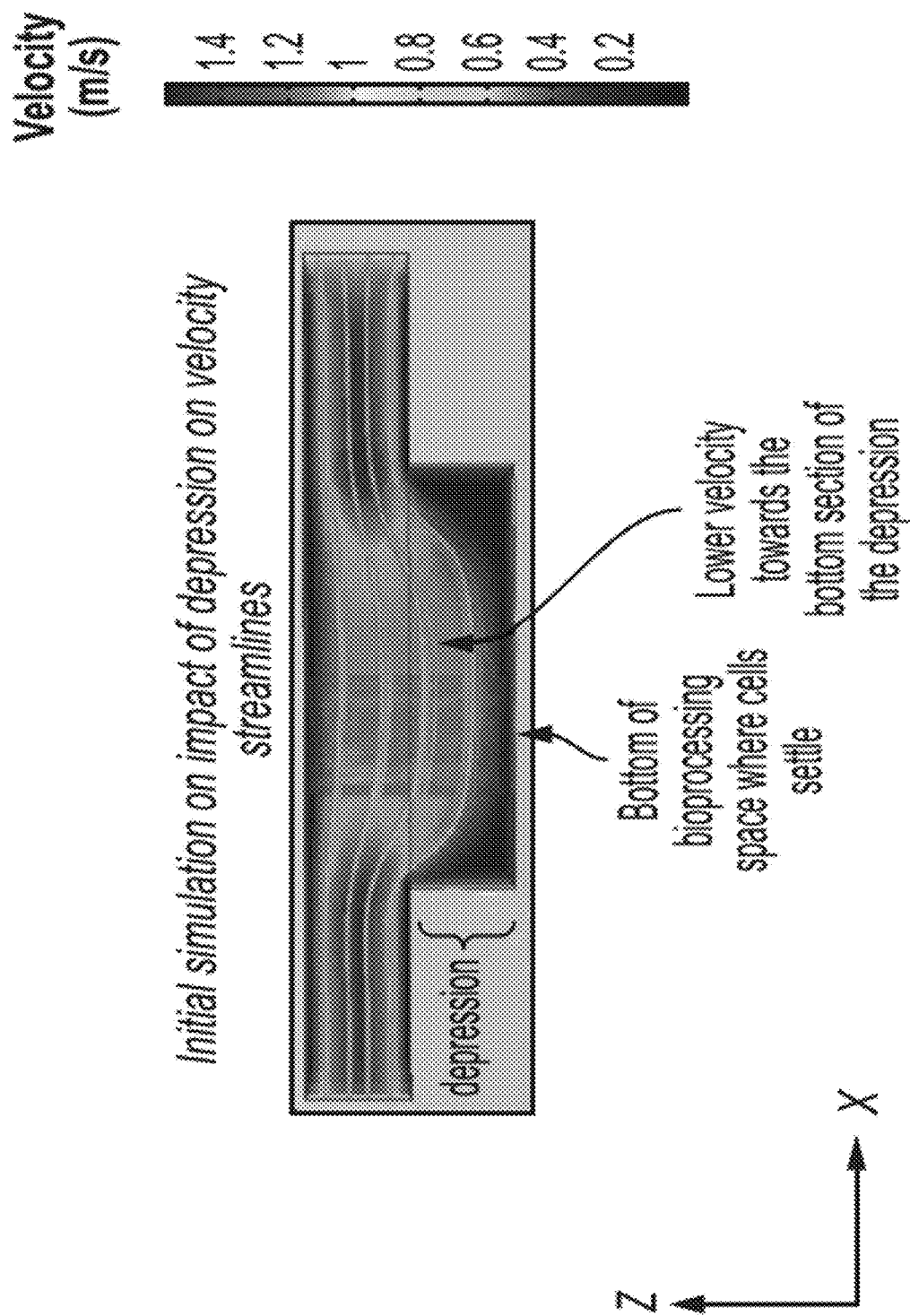
FIG. 15 schematically illustrates a simulation on the impact of a depression on velocity streamlines for a material flowing through the chip during perfusion.

In some cases, shear stress can be reduced by introducing a depression in a portion, a layer, a section, or a volume of the chip. In some cases, the depression may form the bioprocessing chamber of the chip. In some cases, shear can be reduced by introducing a depression. FIG. 15 illustrates a simulation of the impact of the size and shape of the depression on velocity streamlines for a material flowing through the chip during perfusion. The size, shape, position, and orientation of the depression may result in a lower velocity towards a bottom section or portion of the depression. The cells may settle at the bottom section or portion of the depression, where shear stress is relatively minimal compared to other sections or portions of the chip.

Figure 16:
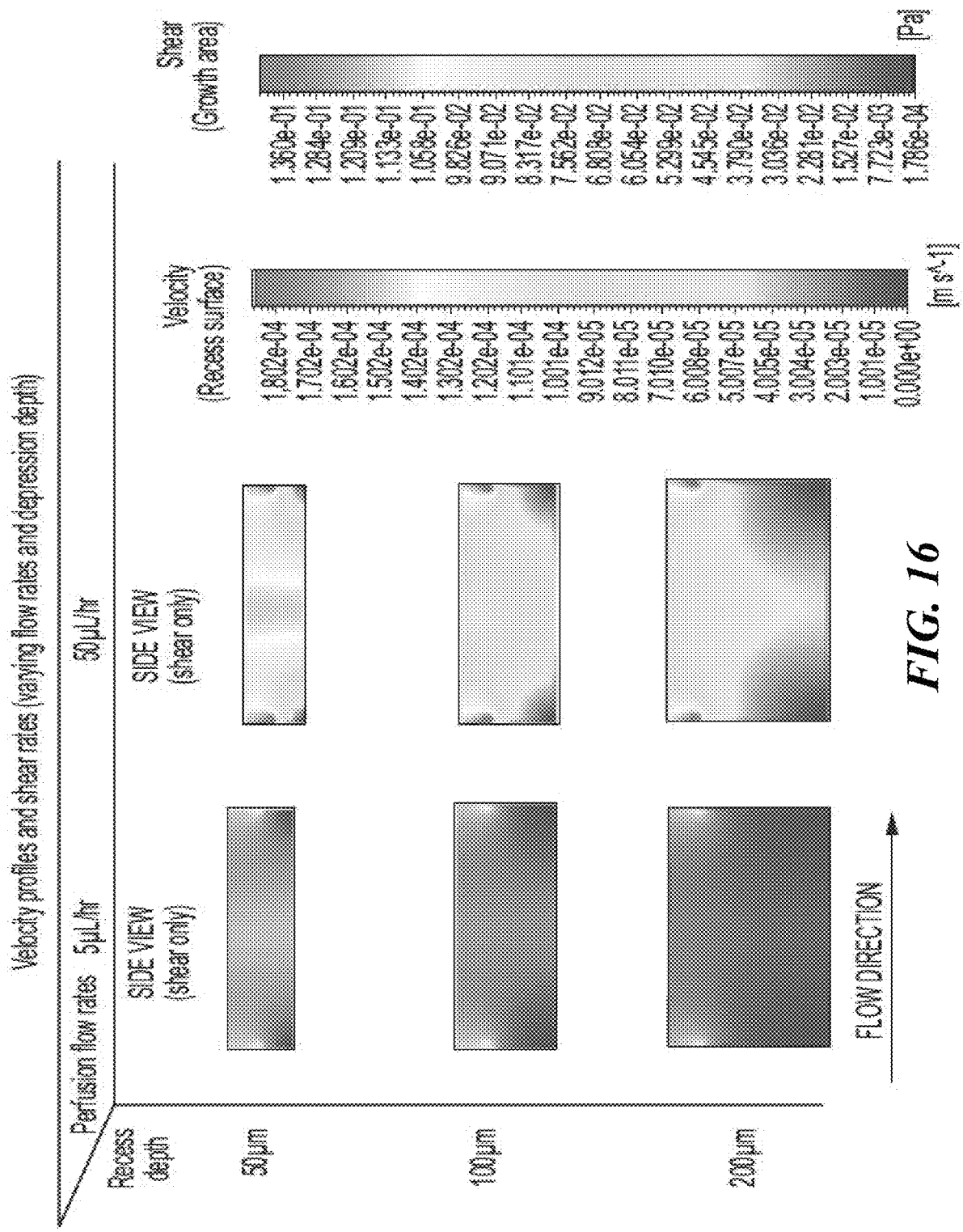
FIG. 16 schematically illustrates velocity profiles and shear rates for various flow rates and depression depths.

FIG. 16 illustrates velocity profiles and shear rates for various flow rates and depression depths. As the depth of the depression increases, the average shear stress exerted on the cells in a cell growth region of the bioprocessing chamber may decrease.

Figure 5A:
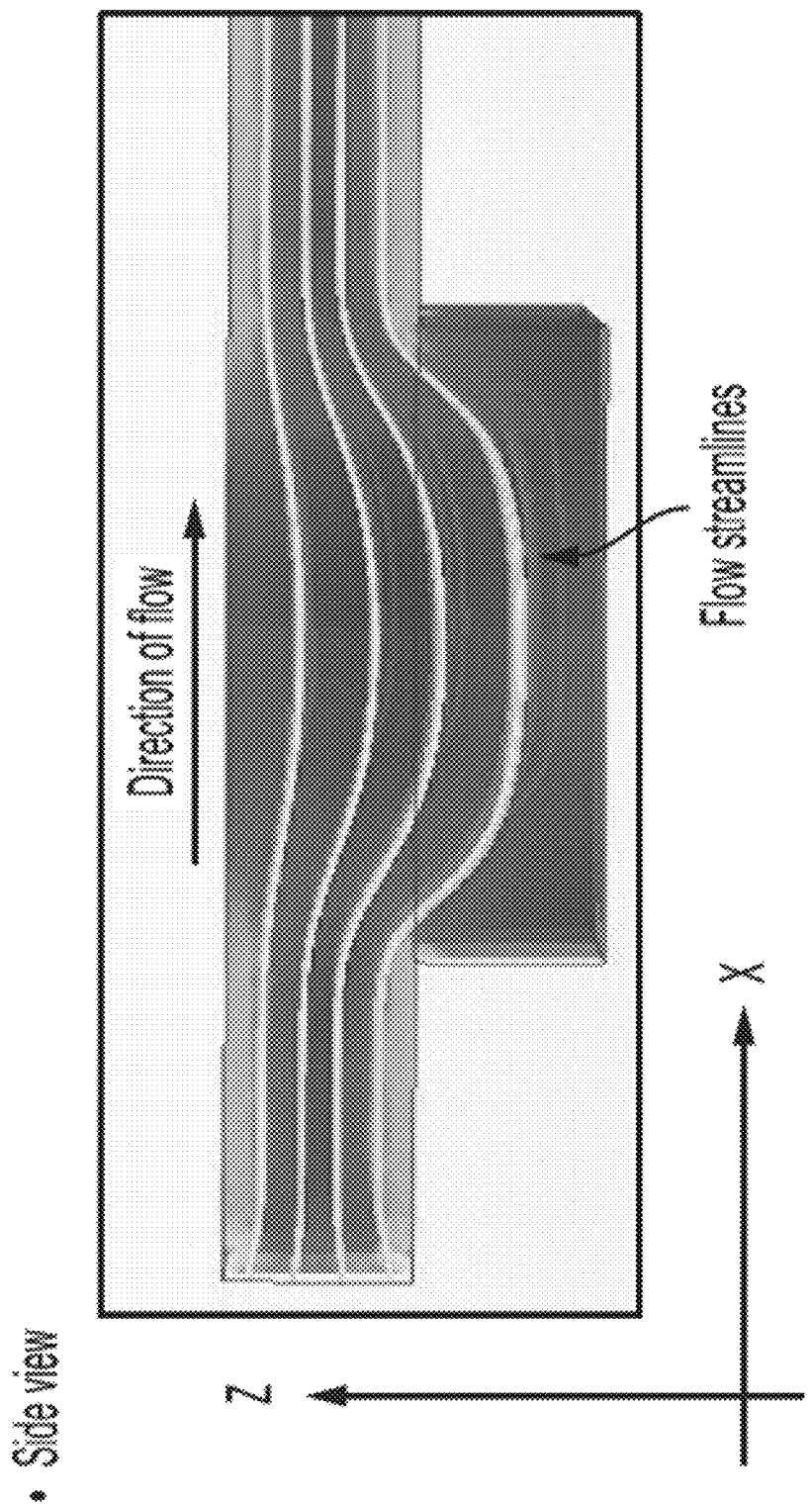
Figure 5B:
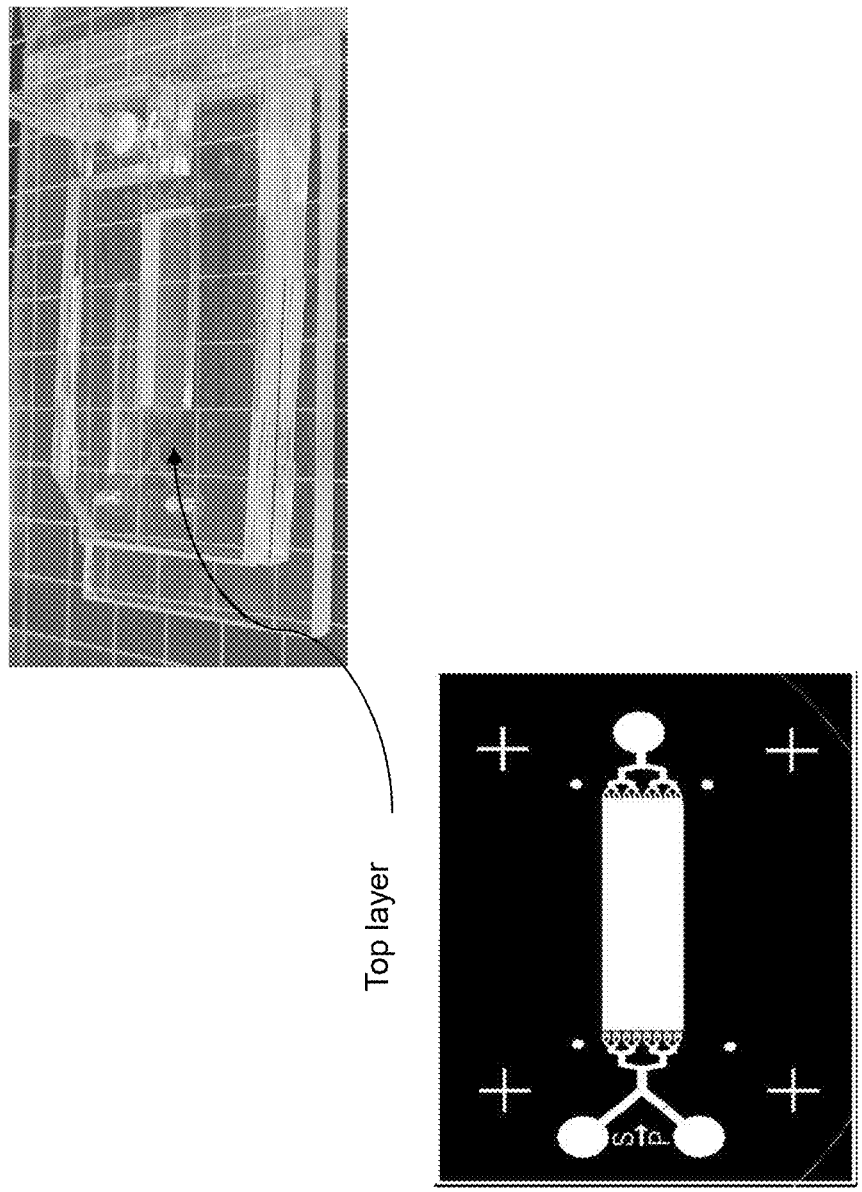

As described above, the chips of the present disclosure can comprise a bioprocessing chamber in fluidic communication with one or more feeding inputs and one or more feeding outputs. In some non-limiting embodiments, the bioprocessing chamber can have a length of about 60 cm, 30 cm, 20 cm, 10 cm, 6 cm, 3 cm, or 2 cm and a width of about 0.1 cm, 0.5 cm, 1 cm, 5 cm, or 10 cm. FIG. 5A shows a cross-sectional side view of the bioprocessing chamber in fluidic communication with the one or more feeding inputs and the one or more feeding outputs. An example of a top layer of a chip comprising one or more feeding inputs and feeding outputs is shown in FIG. 5B. In some cases, the bioprocessing chamber can be in fluidic communication with one or more harvest channels via one or more collection/harvest outputs. FIG. 5C shows exemplary configurations for input channels from the perfusion and seeding side of the chip.

Figure 17:
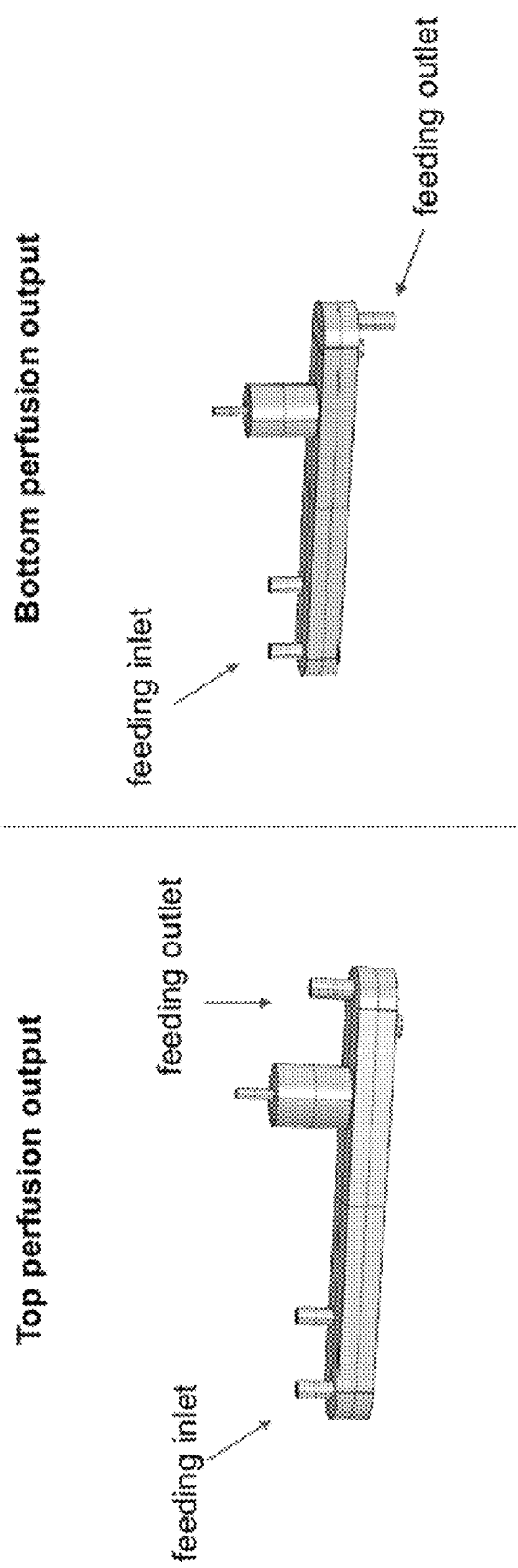
FIG. 17 and FIG. 18 schematically illustrate a comparison of perfusion flow characteristics for various chip designs having one or more feeding outputs located on different portions of an exemplary chip.
Figure 18:
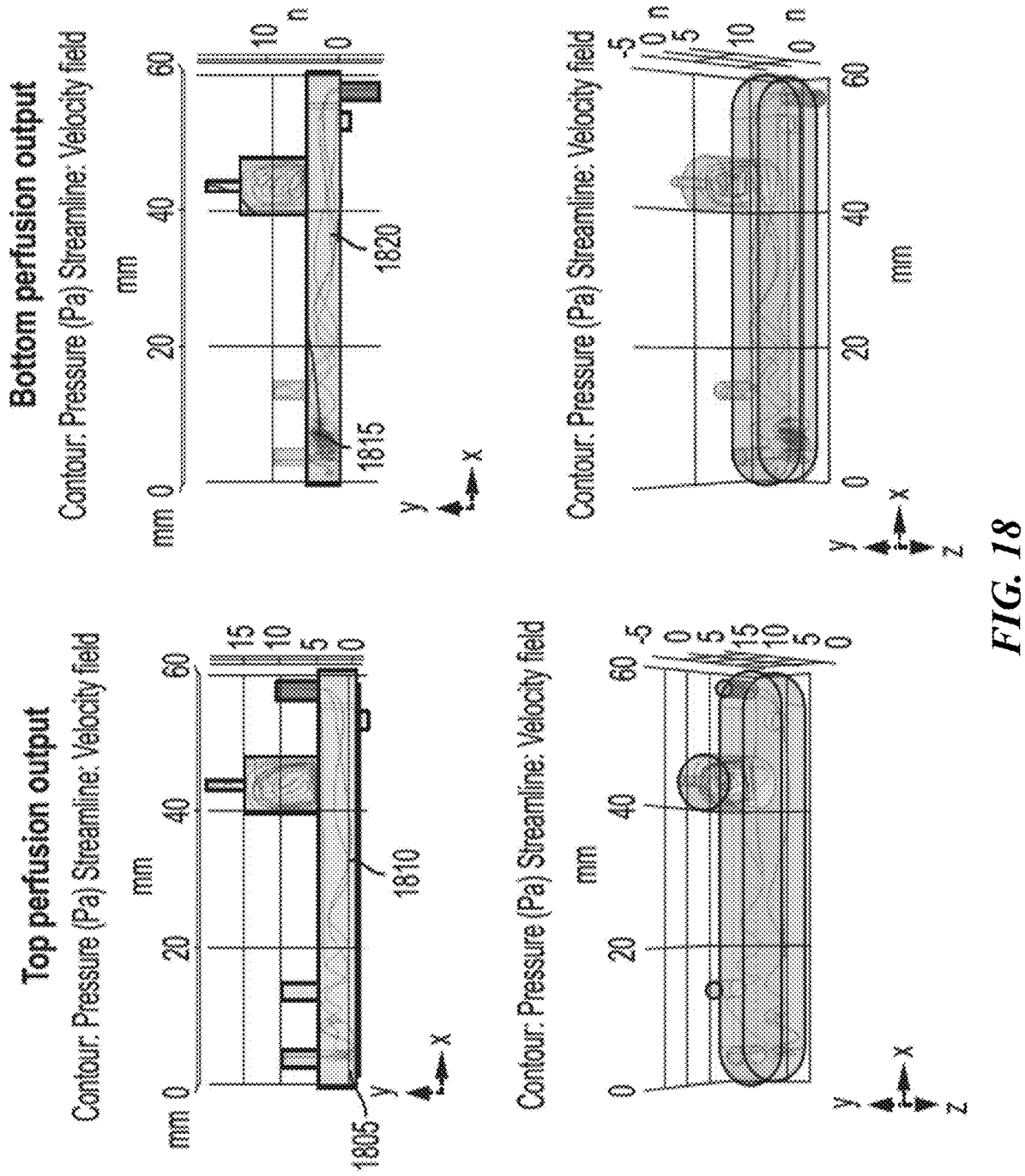

In any of the embodiments described herein, the one or more feeding outputs of the presently disclosed chips may be located on a top portion of the chip. FIG. 17 and FIG. 18 illustrate a comparison of various chip designs with the one or more feeding outputs located on different portions of an exemplary chip. FIG. 18 was generated using laminar flow stationary simulations that were conducted where a first inlet was used as an inlet with 2 m/s (20 mbar), and an outlet was chosen according to the design to be tested. As shown at 1805, entry streamlines may be slightly different because the initial streamline is now directly perpendicular to the chamber and creates some eddies ("turbulent sections"). As shown at 1810, perfusion streamlines may be less dense when the perfusion output is the top, and may allow for less impact on the cells settling near the bottom. As shown at 1815, at the same velocity magnitude, entry streamlines may be more chaotic when the perfusion output is at the bottom. As shown at 1820, perfusion streamlines may be more dense and concentrated at the bottom, and may be detrimental to cell growth and retention during perfusion. In embodiments where the one or more feeding outputs are located on a top portion of the chip, the entry streamlines for a flow of material during perfusion may vary slightly because the initial streamline or flow path through the one or more feeding inputs is perpendicular to a length of the chip along which the material is intended to flow during perfusion. This configuration may create one or more eddies or turbulent sections. In contrast, for embodiments where the one or more feeding outputs are located on a bottom portion of the chip, the entry streamlines and associated flow paths may be more chaotic and turbulent. For embodiments where the one or more feeding outputs are located on a top portion of the chip, the perfusion streamlines may be less dense, which can minimize the impact of shear stress on the cells settling near the bottom of the bioprocessing chamber. For embodiments where the one or more feeding outputs are located on a bottom portion of the chip, the more chaotic entry streamlines may result in flow streamlines through the chip that are more dense and more concentrated at the bottom portion of the chip, which can be detrimental to cell growth and cell retention during perfusion. The differences in flow characteristics for chips having feeding outputs on the top of the chip versus the bottom of the chip can be observed when the velocity of the material through the one or more feeding inputs is kept constant.

Figure 6:
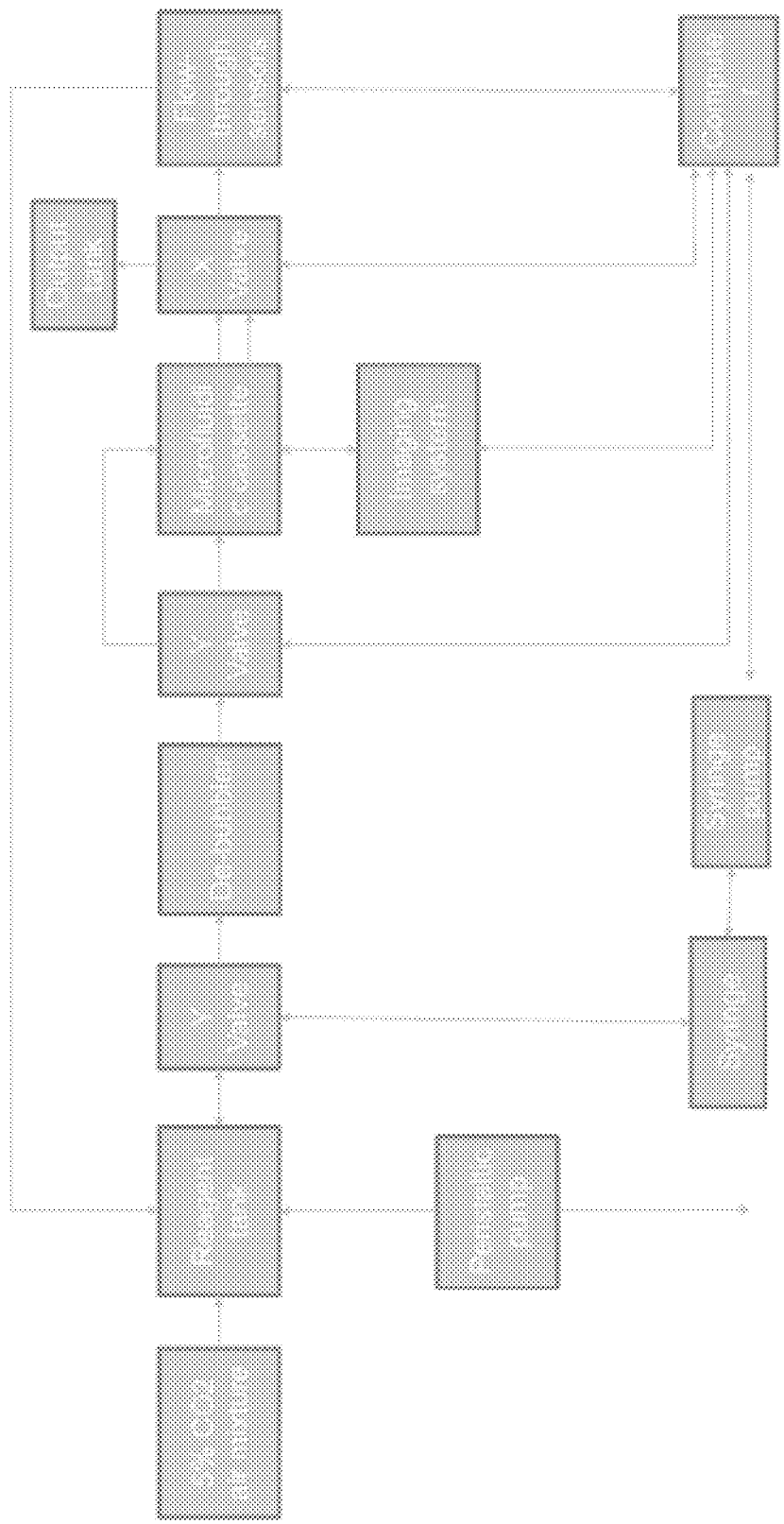
FIG. 6 illustrates an example of a system for bioprocessing, in accordance with some embodiments.

FIG. 6 illustrates an example of a system for bioprocessing. The system can comprise a reagent tank, a pump, one or more valves, a syringe and a syringe pump, a de-bubbler, a microfluidic chip, an imaging system, an output tank, one or more flow-through sensors, and a computer.

The systems and methods disclosed herein can be used for seeding and perfusion of cells, respectively, within a bioprocessing chamber. The seeding can comprise using a mechanism to agitate (e.g., manually or mechanically) the bioprocessing chamber during seeding and/or perfusion to homogenously distribute the cells in the bioprocessing chamber. This can promote homogeneous seeding and homogenous growth. In some non-limiting embodiments, once the cells are ready for harvesting, the bioprocessing chamber can be agitated (e.g., manually or mechanically) to facilitate the release of the cells from the bottom surface and to help move the flow of the released cells towards the harvest channels.

The chips of the present disclosure demonstrate the benefits of a microfluidic approach for cell processing and harvesting. The chips of the present disclosure permit homogeneous seeding, efficient transduction, superior cell expansion, and improved cell recovery. In some cases, the transduction performed in the presently disclosed chips can result in at least a 30% higher efficiency than a well plate. In some cases, the expansion performed in the presently disclosed chips can result in a cell density of at least about 0.35 million cells per mL, 1.5 million cells per mL, 3.5 million cells per mL, 15 million cells per mL, or 35 million cells per mL. In some cases, the harvesting of cells from the presently disclosed chips can result in about, or least, 99%, 98%, 97%, 96%, 95%, 94%, 93%, 92%, 91%, or 90% cell recovery with about or at least 95%, 94%, 93%, 92%, 91%, or 90% viability for the recovered cells. In some cases, at least about, or at least, 50 thousand, 100 thousand, 500 thousand, 1 million, 5 million, 10 million, 20 million, 30 million, 40 million, 50 million, 100 million, or 1 billion cells can be harvested from each chip. In some cases, the harvest procedure can comprise (1) connecting a syringe at the collection output and using the syringe to draw out/pull fluid out of the chip (at 1-5 mL/min). Agitation can help facilitate the exit of fluid. In some cases, the harvest procedure can comprise (2) injecting fluid (e.g., 1-5 mL/min) at the input to help facilitate the exit of fluid.

Figure 7:
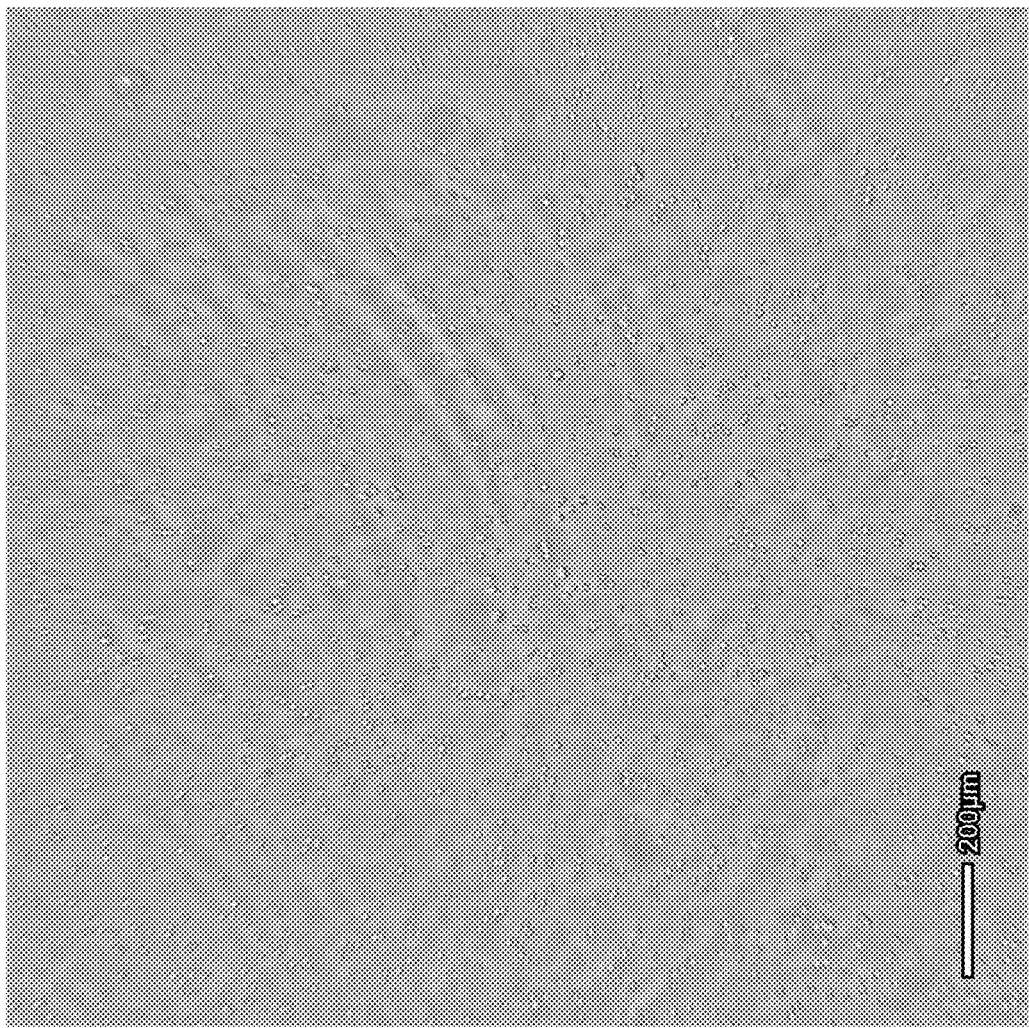
FIG. 7 illustrates experimental results demonstrating homogeneous seeding density throughout the entire surface of the bioprocessing chamber.

FIG. 7 shows experimental results demonstrating homogeneous seeding density throughout the entire surface of the bioprocessing chamber. The T-cells (Jurkats) were seeded in under 5 minutes within a closed system. Cell seeding can be fully automated using the chips of the present disclosure.

Figure 11A:
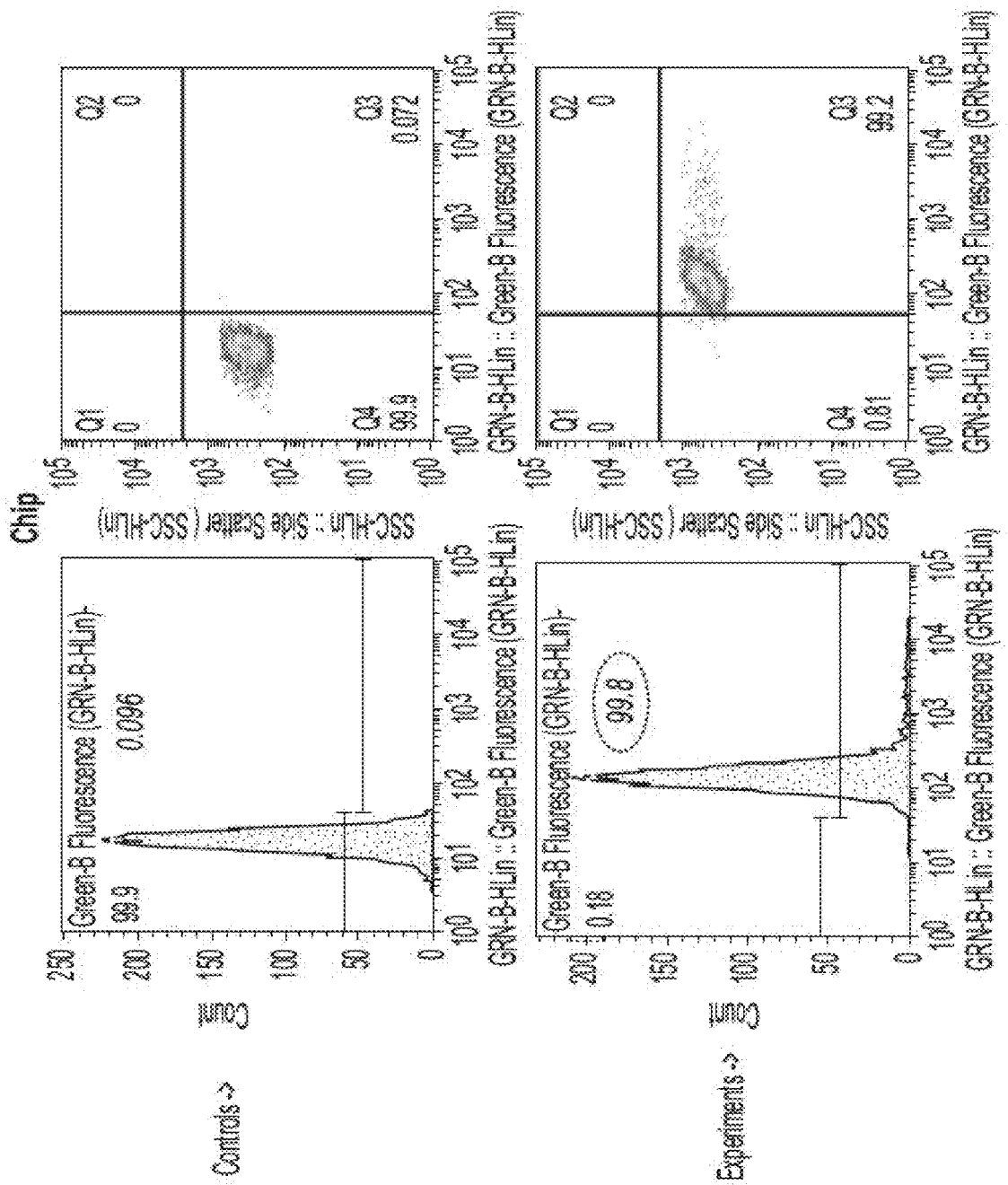
FIG. 11A-11B shows various plots indicating fluorescence peaks detected for experiments conducted in a chip and a well plate.
Figure 11B:
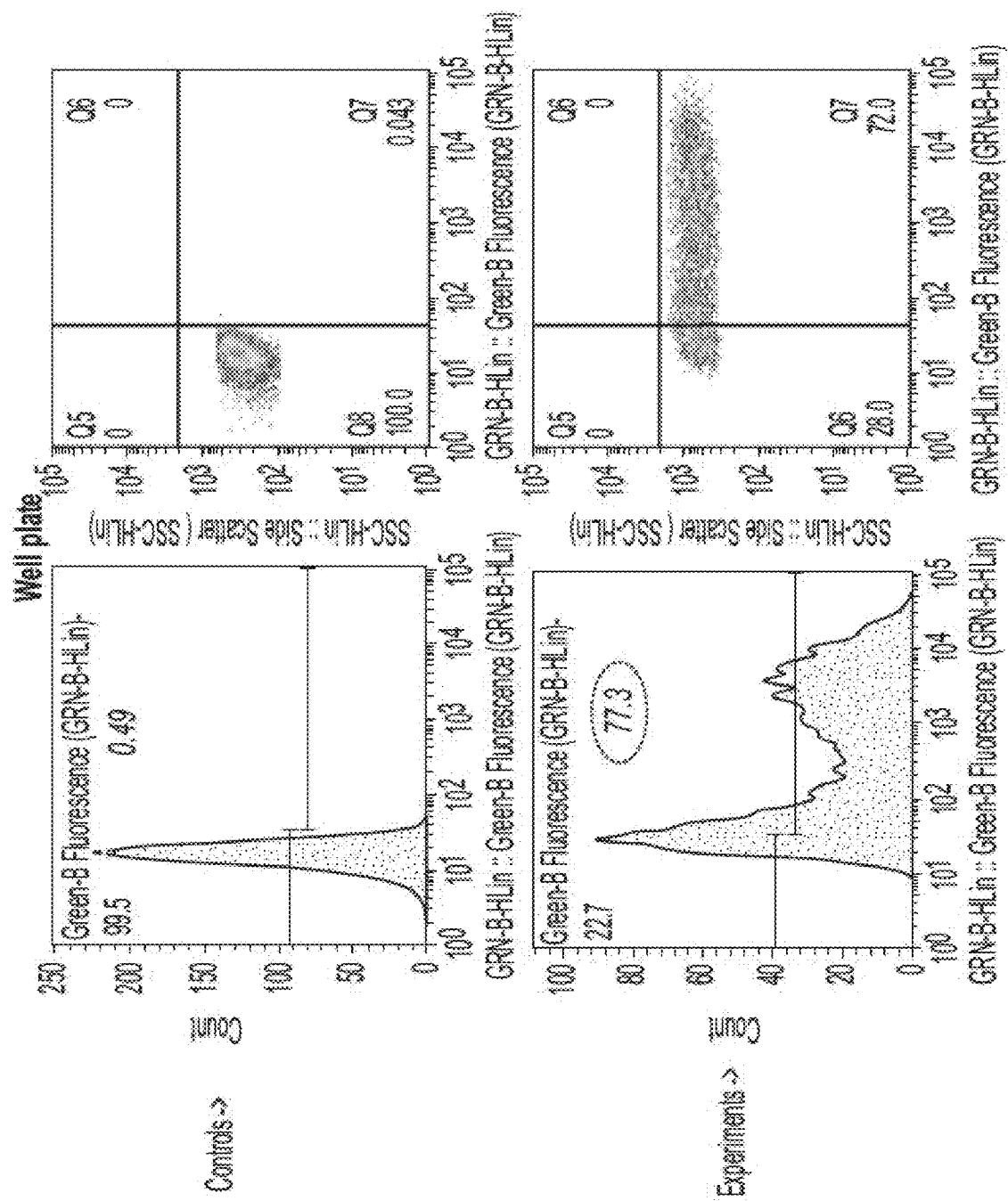

FIGS. 8 and 9 show enhanced T-cell (Jurkat) transduction over time. The fluorescence signals shown in these figures are usable for tracking transduced cells. The cells were seeded at $5 \times 10^5$ cells/ml and perfused after 24 hrs. Cell expansion occurred over a period of several days. FIG. 10 shows a plot of fluorescence (object count) tracking transduced cells over time. An exponential increase in fluorescence signal was observed, indicating the presence of transduced cells. FIG. 11A-11B shows various plots indicating fluorescence peaks detected for experiments conducted in a chip (FIG. 11A) and a well plate (FIG. 11B) using T-cells (Jurkat). The fluorescence peaks detected for the chip experiment have a lower variance than those detected for the well plate experiment.

Figure 12:
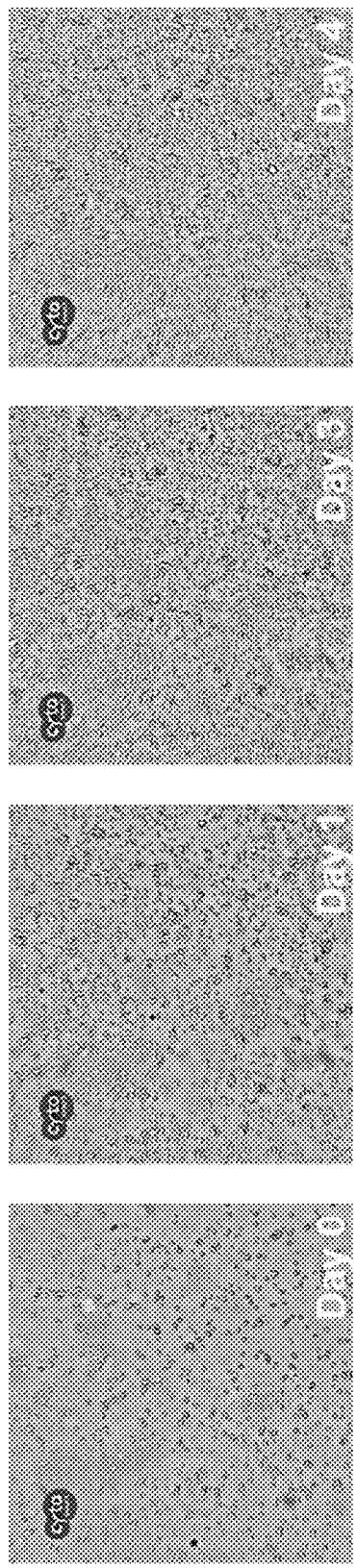
FIG. 12 shows an experiment in which a 30-fold expansion of cells was observed.

FIG. 12 shows an experiment in which a 30-fold expansion of T-cells was observed over a thirteen-day period. Cells were seeded at $2 \times 10^5$ cells/ml and harvested at $6 \times 10^6$ cells/ml.

Figure 13A:
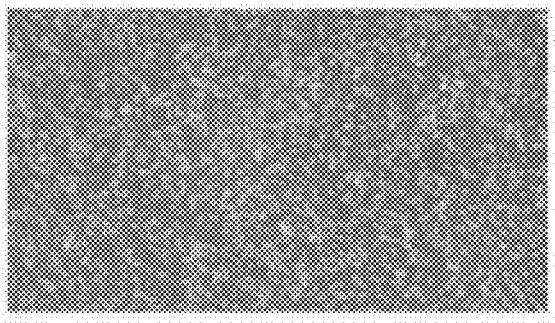
FIGS. 13A and 13B respectively illustrate images taken before cell harvesting and after cell harvesting.
Figure 13B:
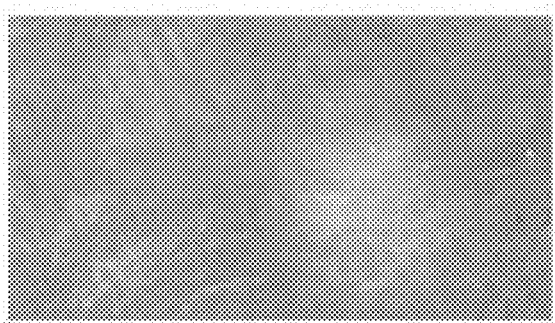

FIG. 13A and FIG. 13B respectively illustrate images taken before cell harvesting and after cell harvesting. Cell harvesting can be performed in less than about 5 seconds, with over 99% cell recovery with high cell viability (at least about 94%). In some cases, high efficiency harvesting can be performed using robust washing procedures and by introducing dissociation agents in a controlled manner. In some cases, harvesting can be automated for the chips disclosed herein.

Applications

In some embodiments, the harvested cells from the presently disclosed chips can be used for various applications. The applications can include, for example, regenerative medicine, treatment of diabetes, cancer, and/or treatment of cardiac-related diseases or neurogenerative diseases. In some cases, the applications can include autologous cell transplantation, allogenic cell transplantation, or reinfusion of cells in a patient. In some cases, the applications include drug delivery studies and anti-bacterial trials.

The chips (solid supports) disclosed herein can yield a large number of cells after cell expansion occurs. In some cases, at least about 50 thousand, 100 thousand, 500 thousand, 1 million, 5 million, 10 million, 20 million, 30 million, 40 million, 50 million, 100 million, 1 billion, or more cells can be harvested from the chips disclosed herein. The cells can comprise, for example, human cells (e.g., stem cells, bone cells, blood cells (e.g., white blood cells (monocytes, lymphocytes, neutrophils, eosinophils, basophils, and macrophages), red blood cells (erythrocytes), or platelets), muscle cells, fat cells, skin cells, nerve cells, immune cells (e.g., T-cells, B-cells or NK cells, lymphocytes, neutrophils, or monocytes/macrophages), cancer cells (e.g., cells associated with carcinoma, sarcoma, melanoma, lymphoma, or leukemia), or non-human cells (including, for instance, animal cells, plant cells, bacterial cells, fungal cells, etc.). Plant cells may include, for example, collenchyma, sclerenchyma, parenchyma, xylem or phloem. Bacterial cells may include, for example, spherical bacterial cells (cocci), rod-shaped bacterial cells (bacilli), spiral bacterial cells (spirilla), comma bacterial cells (vibrios), or corkscrew bacterial cells (spirochaetes). Fungal cells may include, for example, hyphae, yeast cells, spores, Chytridiomycota (chytrids), Zygomycota (bread molds), Ascomycota (yeasts and sac fungi), and the Basidiomycota (club fungi). In some cases, the cells may comprise chimeric antigen receptor T-cells.

Advantages

The systems of the present disclosure can provide a multi-functional design with numerous advantages over other systems. The systems referred to herein can comprise any of the chips and other devices, hardware, or apparatuses described herein.

A device provided herein can be closed at all times, i.e., operations can be carried out in a closed environment (no contact between the fluid and the room environment). The presently disclosed chips can be configured to carry out a plurality of functions in situ (cell seeding, perfusion, sampling, transduction, differentiation, purification, cell harvest) without opening the chip.

Chip Composition

When cells are provided to the chips described herein, the cells can settle on or come in contact with COC, which can possess a glasslike optical clarity that can exceed thermoplastic substitutes such as polycarbonate. COC can be sterilized using standard methods (e.g., steam, ethylene oxide, gamma irradiation, and hydrogen peroxide) without altering its properties. It can also permit UV transmission, which can be best suited for diagnostic analysis. COC can also have low leachables and extractables, making it best suited for direct drug contact. COC is classified as a USP Class VI material and is ISO 10993 compliant including biocompatibility, USP 661.1 and FDA drug and device master files.

In some cases, the chip (solid support) can comprise, for example, a polydimethylsiloxane (PDMS) component, which can form the wall of the bioprocessing chambers, as well as the top layer, which can form part of its ceiling. PDMS can have gas permeability, which can be advantageous for cell growth. PDMS can permit gas equilibration between the bioprocessing chamber and that of the surrounding controlled environment (e.g. incubator), and can withstand autoclave conditions. In some cases, the PDMS component can be replaced with another gas permeable polymer such as, for example, a COC membrane.

In some cases, the chip (solid support) can comprise a plurality of components or layer comprising a plurality of materials. In some cases, the plurality of materials can comprise a cyclic olefin polymer (COP), a cyclic olefin copolymer (COC), or a polydimethylsiloxane (PDMS) material. In some cases, the plurality of materials can comprise one or more USP Class VI materials. In some cases, the plurality of materials can comprise any type of material that is biocompatible and/or biostable. In some cases, the materials for the various components or layers of the chip can have a high permeability (e.g., liquid or gas permeability) to permit a flow of fluid and/or cells into, out of, or through the chip (and any components or layers thereof).

The presently disclosed chips can also contain a filter, e.g., filter membrane made of polyethersulfone (PES). Contrary to other types of membranes (e.g. PTFE), PES can retain its rigid structure over longer periods of time. The filter can have one or more pores. The pore size can be about 5 µm or less, which can be used to retain cells having a diameter ranging from about 8 µm to about 50 µm in the bioprocessing chamber.

Bubbles and Fluid Priming

In some cases, systems provided herein can be primed with fluid, e.g., in order to facilitate injection of the growth media. This priming can reduce the interfacial tension effects that can be associated with flowing liquid in an initially gas-filled chamber. Interfacial tension between gas-liquid can contribute to hydrodynamic resistance. This can be true of microfluidic devices with relatively small dimensions, whose inherent resistance can be high.

In some cases, the chips disclosed herein can have a height of the bioprocessing chamber of around 3-5 mm, such that priming is no longer needed, as the fluid does not experience significant resistance when injected into the bioprocessing chamber.

Evaporation

Due to the fact that PDMS is gas permeable, evaporation can happen, resulting in bubbles in the bioprocessing chamber. In a bioprocessing chamber of small heights, the bubbles can be detrimental to cell growth.

In the presently disclosed chips, the height of the bioprocessing chamber can be, e.g., around 3-5 mm, which can permit a natural separation of the cells and occurring bubbles. While the cells settle at the bottom surface, bubbles are naturally buoyant and thus float towards the top part of the bioprocessing chamber, away from the cells. The environment can be controlled to minimize evaporation and mitigate impacts on the cell growth.

Seeding

The chips (solid supports) provided herein can permit high-efficiency cell seeding, while minimizing loss of injected cells. Such cell seeding may be determined by monitoring the number of cells that are provided to a bioprocessing chamber and the number of cells that adhere to or are retained in a portion or a surface of the bioprocessing chamber. The cells can be spread homogeneously throughout the bioprocessing chamber to enable optimal growth.

The presence of the filter (e.g., filter membrane) can help in blocking cells from prematurely exiting the bioprocessing chamber, ensuring that they stay detained inside the bioprocessing chamber. Mass transport or advection can be a phenomenon due in large part to the fact that cells can be relatively large (>10 µm). Their large size can help them sediment into a recess. To help in homogenous distribution, the chip can be attached to a mechanical agitation device, which can facilitate re-distribution of the seeded cells throughout the bioprocessing chambers.

In some cases, the cells can comprise at least 20,000, 200,000, 350,000, 500,000, 1,000,000, 3,500,000, 10,000,00, 25,000,000, or 50,000,000 cells/mL. In any of the embodiments described herein, the cells can comprise microorganisms, mammalian cells, HEK293 cells, T-cells, Jurkat cells, CHO cells, mesenchymal stem cells, embryonic stem cells, induced pluripotent stem cells, or hematopoietic stem cells. The bioprocessing chambers can comprise at least about 0.35, 0.5, 1, 3.5, 5, 10, 15, or 20 million cells/mL.

Perfusion

Cells deplete surrounding media from nutrients in static conditions. The rate of media flow in the microfluidic chip can be carefully regulated. The chip designs disclosed herein can balance perfusion flow rate with shear stress so that cells get access to enough nutrients while at the same time, the flow is low enough so as not to remove the cells from their substrate.

In the microscale, numerous parameters can be involved in ensuring cell growth, including temperature gradients, oxygen levels, chemical gradients, cell-to-cell interactions, cell-to-molecule interactions, CO2 level, shear stress, and cell-substrate interactions.

The fact that the perfusion input channels can be on a different, e.g. higher, plane than the cells (settling at the bottom of the bioprocessing chamber), means that they can be protected from damaging shear stress induced by the fluid streamlines during perfusion. Shear stress can decrease with depth. Thus, the cells can avoid significant shear stress in the chip described herein.

In some cases, the perfusion can come from the widthwise side because one or more fluid inlets are positioned at a higher plane than the bottom of the bioprocessing chamber, which can cause the reduction in shear stress. When injected from the lengthwise side, the input channels can be positioned at a higher plane than the bottom surface of the bioprocessing chamber.

Nutrient and gas diffusion as well as cell consumption can also be optimized. When cells are not homogeneously distributed during seeding, a consumption rate that follows a Poisson distribution can be expected where there is a higher consumption rate near the position of the feeding input channels (since it can be in first contact with the nutrients). Mechanical or manual agitation employed during seeding can be beneficial for perfusion to ensure that nutrients are distributed throughout the bioprocessing chamber.

In some embodiments, the method can further comprise expanding the distributed cells to generate expanded cells. In some cases, the expanding comprises expanding the distributed cells about, or at least 2-fold, 3-fold, 4-fold, 5-fold, 6-fold, 6.5-fold, 7-fold, 8-fold, 9-fold, 10-fold, 11-fold, 12-fold, 25-fold, 50-fold, 100-fold, 150-fold, or 200-fold. In some cases, the expanding occurs over about, or at least 24 h, 48 h, 72 h, 96 h, 120 h, 144 h, 168 h, 192 h, 216 h, 240 h, 264 h, 288 h, 312 h, 336 h, 360 h, 720 h, 1080 h, or 1200 h.

Coating

Appropriate surface treatment can also be performed inside the bioprocessing chamber of the chip depending on the experimental conditions. Such surface treatments can allow adherent particles or cells to stick to the surface such that particle-wall adhesion takes place. Additional coating methods can be used to facilitate cell attachment or detachment on the COC substrate. In some cases, the coating can comprise one or more polymeric surfactants.

In some cases, the coating can comprise any type of biocompatible or biostable material that facilitates cell adhesion or growth. In some cases, the coating may comprise, for example, biological materials such as extracellular matrix, attachment and adhesion proteins, collagen, laminin, fibronectin, mucopolysaccharides, heparin sulfate, hyaluronidase, or chondroitin sulfate. In some cases, the coating may comprise a non-biological material.

Harvest

In various aspects, cells may be harvested from the bioprocessing chamber. Positioning the harvest/collection channels on a different plane can optimize space and remove the need for lateral channels on either side of the chip in the lengthwise direction, which can make the chip design cumbersome and at the same time, generally adds chip footprint.

In some cases, harvesting can comprise harvesting at least 75%, 80%, 85%, 90%, 95%, 96%, 97%, 98%, or 99% of the cells to provide harvested cells. Harvesting can comprise removing cells from a bioprocessing chamber. Harvesting may begin when a portion of the seeded or expanded cells are removed from a bioprocessing chamber by any manual or automatic operation or process, and may end when at least a portion of the seeded or expanded cells are obtained by a human or a machine. In some cases, the harvesting occurs in 5 min or less, 1 min or less, 50 seconds or less, 40 seconds or less, 30 seconds or less, 20 seconds or less, 10 seconds or less, or 5 seconds or less. In some cases, at least 75%, 80%, 85%, 90%, 91%, 92%, 93%, or 94% of the harvested cells can be viable. In some cases, the harvesting of cells from the presently disclosed chips can result in about, or least, 99%, 98%, 97%, 96%, 95%, 94%, 93%, 92%, 91%, or 90% cell recovery with about or at least 95%, 94%, 93%, 92%, 91%, or 90% viability of the recovered cells.

Cells may be harvested through a collection output. In some cases, harvesting cells may be performed through the bottom surface of the bioprocessing chamber by taking advantage of gravity facilitates the exit of the fluid and cells and may be harvested using a collection drain. Drawing the fluid out (via a syringe pump or negative pressure) while pushing fluid from the perfusion side (via a second syringe pump or positive pressure) can also help complete removal of the fluid and cells to increase harvest efficiency. In some embodiments, gravity is not needed to harvest the cells through the top surface of the bioprocessing chamber.

Sampling

Sampling can involve taking representative samples of cells from inside the bioprocessing chamber without interfering with cell growth and without opening the chip. Varying the drawing flow rate at the harvest or collection output can control the amount of fluid (and cells) collected.

Chip

In one aspect, the present disclosure provides a support (e.g., a solid support) comprising a microfluidic feeding input channel (101), a bioprocessing chamber (105), and a collection output. The bioprocessing chamber can be in fluidic communication with the microfluidic feeding input channel (101). The bioprocessing chamber can comprise a bottom surface. The collection output (108) can be fluidically connected to the bioprocessing chamber (105) via the bottom surface.

In some embodiments, the collection output may not or need not be orthogonal to the bottom surface. In other embodiments, the collection output (108) can be orthogonal to the bottom surface.

In some cases, a flow path comprising the microfluidic feeding input channel (101), the bioprocessing chamber (105) and the collection output (108) can be closed or blocked to prevent fluid flow along the flow path.

In some cases, the bioprocessing chamber (105) can be elongated and can comprise a first end wall and a second end wall opposite the first end wall. The bottom surface can be substantially orthogonal to the first end wall and the second end wall.

In some embodiments, the bioprocessing chamber comprises a fillet along an upper perimeter of the bioprocessing chamber. In some cases, the fillet is configured to evenly distribute pressure across the entire length of the chamber and reduce the likelihood of fracture.

In some embodiments, the microfluidic feeding input channel (101) can be fluidically connected to the first end wall of the bioprocessing chamber (105) and the collection output (108) can be fluidically connected to the bottom surface nearer the second wall end of the bioprocessing chamber (105) than the first end wall.

In some cases, the solid support can comprise one or more valves that regulate fluid flow from the bioprocessing chamber (105) into the collection output (108). In other cases, the solid support may not or need not comprise one or more valves that regulate fluid flow from the bioprocessing chamber (105) into the collection output (108).

In another aspect, the present disclosure provides a solid support comprising a bioprocessing chamber (105) comprising a bottom surface and a collection output (108) fluidically connected to the bioprocessing chamber (105) via the bottom surface. The solid support may or may not comprise a valve that regulates fluid flow from the bioprocessing chamber (105) into the collection output (108).

In some embodiments, the collection output may not or need not be orthogonal to the bottom surface. In other embodiments, the collection output (108) can be orthogonal to the bottom surface. In some embodiments, the collection output (108) can be parallel to the bottom surface. In some embodiments, the collection output (108) may not or need not be orthogonal to the top surface. In other embodiments, the collection output (108) can be orthogonal to the top surface. In some embodiments, the collection output (108) can be parallel to top surface. In some embodiments, the collection output (108) can be parallel to the bottom surface.

In another aspect, the present disclosure provides a solid support comprising a bioprocessing chamber (105) comprising a ceiling, a feeding output channel (103) fluidically connected to the bioprocessing chamber (105) via the ceiling, and a filter (e.g., a filter membrane) that selectively prevents solid particles from passing from the bioprocessing chamber (105) to the feeding output channel (103).

In some embodiments, the filter (104) comprises a hydrophilic material, e.g. polyethersulfone (PES), polycarbonate, or polyester. In some cases, the filter (104) comprises a pore size of less than 10 µm, less than 7.5 µm, less than 5 µm, or less than 2.5 µm. In some cases, the filter (104) can be rectangular or circular.

In some embodiments, the solid support can further comprise a microfluidic feeding input channel (101). The bioprocessing chamber (105) can be fluidically coupled to the microfluidic feeding input channel (101).

In some embodiments, the solid support can comprise a flow path comprising the microfluidic feeding input channel (101), the bioprocessing chamber (105), and the feeding output channel (103). In some cases, the flow path can be closed or at least partially restricted.

In some embodiments, the bioprocessing chamber (105) can be elongated and can comprise a first end wall and a second end wall opposite the first end wall. In some cases, the ceiling of the bioprocessing chamber can be substantially orthogonal to the first end wall and the second end wall. In some embodiments, the ceiling of the bioprocessing chamber comprises a fillet.

In some embodiments, the microfluidic feeding input channel (101) can be fluidically connected to the first end wall of the bioprocessing chamber (105) and the feeding output channel (103) can be fluidically connected to the ceiling nearer the second wall end of the bioprocessing chamber (105) than the first end wall. In some embodiments, the feeding output channel may be fluidically connected to the bioprocessing chamber via the ceiling of the bioprocessing chamber. In some cases, the feeding output channel is fluidically connected to the bioprocessing chamber via one or more holes, apertures, channels, or passageways in or through at least a portion of the ceiling of the bioprocessing chamber. In some cases, a plurality of feeding output channels are connected to the bioprocessing chamber via the ceiling of the bioprocessing chamber.

In another aspect, the present disclosure provides a solid support comprising a bioprocessing chamber (105) comprising a bottom surface and a ceiling, a collection output (108) fluidically connected to the bioprocessing chamber (105) via the bottom surface, and a feeding output channel (103) fluidically connected to the bioprocessing chamber (105) via the ceiling.

In some embodiments, the collection output (108) can be positioned directly below the feed output channel (103). In other embodiments, the collection output (108) may not or need not be positioned directly below the feed output channel (103).

In some cases, the solid support can further comprise a filter 104 (e.g., a filter membrane) that selectively prevents solid particles from passing from the bioprocessing chamber (105) to the feeding output channel (103).

In some embodiments, the solid support can further comprise a feeding input channel (101). In some cases, the bioprocessing chamber (105) can be fluidically connected to the feeding input channel (101). In some cases, the feeding input channel (101) can be a single channel. In other cases, the feeding input channel (101) can comprise a plurality of feeding input channels (101). In some cases, the plurality of feeding input channels (101) comprises a binary tree network.

In some embodiments, the solid support can further comprise a feeding input fluidically connected to the feeding input channel (101). The feeding input can comprise one feeding input. Alternatively, the feeding input can comprise a plurality of feeding inputs. In any of the embodiments described herein, the feeding input channel (101) can comprise a length dimension parallel to a length dimension of the bioprocessing chamber (105).

In some cases, the bottom surface of the solid support can be on a first plane, and the feeding input channel (101) of the solid support can be on a second plane. The first plane and the second plane can be different, and the first plane can be below the second plane.

In some cases, a length dimension of the bioprocessing chamber (105) can be at least 2×, 3×, 4×, 5×, 10×, 15×, or 20× a width dimension of the bioprocessing chamber (105). In some cases, the bioprocessing chamber (105) has a height of at least 0.1 mm, 0.2 mm, 0.3 mm, 0.4 mm, or 0.5 mm. In some cases, the height of the bioprocessing chamber is about 1 mm, 2 mm, 3 mm, 4 mm, or 5 mm. In some cases, the height of the bioprocessing chamber is less than about 1 mm. In some cases, the height of the bioprocessing chamber is greater than about 5 mm.

In some cases, the bioprocessing chamber (105) can comprise a curved edge. The curved edge can be at an end of bioprocessing chamber (105).

In any of the embodiments described herein, the bottom surface of the solid support can comprise a material that is classified U.S. Pharmacopeia (USP) Class VI and is ISO 10993 compliant. In some cases, the bottom surface can comprise cyclic olefin copolymer (COC). In some cases, the bioprocessing chamber (105) can comprise one or more walls. The one or more walls can comprise, for example, COC, PDMS, a medical grade thermoplastic, or a medical grade soft elastomer. In some cases, the ceiling of the bioprocessing chamber (105) can comprise PDMS or COC or a gas-permeable material. In some embodiments, the bioprocessing chamber (105) can be coated with a coating. The coating can interact with or adhere to the bottom surface via curing or incubation.

Agitation

In another aspect, the present disclosure provides a system comprising any of the solid supports described herein. The system can further comprise an agitation device that is coupled or attached to the solid support. The agitation device can comprise one or more motors configured to produce an oscillatory or circular motion. The oscillatory or circular motion may or may not be periodic. In some embodiments, a human operator may agitate the solid support manually. The agitation may aid in homogenously distributing cells or other solid particles in the bioprocessing chamber.

Methods

In another aspect, the present disclosure provides a method for bioprocessing. The method can comprise providing any of the solid support described herein. The method can further comprise flowing a fluid through the microfluidic feeding input channel (101) and the bioprocessing chamber (105) of the solid support. In some cases, the fluid comprises solid particles.

In some embodiments, the method can further comprise seeding the solid particles in the bioprocessing chamber (105), thereby providing seeded solid particles. In some embodiments, the method can further comprise agitating the solid support to homogenously distribute the solid particles in the bioprocessing chamber (105). In some cases, the seeded solid particles comprise one or more cells.

In some embodiments, the method can further comprise expanding the cells in the bioprocessing chamber (105). In some embodiments, the method can further comprise harvesting the expanded cells through the collection output (108). In some cases, the harvesting comprises using positive pressure, negative pressure, or both.

In another aspect, the present disclosure provides a method for bioprocessing. The method can comprise providing any one or more of the solid supports disclosed herein, and flowing a fluid through the bioprocessing chamber (105) and a feeding output channel (103) of the solid support. The fluid can comprise solid particles, and the solid particles can comprise one or more cells.

In some cases, a filter (104) can be used to prevent the cells from entering the feeding output channel (103). In some embodiments, the cells can comprise human cells.

In another aspect, the present disclosure provides a method for bioprocessing. The method can comprise providing any one or more of the solid supports described herein, and flowing a fluid through the bioprocessing chamber (105) and the feeding output channel (103). The fluid can comprise one or more solid particles. The one or more solid particles can comprise one or more cells. In some embodiments, the method can further comprise seeding the cells in the bioprocessing chamber (105), thereby providing seeded cells. In some cases, while the fluid is flowing through the bioprocessing chamber (105), the cells may not enter the collection output (108) or the feeding output channel (103). In some embodiments, the method can further comprise contacting the seeded cells with one or more reagents. The reagents can comprise, for example, balanced salt solutions, buffers, detergents, chelators, or any materials or substances that either (i) promote or facilitate cell adhesion or (ii) prevent cell adhesion (e.g., for suspension of cells).

In some cases, prior to seeding, an optional priming step is performed. In some cases, the priming step involves replacing or displacing the air in the bioprocessing chamber with water or aqueous solution to make seeding easier and to allow for the cells to be seeded homogenously. In some cases, the priming step is performed when the chip is oriented horizontally, vertically, or at an angle ranging from 1 degree to 90 degrees or more. In some cases, the angle is about 45 degrees. In some embodiments, the bioprocessing methods disclosed herein comprise a method for priming a chip. In some embodiments, the method comprises orienting the chip vertically such that the inlet channels of the chip are oriented towards the bottom and the outlet channels of the chip are oriented towards the top. In some embodiments, the method further comprises flowing a priming fluid through the inlet channels at a flow rate until the chip is filled with priming fluid and the priming fluid comes out of the outlet channels. In some cases, the flow rate of the priming fluid ranges from about 1 mL/min to about 5 mL/min.

In some cases, the cells can be seeded at a flow rate ranging from 0.1 microliters per second (μL/s) to 10 μL/s or more. In some cases, the cells can be seeded at a flow rate of at least about 0.17 μL/s. In some cases, the cells are seeded at a flow rate ranging from about 1 mL/min to about 100 mL/min or more.

In some cases, the cells can be harvested at a flow rate ranging from about 0.1 microliters per second (μL/s) to about 10 μL/s or more. In some cases, the cells can be harvested at a flow rate ranging from about 0.17 μL/s to about 1.59 μL/s. In some cases, the cells are harvested at a flow rate ranging from about 1 mL/min to about 100 mL/min or more. In some cases, the chip is placed in a vertical orientation for harvesting. In some cases, a pull/push method is used to harvest the cells.

In some embodiments, the chip may comprise one or more trap features. The one or more trap features may comprise, for example, one or more chevrons or pillars. The one or more trap features may be implemented to facilitate the seeding, capture, and/or harvesting of cells. In some cases, the one or more trap features may be located in or near a bioprocessing region of the bioprocessing chamber. In some cases, the one or more trap features may be located on a bottom surface of the bioprocessing chamber or one or more side walls of the bioprocessing chamber. In some cases, the trap features reach the height of the bioprocessing chamber and serve as additional supports for the ceiling of the bioprocessing chamber.

In some embodiments, the chip may comprise a first dimension and a second dimension. The first dimension may correspond to a length of the chip. The second dimension may correspond to a width of the chip. The first dimension may be greater than the second dimension.

In some embodiments, the chip may comprise a fan design or configuration. Such fan design or configuration may help to improve fluid flow through the chip. The fan design or configuration may comprise one or more inputs, outputs, or channels that branch out or converge. The fan configuration may be implemented for a harvest layer of a chip to increase fluidic flow in the bioprocessing area and to help push cells out and into a harvest channel of the chip.

In some cases, the fan configuration may be flatter in one section compared to another section to aid in space/volume management. In some cases, the fan configuration may comprise one or more angled portions to facilitate flow through the chip. In some cases, each branch of the fan configuration may flow directly into a recess or channel of the chip. Each recess or channel may lead directly to an outlet, thereby facilitating collection. In some cases, the fan configuration may be dimensioned or configured to provide a shorter travel distance through a center region of the fan. In some cases, the fan configuration may generate vortices that can lead to a Gaussian distribution of cells as opposed to a Poisson distribution of cells so that the cells in the center region of the fan can be easily and efficiently collected.

In some embodiments, the chip may comprise a COC material. In some cases, the base of the chip may comprise the COC material. In some cases, the fan configuration may be provided on a milled COC platform or substrate of the chip to enhance cell growth and harvesting efficiencies. In some cases, the chip may comprise a CNC-milled layer comprising COC and an additional layer comprising PDMS.

In some cases, a portion of the chip may be modified (e.g., shortened or elongated) to minimize the distance of the harvest fluid path. In some cases, minimizing the distance of the harvest fluid path may enhance harvesting efficiency and reduce a number of cells remaining in the channels of the chip after flowing a harvesting medium through the chip.

In some embodiments, the spatial configuration of the harvesting channels may be adapted to reach various corners or extremities of the bioprocessing chamber to ensure that the cells are harvested with high efficiency. In some cases, harvesting may occur in multiple steps to account for differences in harvesting performance across or within different portions or sections of the harvesting channels.

In some embodiments, one or more side ports of the chip may be used to enhance harvesting. In some cases, the side ports may produce vortices that improve cell harvesting throughout different portions or sections of the chip. In some cases, side tubing and/or one or more outputs may be used to further enhance harvesting. In some cases, the one or more outputs may be located at a bottom region or portion of the chip.

In some embodiments, the chip may comprise or utilize one or more filters. As described elsewhere herein, the one or more filters may be used to improve the efficiency of cell seeding. In some cases, the one or more filters may comprise a 5 micrometer filter that enables high efficiency seeding (>99%).

Figure 19:
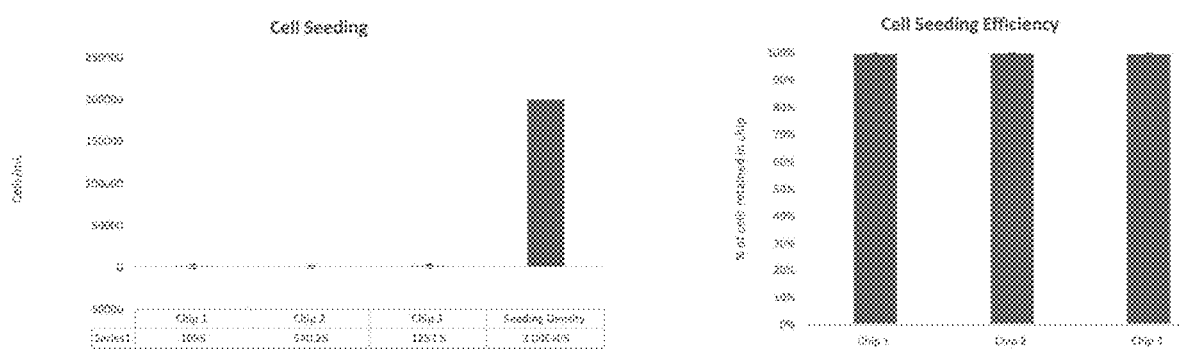
FIG. 19 schematically illustrates cell seeding efficiencies for chips utilizing a filter, in accordance with some embodiments.

FIG. 19 illustrates cell seeding efficiencies for chips utilizing a 5 micrometer filter located at, near, or in a feeding output channel. The cells were seeded at $2\times10^5$ cells per mL and 100 mbar initially, and thereafter flowed through the chips at a flow pressure of 30 mbar. The chips exhibited a high seeding efficiency of over 99%.

In some embodiments, the chip may comprise one or more treated surfaces. In some cases, the treated surfaces may include a bottom surface or one or more side walls of a bioprocessing chamber, or one or more inner portions or surfaces of the feeding channels or harvest channels. The one or more treated surfaces may comprise a surface treatment (e.g., an anti-adherence material to reduce cell adhesion to a portion or a surface of the chip, or a non-ionic surfactant such as Pluronic® F-68 that can be used to control shear forces in suspension culture and reduce the ability of suspension cells to stick to a surface or other portion of the chip, without causing issues with cell viability or cell proliferation). Table 1 below illustrates the harvesting efficiency for various chips (p2-p4) treated with a non-ionic surfactant compared to other chips (p1, p5, and p6) that have not been treated with a non-ionic surfactant.

TABLE 1

| Chip Type | Volume In $(0.5 \times 10^6$ cells) in/out | Cell Density cells/ml reading | Total number of cells | Cell Viability % | Cell size | Harvested cells % |
| --- | --- | --- | --- | --- | --- | --- |
| chip p1 reading 1 | 1 ml/3 ml | 159000 | 477000 | 94.4 | 10.45 | 95.4 |
| Chip p2 reading 1 | 1 ml/3 ml | 269500 | 808500 | 89.65 | 9.15 | 99 |
| Chip p3 reading 1 | 1 ml/3 ml | 175000 | 525000 | 62.55 | 11.3 | 99 |
| Chip p4 reading 1 | 1 ml/3 ml | 184000 | 552000 | 91.65 | 11 | 99 |
| Chip p5 reading 1 | 1 ml/3 ml | 157000 | 471000 | 94.9 | 10.8 | 94.2 |
| Chip p6 reading 1 | 1 ml/3 ml | 531000 | 311166 | 91.55 | 11 | 62.2 |

In some embodiments, the chip may comprise a combination of the above features or any other features described herein. For example, the chip may comprise a filter, collection output, (e.g., a drain), and one or more treated surfaces to enable high seeding and harvesting efficiencies. In some cases, the combination of the filter, the collection output, (e.g., a drain), and the one or more treated surfaces may result in seeding efficiencies and/or harvesting efficiencies up to about 99% after several days of culture.

In some cases, the size of an individual chip (e.g., the surface area or volume of the chip) may be increased to maintain a target bioprocessing output while minimizing the need to multiplex and parallelize a large number of chips, which can result in lesser resistance and more manageable fabrication processes for microfluidic systems. The target bioprocessing output may comprise, for example, a total number of cells seeded or harvested for a chip, or a seeding or harvesting efficiency for a chip.

The chip designs disclosed herein may provide several advantages over other existing chip designs, such as improved seeding and harvesting efficiency. The chip designs may be configured to account for factors such as sub-optimal seeding or harvesting performance/efficiency when one dimension of the chip (e.g., a dimension of the chip along which a first operation is performed or occurs) is greater than another dimension of the chip (e.g., a dimension of the chip along which a second operation is performed or occurs). The first operation may comprise, for example, at least one of seeding, perfusion, or harvesting. The second operation may comprise, for example, at least one of seeding, perfusion, or harvesting. The first operation may be different than the second operation. In some cases, the chip designs disclosed herein may also be configured to account for losses in harvest efficiency when harvesting via one or more side channels of the chip. In any of the embodiments described herein, the chip designs may provide a harvesting location in an underlying layer of the chip to optimize harvesting efficiency.

The chips disclosed herein may provide enhanced seeding and harvesting performance compared to other chip designs. In some cases, using other chip designs may result in cells not getting captured by traps, and instead those cells may flow past the traps into one or more perfusion/feeding output channels. In some cases, when seeding a chip having a sub-optimal configuration, some of the cells provided may remain in an input channel after the seeding flow stops and the cells naturally settle down, which can result in poor seeding efficiencies. In such cases, the cells may also remain in the chip (e.g., the bioprocessing chamber of the chip) during harvesting, which can lead to poor harvesting efficiencies.

Figure 20:
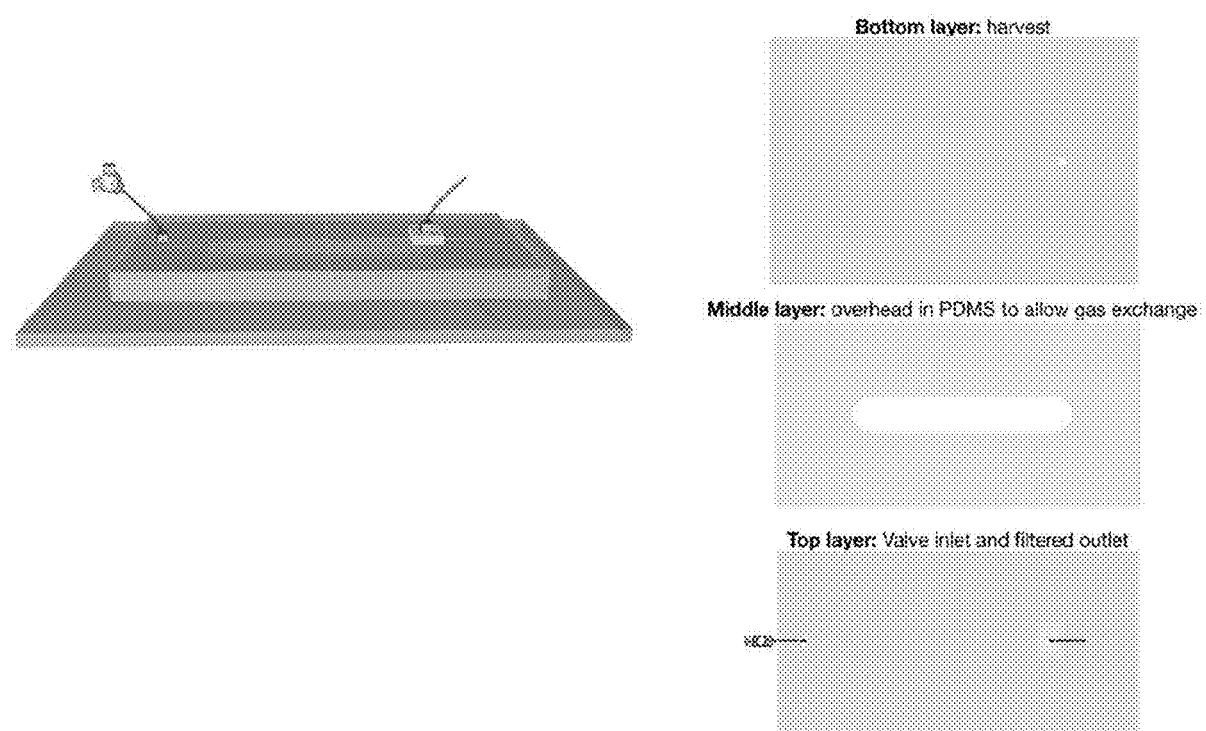
FIG. 20 schematically illustrates an example of a chip comprising a filter and a collection output for cell harvesting, in accordance with some embodiments.

FIG. 20 illustrates an example of a chip comprising a filter and a collection drain for cell harvesting. The chip may comprise a bottom layer for harvesting, a middle layer comprising an overhead in PDMS to allow gas exchange, and a top layer comprising a valve inlet and a filtered outlet. In some cases, the bottom layer may comprise milled 3 mm COC with a box harvest and hole for a connector or fitting (e.g., a 3 mm male luer fitting). In some cases, the middle layer may comprise a PDMS overhead (e.g., a 3 mm PDMS overhead). In some cases, the top layer may comprise a milled COC material (e.g., a milled 3 mm COC material) with one or more channels (e.g., a 1 mm channel) extending between the valve inlet and the filtered outlet or a hole (e.g., a 2.5 mm hole) adjacent to or in fluidic communication with the filtered outlet. In some cases, the inlet may be connected to a multi-way valve for perfusion and seeding.

FIG. 21 illustrates a series of images taken before, during, and after cell harvesting using the chip configurations described herein. The final view of the chip shows that the presently disclosed chip designs provide enhanced seeding and harvesting efficiencies/capabilities. Table 2 below shows example performance characteristics for the chip designs described herein. In some embodiments, harvesting efficiencies may be at least about 99%, and at least 93% of the harvested cells may comprise viable cells.

TABLE 2

| Attempt | % efficiency | % viability Before | % viability After |
| --- | --- | --- | --- |
| 1 | 99 | 97 | 93 |
| 2 | 99 | 95 | 93 |

In another aspect, the present disclosure provides a microfluidic system comprising one or more chips. The one or more chips may comprise one or more microfluidic chips. The one or more microfluidic chips may comprise any of the chips described herein and/or any one or more components, structures, features, or performance characteristics of the presently disclosed chips.

In some embodiments, the microfluidic system may be configured for culturing a plurality of cells in one or more bioreactors. In some cases, the plurality of cells may comprise at least about 10,000 cells. In some cases, the plurality of cells may comprise at least about 100,000 cells. In some cases, the plurality of cells may comprise at least about 1,000,000 cells or more.

In some embodiments, the microfluidic system may be configured for culturing over 20,000 cells in one or more bioreactors. In some embodiments, the microfluidic system may be configured for harvesting at least 90% of the cells in the one or more bioreactors to yield a plurality of recovered cells. The plurality of recovered cells may comprise one or more cells that are harvested from the bioprocessing chamber using any of the methods described herein. In some cases, at least 90% of the recovered cells may be viable. In some cases, at least 95%, 96%, 97%, 98%, or 99% of the recovered cells may be viable.

In some embodiments, the microfluidic system may be configured for culturing over 20,000 cells in one or more bioreactors. In some embodiments, the microfluidic system may be configured for greater than 90% cell seeding efficiency. In some cases, cell seeding may be performed at more than 90% efficiency within a target time period. In some cases, the target time period may be at most about 30 minutes, 20 minutes, 10 minutes, or less. In some cases, the target time period may be under 5 minutes. The target time period may correspond to a time duration between a first time at which seeding is initiated and a second time at which seeding ceases.

In some embodiments, the microfluidic system may be configured for homogenous cell distribution of at least 20,000 cells in a bioprocessing chamber. The bioprocessing chamber may be part of a bioreactor. Such homogenous cell distribution may comprise a spatial distribution of cells across a portion, a volume, or a surface of the bioprocessing chamber such that the density of cells distributed in a first region of the bioprocessing chamber is the same as or similar to the density of cells distributed in a second region of the bioprocessing chamber. In some cases, the density of cell distribution may correspond to a number of cells per unit area or per unit volume. In some embodiments, the density of cells distributed in the first region of the bioprocessing chamber may be within about 10%, 9%, 8%, 7%, 6%, 5%, 4%, 3%, 2%, 1%, or less of the density of cells distributed in the second region of the bioprocessing chamber. In some cases, the first region and the second region may coincide or overlap with each other. In other cases, the first region and the second region may not or need not coincide or overlap with each other.

Computer Systems

Figure 14:
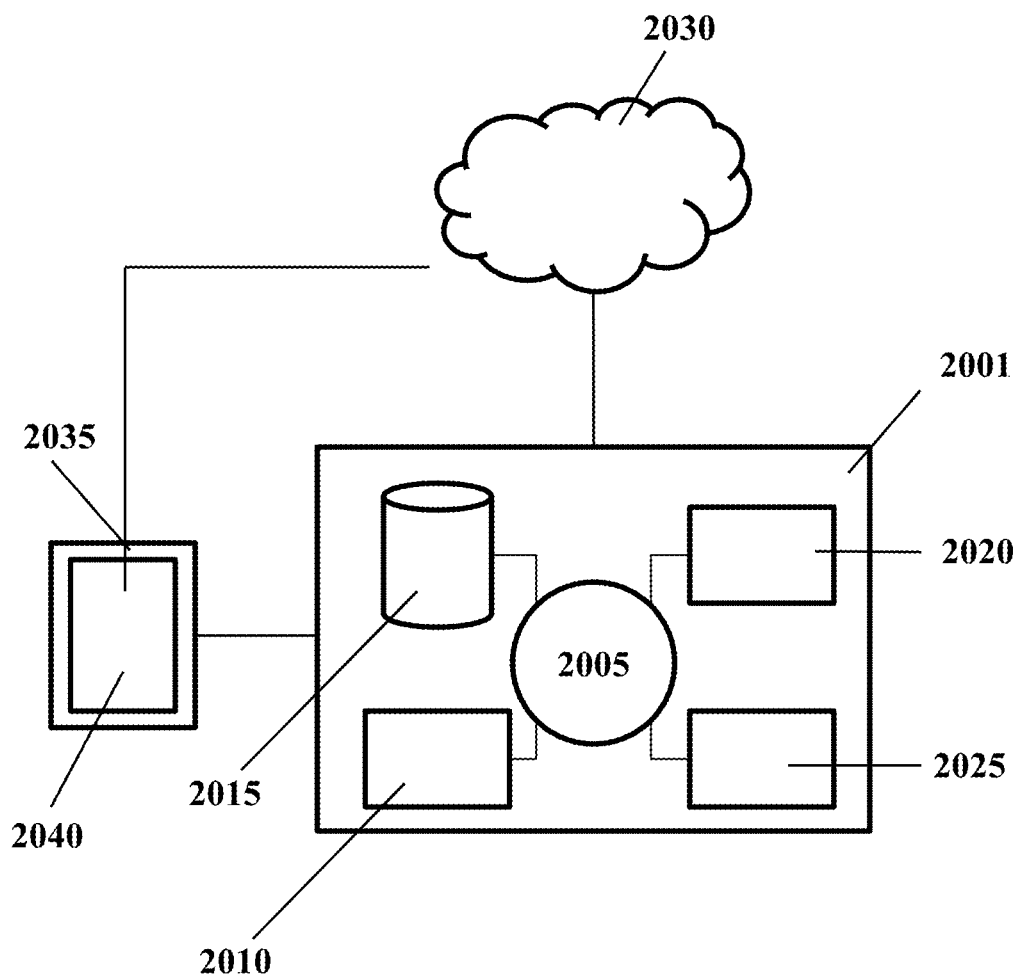
FIG. 14 schematically illustrates a computer system that is programmed or otherwise configured to implement methods provided herein.

In an aspect, the present disclosure provides computer systems that are programmed or otherwise configured to implement methods of the disclosure, e.g., any of the subject methods for bioprocessing. FIG. 14 shows a computer system 2001 that is programmed or otherwise configured to implement a method for bioprocessing. The computer system 2001 can be configured to, for example, control a flow of fluid comprising one or more cells into or through one or more chips. In some cases, the computer system 2001 can be configured to adjust a flow rate or an amount of fluid flow into or through the one or more chips, based on one or more sensor readings. The computer system 2001 can be further configured to adjust the flow rate or an amount of fluid flow into or through the one or more chips in order to optimize (i.e., decrease) an amount of pressure drop across the system. The computer system 2001 can be an electronic device of a user or a computer system that is remotely located with respect to the electronic device. The electronic device can be a mobile electronic device.

The computer system 2001 can include a central processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data. The computer system 2001 can be operatively coupled to a computer network ("network") 2030 with the aid of the communication interface 2020. The network 2030 can be the Internet, an internet and/or extranet, or an intranet and/or extranet that is in communication with the Internet. The network 2030 in some cases is a telecommunication and/or data network. The network 2030 can include one or more computer servers, which can enable distributed computing, such as cloud computing. The network 2030, in some cases with the aid of the computer system 2001, can implement a peer-to-peer network, which can enable devices coupled to the computer system 2001 to behave as a client or a server.

The CPU 2005 can execute a sequence of machine-readable instructions, which can be embodied in a program or software. The instructions can be stored in a memory location, such as the memory 2010. The instructions can be directed to the CPU 2005, which can subsequently program or otherwise configure the CPU 2005 to implement methods of the present disclosure. Examples of operations performed by the CPU 2005 can include fetch, decode, execute, and writeback.

The CPU 2005 can be part of a circuit, such as an integrated circuit. One or more other components of the system 2001 can be included in the circuit. In some cases, the circuit is an application specific integrated circuit (ASIC).

The storage unit 2015 can store files, such as drivers, libraries and saved programs. The storage unit 2015 can store user data, e.g., user preferences and user programs. The computer system 2001 in some cases can include one or more additional data storage units that are located external to the computer system 2001 (e.g., on a remote server that is in communication with the computer system 2001 through an intranet or the Internet).

The computer system 2001 can communicate with one or more remote computer systems through the network 2030. For instance, the computer system 2001 can communicate with a remote computer system of a user (e.g., an operator managing or monitoring the bioprocessing). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2001 via the network 2030.

Methods as described herein can be implemented by way of machine (e.g., computer processor) executable code stored on an electronic storage location of the computer system 2001, such as, for example, on the memory 2010 or electronic storage unit 2015. The machine executable or machine-readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2001, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media including, for example, optical or magnetic disks, or any storage devices in any computer(s) or the like, can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 2001 can include or be in communication with an electronic display 2035 that comprises a user interface (UI) 2040 for providing, for example, a portal for an operator to monitor or track one or more steps or operations of the bioprocessing methods and systems described herein. The portal can be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2005. For example, the algorithm can be configured to adjust a flow rate or an amount of fluid flow into or through the one or more chips, based on one or more sensor readings. In some embodiments, the algorithm can be further configured to adjust the flow rate or an amount of fluid flow into or through the one or more chips in order to optimize (i.e., decrease) an amount of pressure drop across the system.

Figure 22:
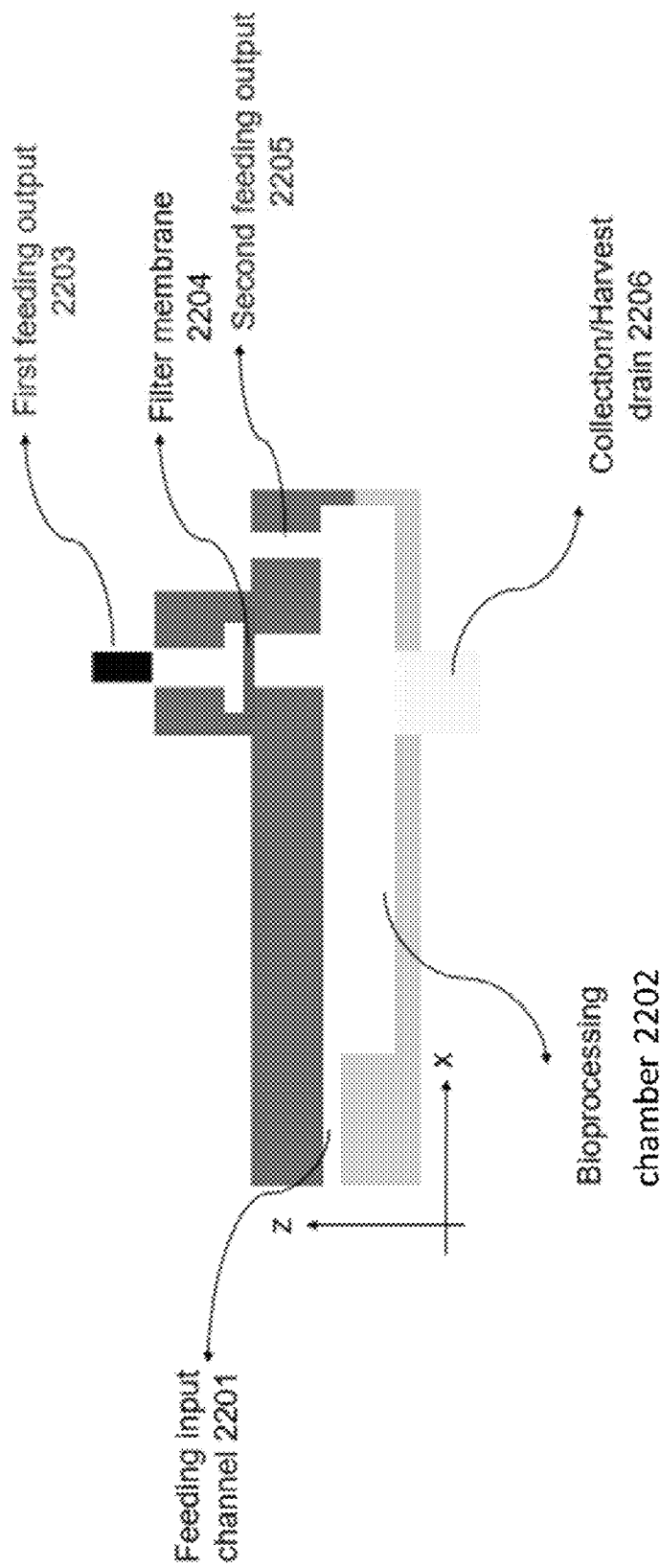
FIG. 22 schematically illustrates a chip comprising a first feeding output and a second feeding output, in accordance with some embodiments.

FIG. 22 schematically illustrates a chip comprising a feeding input channel 2201 and a bioprocessing chamber 2202. In some cases, the chip comprises a first feeding output 2203 and a second feeding output 2205. In some cases, the first feeding output 2203 and the second feeding output 2205 are located at a top portion of the chip. In some cases, the chip comprises a filter membrane 2204 for regulating a flow through the first feeding output 2203. In some cases, the second feeding output 2205 is used in case the first feeding output 2203 is clogged by cells (e.g., due to loss of or decrease in filter functionality, efficiency, or performance over time). In some cases, the chip comprises a collection/harvest drain 2206 disposed at or near a bottom portion of the chip or the bioprocessing chamber of the chip.

Figure 23:
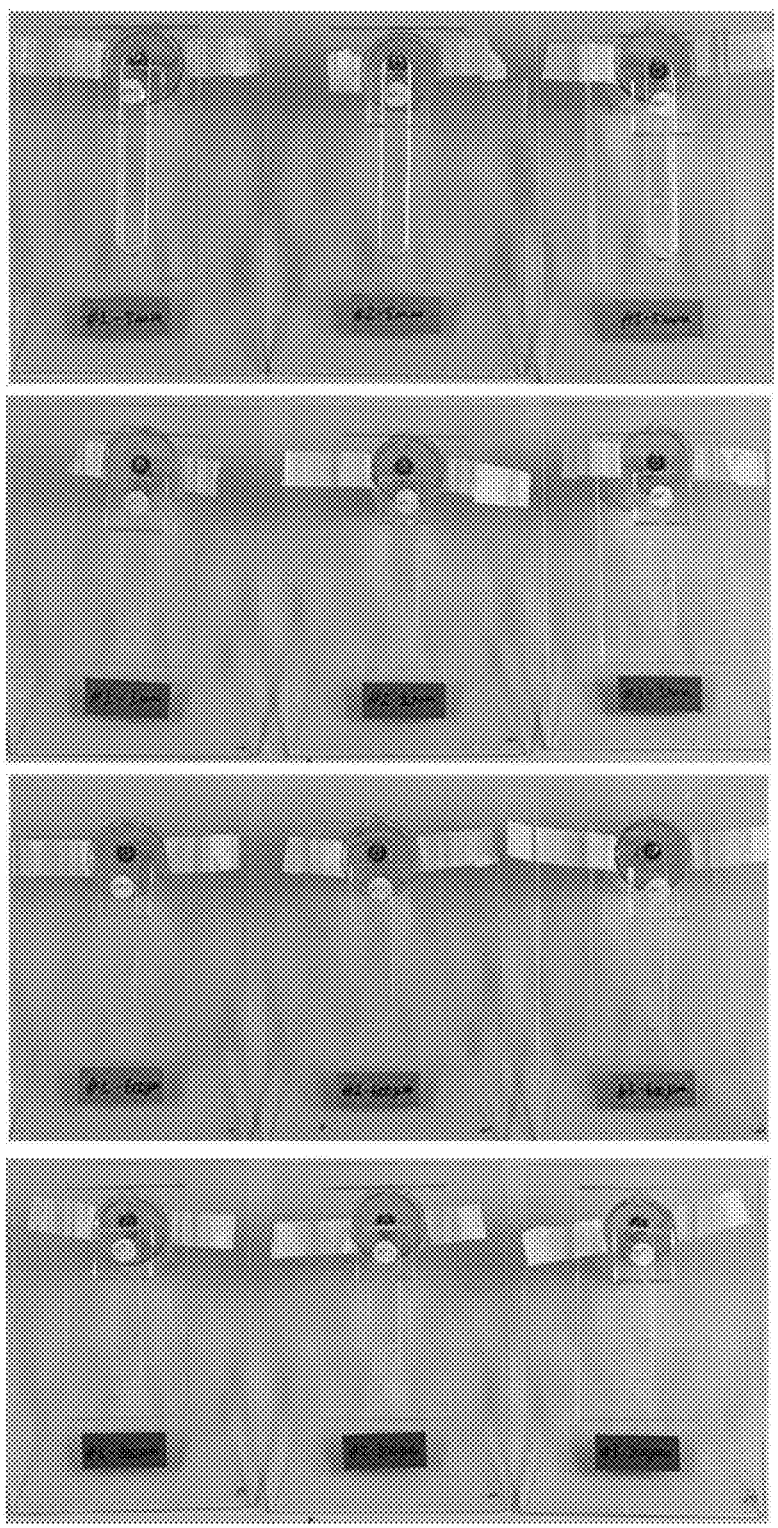
FIG. 23 schematically illustrates a plurality of chips comprising different overhead heights, in accordance with some embodiments.

FIG. 23 schematically illustrates a plurality of chips that can be used to implement the systems and methods of the present disclosure. In some cases, the chips comprise different overhead heights. In some cases, the overhead heights range from about 10 mm to about 100 µm. In some cases, the chips have an overhead height of about 5 mm, 1 mm, 600 µm, or 300 µm. In some cases, the chips have an overhead height that is greater than about 5 mm. In some cases, the chips have an overhead height that is less than about 300 µm. In some cases, the overhead height of the chips correspond to a height of the bioprocessing chamber or a distance between a bottom portion of the bioprocessing chamber and an upper portion of the bioprocessing chamber (e.g., the ceiling of the bioprocessing chamber).

Figure 24:
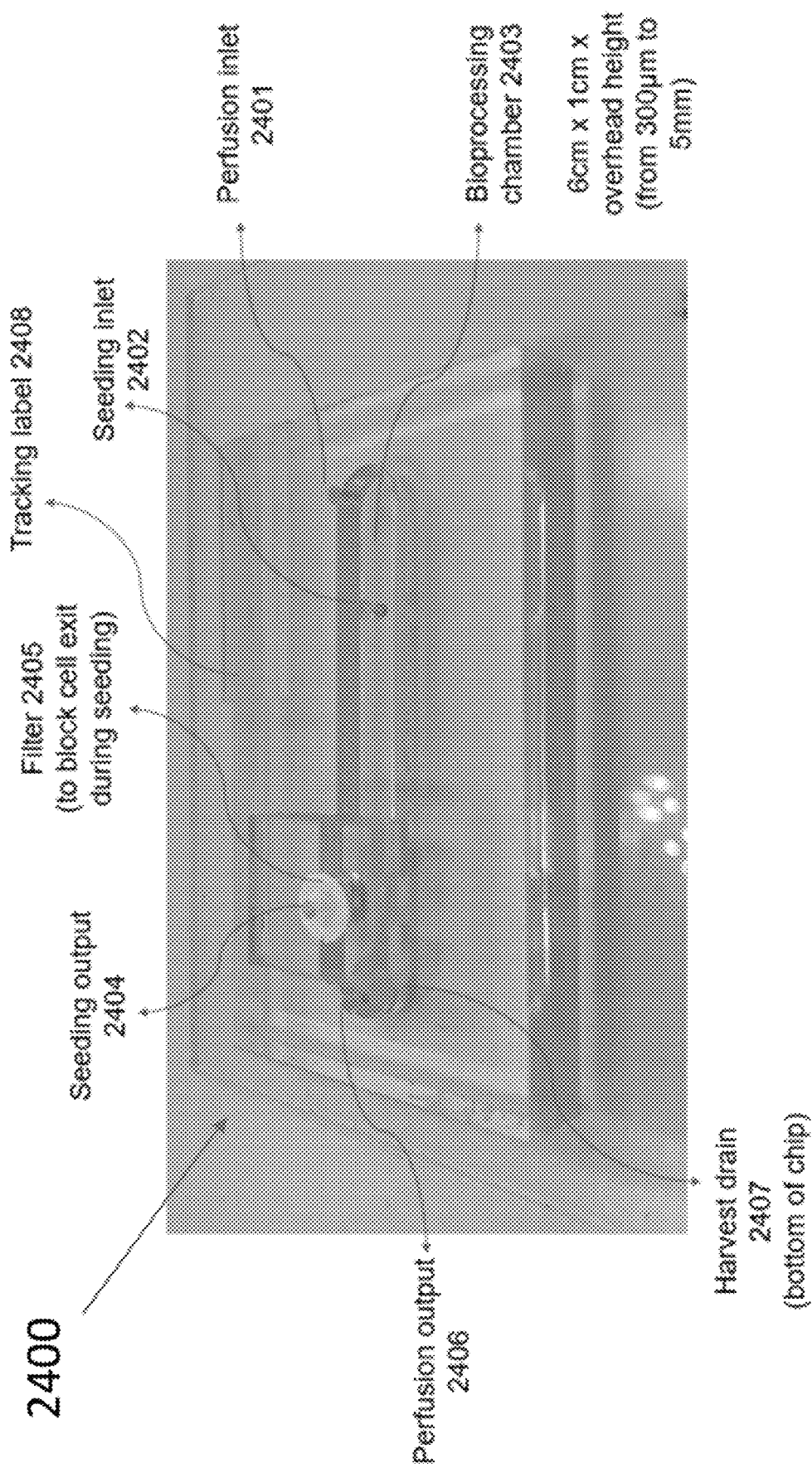

FIG. 24 schematically illustrates various components of an exemplary chip 2400, in accordance with some embodiments. FIG. 25 schematically illustrates a top view and a bottom view of the chip 2400 shown in FIG. 24. As shown in FIG. 24, the chip 2400 comprises a perfusion inlet 2401 and a seeding inlet 2402. The chip 2400 further comprises a bioprocessing chamber 2403 in fluidic communication with the perfusion inlet 2401 and the seeding inlet 2402. In some cases, the bioprocessing chamber 2403 has dimensions of about 6 cm by about 1 cm, and an overhead height ranging from about 300 µm to about 5 mm. In some cases, the chip 2400 further comprises a seeding output 2404, a filter 2405 for blocking an exit flow of cells during seeding, and a perfusion output 2406. The seeding output 2404 is in fluidic communication with the seeding inlet 2402 via the bioprocessing chamber 2403. The perfusion output 2406 is in fluidic communication with the perfusion inlet 2401 via the bioprocessing chamber 2403. In some cases, the chip 2400 further comprises a collection/harvest drain 2407 that is located on or near a bottom portion of the chip 2400 or the bioprocessing chamber 2403 of the chip 2400. In some non-limiting embodiments, the chip 2400 comprises a tracking label 2408 that is affixable to a portion or a surface of the chip 2400.

Figure 26A:
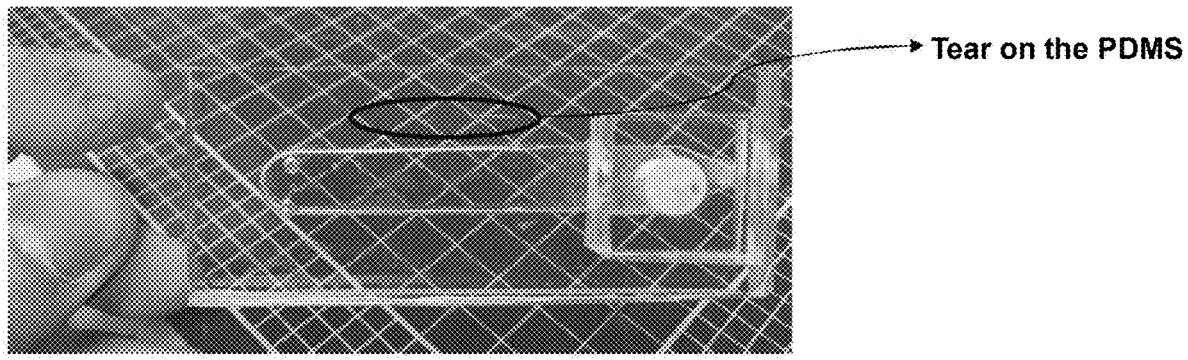
FIGS. 26A-26B and 27A schematically illustrate tears or fractures that may occur in a bioprocessing chamber when a chip experiences high fluid pressures.
Figure 26B:
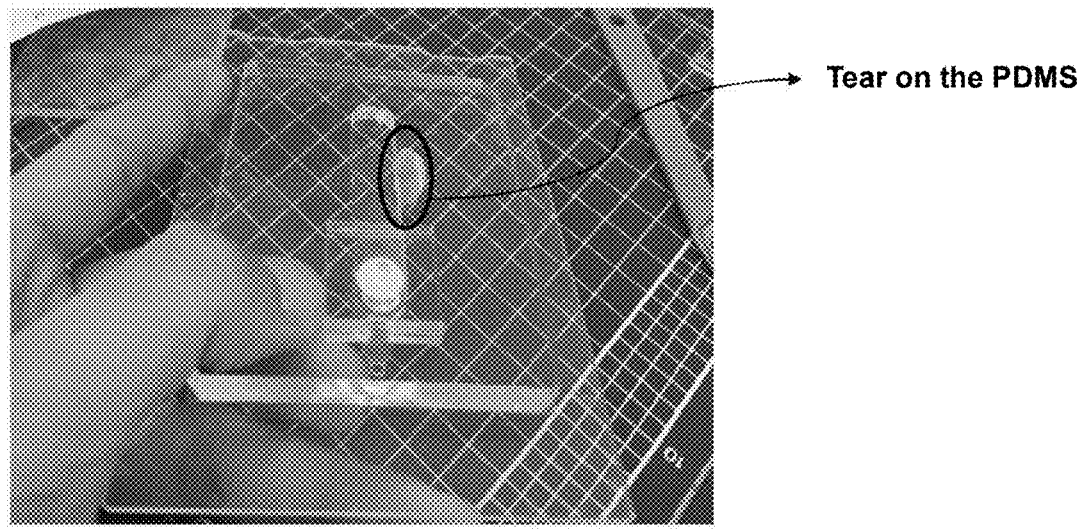
Figure 27A:
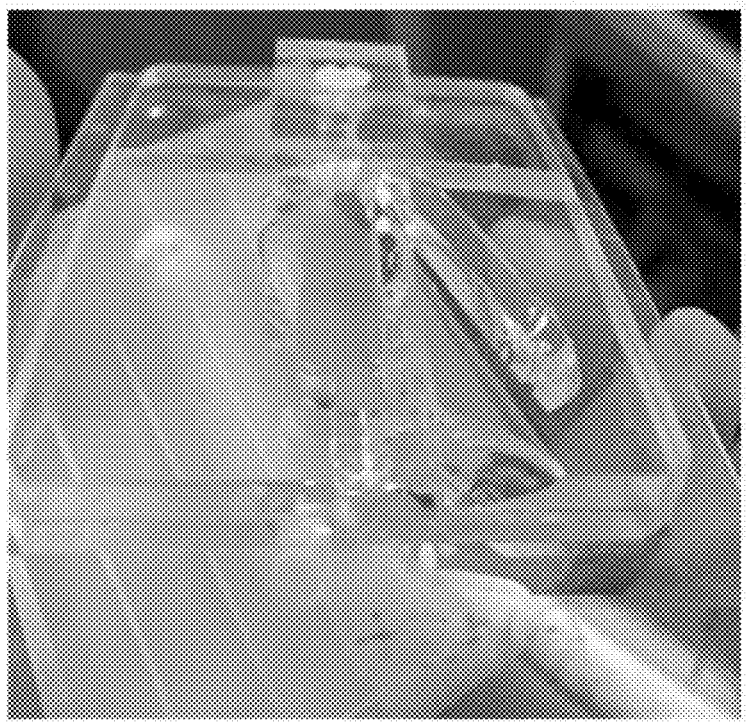

FIGS. 26A-26B and 27A schematically illustrate tears or fractures that may occur in a bioprocessing chamber when a chip experiences high fluid pressures. FIG. 26A shows a first angle of a chip and a tear. FIG. 26B shows a second angle of the chip and tear, in which the tear is more visible. In some cases, due to a flow of fluid and/or particles through the chip or the bioprocessing chamber of the chip, one or more tears or fractures can form in the body of the chip or a portion of the bioprocessing chamber. In some cases, the one or more tears or fractures may occur at an angle relative to an axis extending along a dimension (e.g., a length or a width) of the chip or the bioprocessing chamber. In some cases, the angle ranges from 1 degree to 90 degrees.

Figure 27B:
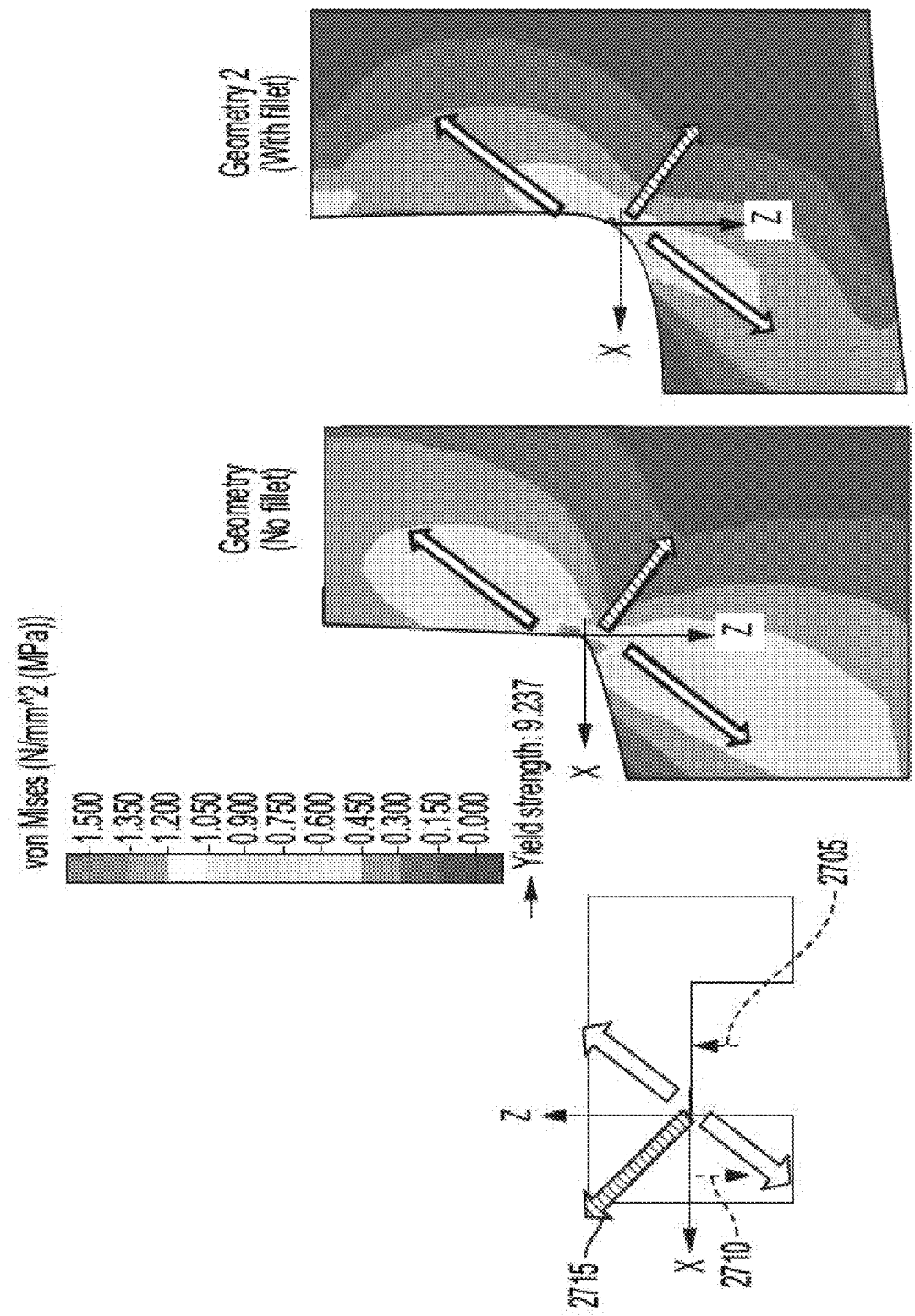
FIG. 27B schematically illustrates forces that can be exerted on the bioprocessing chamber when a chip experiences high fluid pressures.

FIG. 27B schematically illustrates forces that can be exerted on the bioprocessing chamber when a chip experiences high fluid pressures. In some embodiments, fluid pressure inside the bioprocessing chamber may exert stress in a first direction (e.g., upwards as shown at 2705), while the bonding between various layers of the chip exerts stress in a second direction (e.g., downwards as shown at 2710). The resultant net force can be represented as a vector oriented at an angle relative to the first direction and/or the second direction (e.g., diagonally as show at 2715). Simulated stress is shown for two different geometries, one with no fillet and another with a fillet and demonstrate a difference in the magnitude of stress with or without a fillet. As shown in FIG. 27B, stress levels in the vicinity of the fillet are lower than with no fillet present. The effect of the fillet may reduce the stress concentration of the corner. The direction of the principle stress vectors may indicate that a crack would be expected to propagate at approximately 45° to the horizontal, as shown by the filled arrow. Principle stress vectors, indicated by unfilled arrows, are approximately 45° to the horizontal, and may result in a crack propagating in a direction orthogonal to the unfilled arrows, as indicated by the filled arrow.

Figure 28:
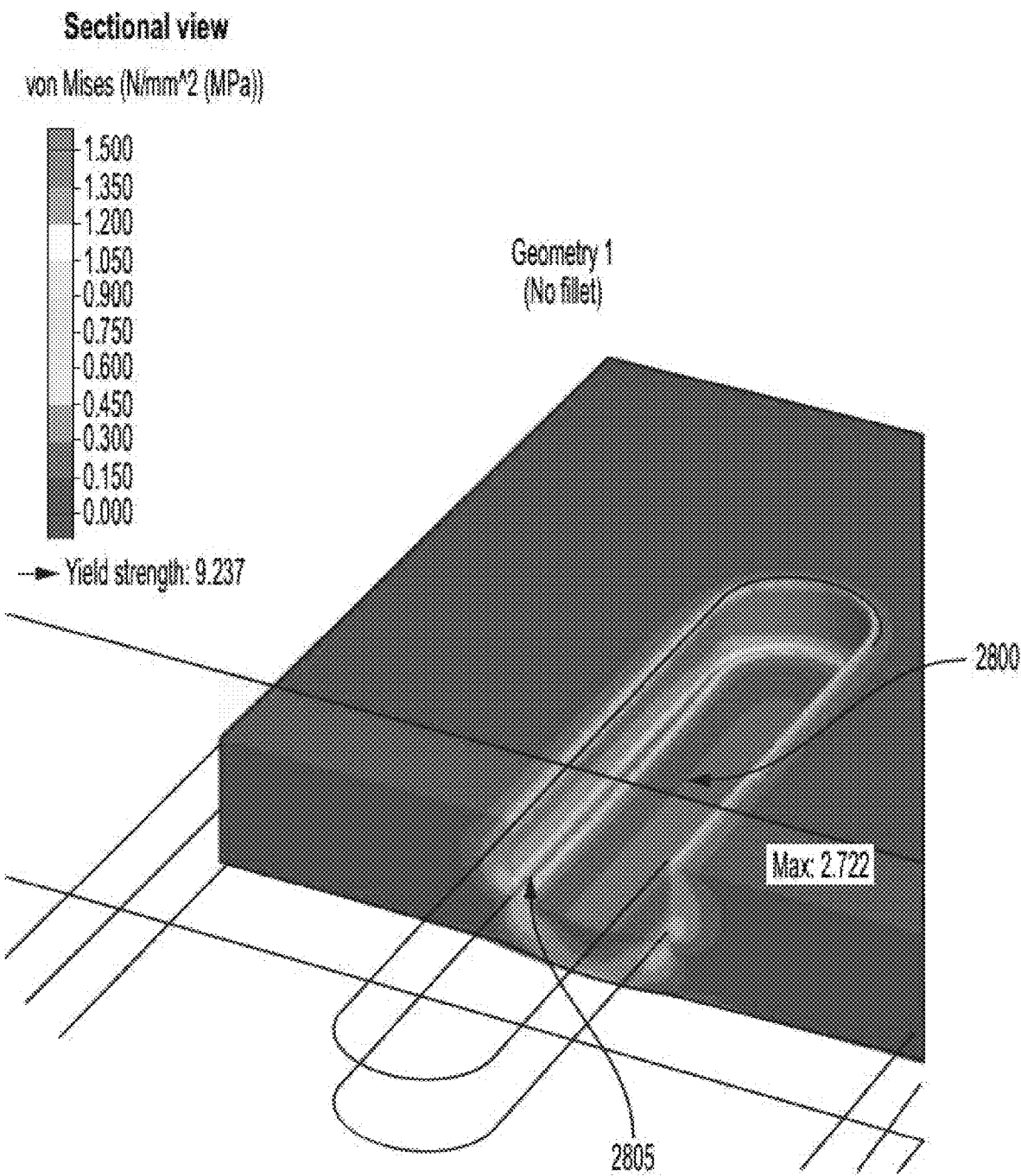
FIG. 28 schematically illustrates a stress that can be exerted on a bioprocessing chamber of a chip that does not comprise a fillet in the bioprocessing chamber.

FIG. 28 schematically illustrates a stress that can be exerted on a bioprocessing chamber of a chip that does not comprise a fillet in the bioprocessing chamber. The stress exerted on the bioprocessing chamber 2800 may be greatest at or near an internal corner and a mid-span of an edge of the bioprocessing chamber. The stress simulated in FIG. 28 corresponds to a Von-Mises stress, which is a value used to determine if a given material (e.g., the material forming the bioprocessing chamber or a portion thereof) will yield or fracture. As shown at 2805, the Von-Mises stress was predicted to be the greatest as the internal corner and at the mid-span of the edge at approximately 2.7 MPa.

Figure 29:
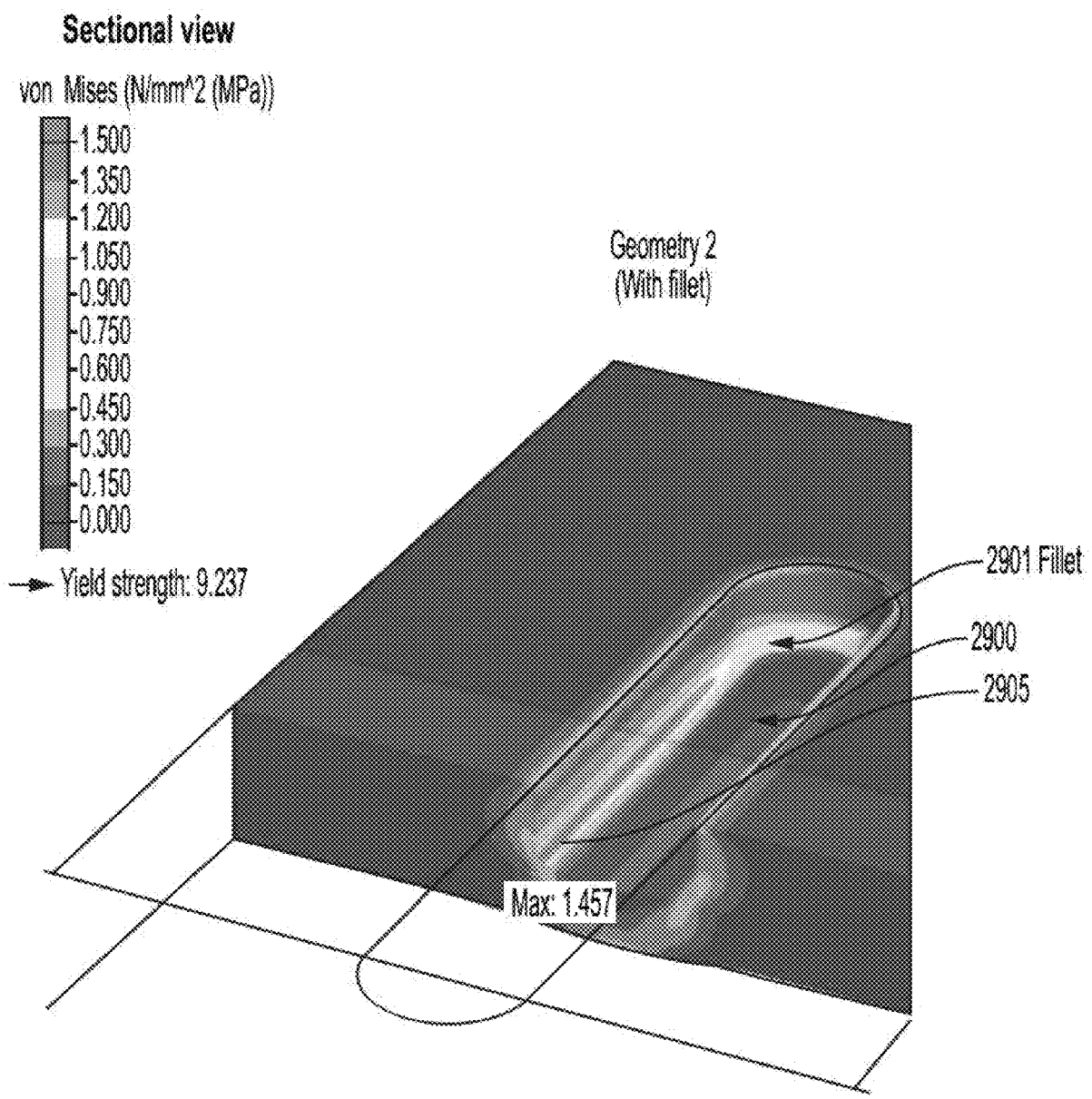
FIG. 29 schematically illustrates a stress that can be exerted on a bioprocessing chamber of a chip that does comprise a fillet in the bioprocessing chamber.

FIG. 29 schematically illustrates a stress that can be exerted on a bioprocessing chamber of a chip that comprises a fillet in the bioprocessing chamber. In some embodiments, a fillet 1901 is provided to prevent tears in the bioprocessing chamber 2900 due to potential pressure build-up due to fluid flow through the chip. In some cases, the fillet comprises a rounding of an interior or exterior corner or edge of the bioprocessing chamber or a portion thereof. The Von-Mises stress on the bioprocessing chamber of a chip comprising a filleted geometry (e.g., a 1 mm fillet) is approximately half of the stress exerted on an internal corner of a chip that does not comprise a filleted geometry in the bioprocessing chamber, for a same applied fluid pressure. The introduction of the fillet reduces the stress exerted on portions or surfaces of the bioprocessing chamber, and minimizes the chances of tears or fractures developing in the chip or the bioprocessing chamber due to fluid pressure or fluid flow through the chip or the bioprocessing chamber. As shown at 2905, the Von- Mises stress was predicted to be the greatest at the fillet and at the mid-span of the fillet at approximately 1.45 MPa.

Figure 30:
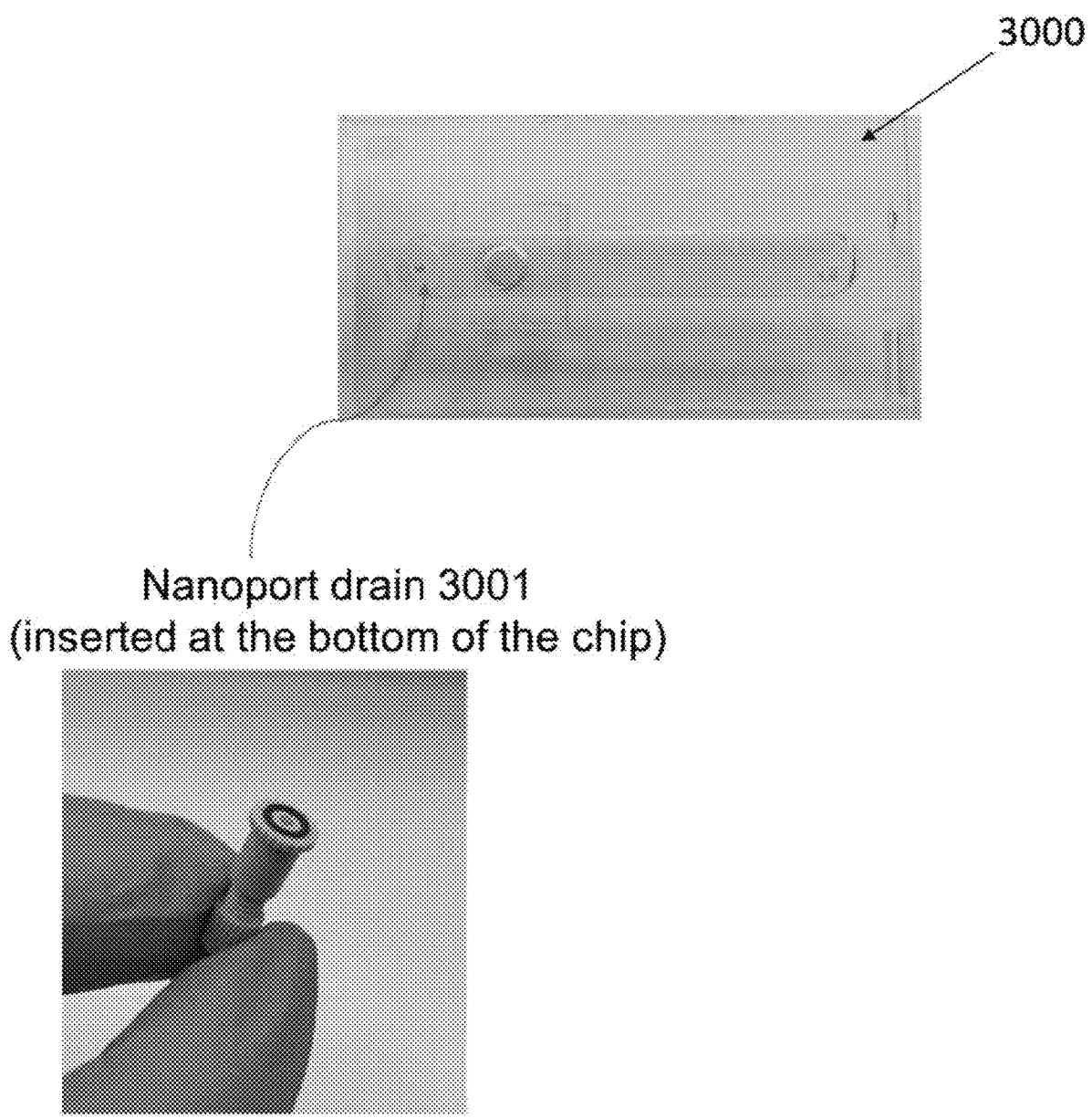
FIG. 30 schematically illustrates an exemplary configuration for a collection drain, in accordance with some embodiments.

FIG. 30 schematically illustrates an exemplary configuration for a collection drain, in accordance with some embodiments. In some cases, the collection drain comprises a nano port that is insertable into or provided on a bottom portion or region of the chip to form a tight fit. In some embodiments, the nano port comprises a port, a hole, or an aperture that is sized in the nanometer range. For example, in some cases, the nano port comprises a port, a hole, or an aperture having a diameter that is between about 1 nm and about 1000 nm.

Figure 31:
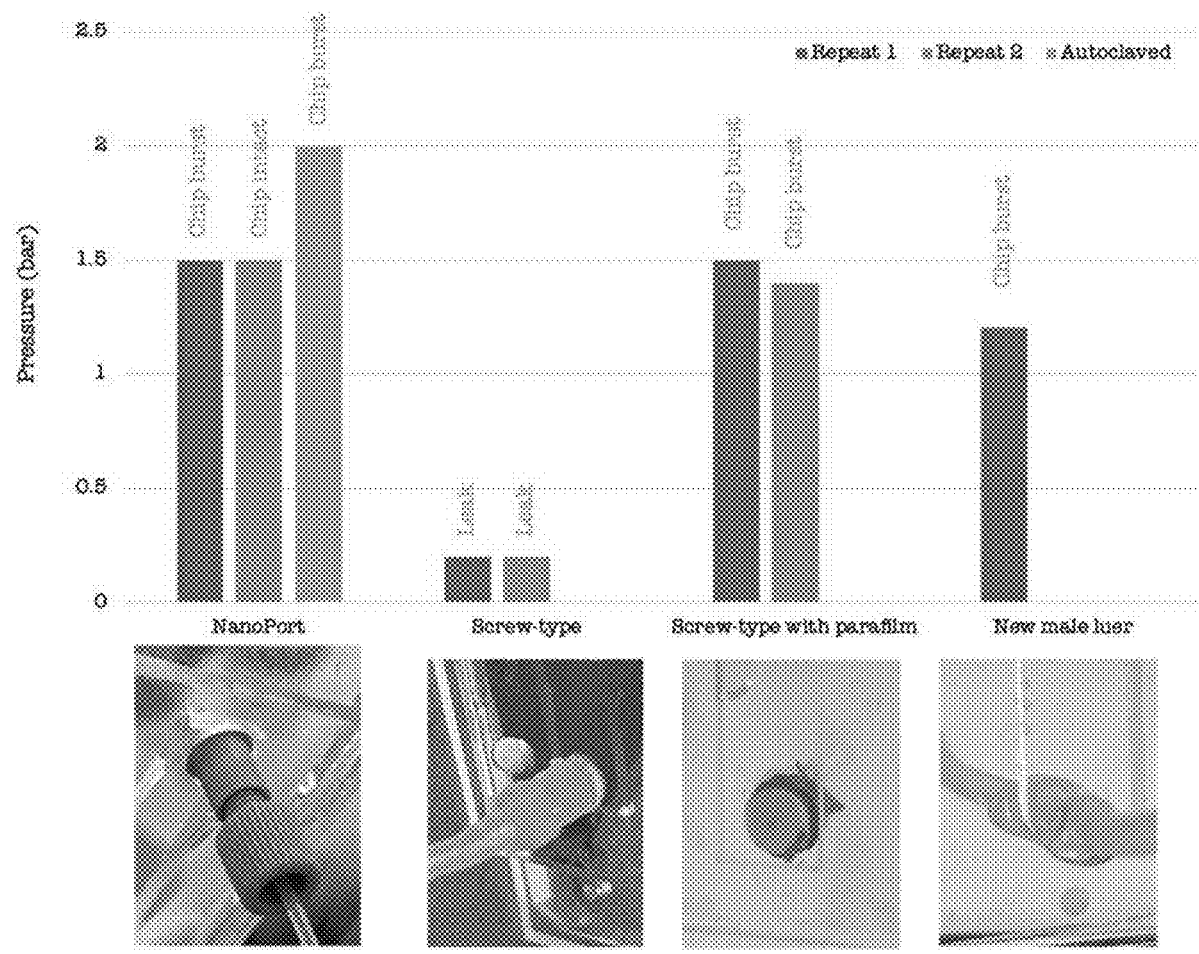
FIG. 31 schematically illustrates a comparison of pressure tests for different collection drain connector designs and configurations.

FIG. 31 schematically illustrates a comparison of pressure tests for different collection drain connector designs/configurations. The nano port design as described above with reference to FIG. 30 provides a consistent resistance to burst pressure even after autoclave, while other connectors are not capable of withstanding autoclave.

Figure 32A:
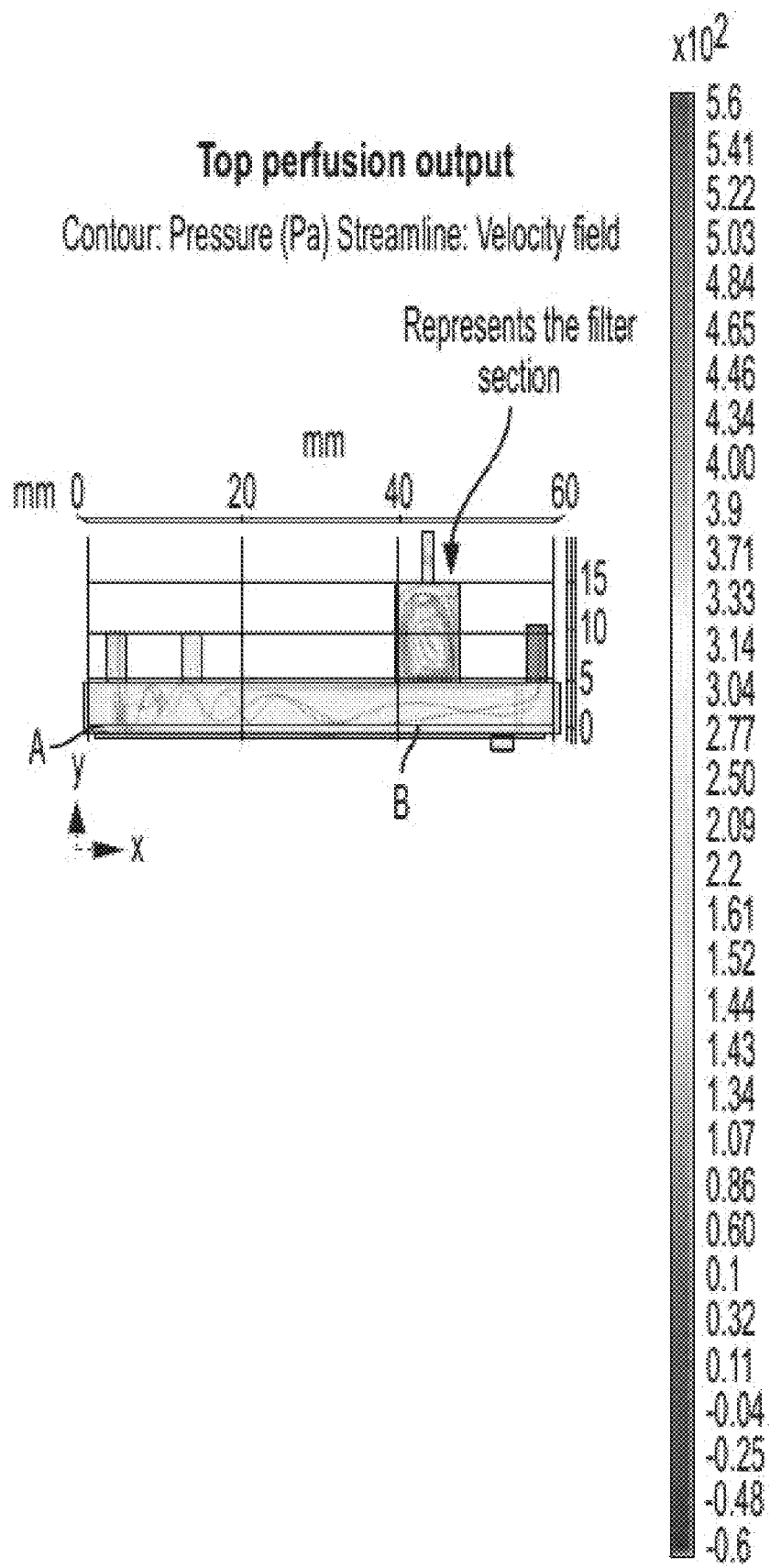
FIG. 32A-32B schematically illustrates simulations showing the differences in fluid streamlines based on the perfusion output position.
Figure 32B:
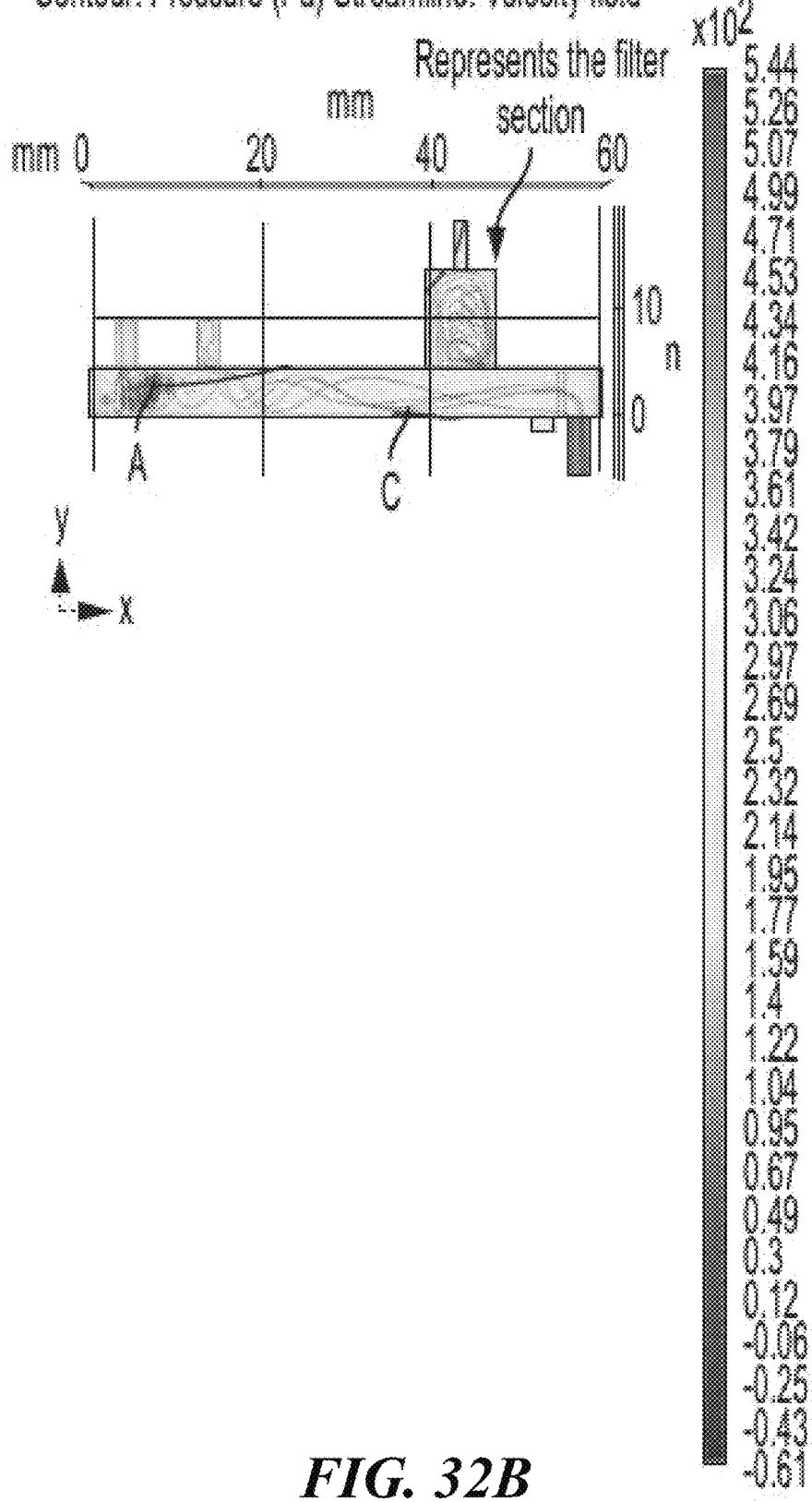

FIG. 32A-32B schematically illustrates simulations showing the difference in fluid streamlines based on the perfusion output position. The FIG. 32A illustrates a chip design comprising a perfusion output located at a top portion of the bioprocessing chamber, and FIG. 32B illustrates a chip design comprising a perfusion output located at a bottom portion of the bioprocessing chamber. In both cases, as indicated by reference character A, entry streamlines create eddies (i.e., turbulent sections), though at the same flow conditions, the entry streamlines are more chaotic when the perfusion output is located at the bottom of the bioprocessing chamber. As indicated by reference character B, when the perfusion output is at the top of the bioprocessing chamber, perfusion streamlines are less dense, resulting in less shear stress on the cells. As indicated by reference character C, when the perfusion output is at the bottom of the bioprocessing chamber, the perfusion streamlines are denser and more turbulent, which can be detrimental to cell growth and retention during perfusion due to higher shear stress. Thus, providing a perfusion output at the top portion of the bioprocessing chamber is more efficient than providing a perfusion output at the bottom portion of the bioprocessing chamber, due to less turbulence during fluid flow as well as fewer fluid streamlines impacting the cells in the bioprocessing chamber.

EMBODIMENTS

The following enumerated embodiments are provided.

Embodiment 1. A solid support, comprising:
a microfluidic feeding input channel;
a bioprocessing chamber comprising a bottom surface, wherein the bioprocessing chamber is fluidically connected to the feeding input channel; and
a collection output fluidically connected to the bioprocessing chamber via the bottom surface.

Embodiment 2. The solid support of embodiment 1, wherein the collection output is not orthogonal to the bottom surface.

Embodiment 3. The solid support of embodiment 1, wherein the collection output is orthogonal to the bottom surface.

Embodiment 4. The solid support of embodiment 1, wherein a flow path comprising the microfluidic feeding input channel, the bioprocessing chamber and the collection output is closed during a seeding or perfusion operation.

Embodiment 5. The solid support of embodiment 1, wherein the bioprocessing chamber is elongated and comprises a first end wall and a second end wall opposite the first end wall, and wherein the bottom surface of the bioprocessing chamber is substantially orthogonal to the first end wall and the second end wall.

Embodiment 6. The solid support of embodiment 5, wherein the microfluidic feeding input channel is fluidically connected to the first end wall of the bioprocessing chamber and the collection output is fluidically connected to the bottom surface nearer the second wall end of the bioprocessing chamber than the first end wall.

Embodiment 7. The solid support of embodiment 1, wherein the solid support does not comprise a valve that regulates fluid flow from the bioprocessing chamber into the collection output.

Embodiment 8. A solid support, comprising:
a bioprocessing chamber comprising a bottom surface; and
a collection output fluidically connected to the bioprocessing chamber via the bottom surface, wherein the solid support comprises no valve that regulates fluid flow from the bioprocessing chamber into the collection output.

Embodiment 9. The solid support of embodiment 8, wherein the collection output is not orthogonal to the bottom surface.

Embodiment 10. The solid support of embodiment 8, wherein the collection output is orthogonal to the bottom surface.

Embodiment 11. A solid support comprising
a bioprocessing chamber comprising a ceiling;
a feeding output channel fluidically connected to the bioprocessing chamber via the ceiling; and a filter that selectively prevents solid particles from passing from the bioprocessing chamber to the feeding output channel.

Embodiment 12. The solid support of embodiment 11, wherein the filter comprises a filter membrane that comprises a hydrophilic material, optionally, wherein the hydrophilic material comprises polyethersulfone (PES), polycarbonate, or polyester.

Embodiment 13. The solid support of embodiment 11, wherein the filter comprises a filter membrane that comprises a pore size of less than 10 μm, less than 7.5 μm, less than 5 μm, or less than 2.5 μm.

Embodiment 14. The solid support of embodiment 11, wherein the filter comprises a filter membrane that is rectangular or circular.

Embodiment 15. The solid support of embodiment 11, further comprising a microfluidic feeding input channel, wherein the bioprocessing chamber is fluidically coupled to the microfluidic feeding input channel.

Embodiment 16. The solid support of embodiment 15, wherein a flow path comprising the microfluidic feeding input channel, the bioprocessing chamber, and the feeding output channel is closed.

Embodiment 17. The solid support of embodiment 16, wherein the bioprocessing chamber is elongated and comprises a first end wall and a second end wall opposite the first end wall, and wherein the ceiling of the bioprocessing chamber is substantially orthogonal to the first end wall and the second end wall.

Embodiment 18. The solid support of embodiment 17, wherein the microfluidic feeding input channel is fluidically connected to the first end wall of the bioprocessing chamber and feeding output channel is fluidically connected to the ceiling nearer the second wall end of the bioprocessing chamber than the first end wall.

Embodiment 19. A solid support comprising
a bioprocessing chamber comprising a bottom surface and a ceiling;
a collection output fluidically connected to the bioprocessing chamber via the bottom surface of the bioprocessing chamber; and
a feeding output channel fluidically connected to the bioprocessing chamber via the ceiling.

Embodiment 20. The solid support of embodiment 19, wherein the collection output is positioned directly below the feeding output channel.

Embodiment 21. The solid support of embodiment 19, wherein the collection output is not positioned directly below feeding output channel.

Embodiment 22. The solid support of embodiment 19, further comprising a filter membrane that selectively prevents solid particles from passing from the bioprocessing chamber to the feeding output channel.

Embodiment 23. The solid support of embodiment 19, further comprising a feeding input channel, wherein the bioprocessing chamber is fluidically connected to the feeding input channel.

Embodiment 24. The solid support of embodiment 23, wherein the feeding input channel is a single channel.

Embodiment 25. The solid support of embodiment 23, wherein the feeding input channel comprises a plurality of feeding input channels.

Embodiment 26. The solid support of embodiment 25, wherein the plurality of feeding input channels comprises a binary tree network.

Embodiment 27. The solid support of embodiment 23, further comprising a feeding input fluidically connected to the feeding input channel.

Embodiment 28. The solid support of embodiment 27, wherein the feeding input is one feeding input.

Embodiment 29. The solid support of embodiment 27, wherein the feeding input comprises a plurality of feeding inputs.

Embodiment 30. The solid support of embodiment 23, wherein the feeding input channel comprises a length dimension parallel to a length dimension of the bioprocessing chamber.

Embodiment 31. The solid support of embodiment 23, wherein the bottom surface is on a first plane, wherein the feeding input channel is on a second plane, wherein the first plane and the second plane are different, and the first plane is below the second plane.

Embodiment 32. The solid support of embodiment 19, wherein a length dimension of the bioprocessing chamber is at least 2×, 3×, 4×, 5×, 10×, 15×, or 20× a width dimension of the bioprocessing chamber.

Embodiment 33. The solid support of embodiment 19, wherein the bioprocessing chamber comprises a curved edge.

Embodiment 34. The solid support of embodiment 33, wherein the curved edge is at an end of bioprocessing chamber.

Embodiment 35. The solid support of embodiment 19, wherein the bottom surface comprises a material that is U.S. Pharmacopeia (USP) Class VI and ISO 10993 compliant.

Embodiment 36. The solid support of embodiment 19, the bottom surface comprises cyclic olefin copolymer (COC).

Embodiment 37. The solid support of embodiment 19, wherein the bioprocessing chamber comprises a wall.

Embodiment 38. The solid support of embodiment 37, wherein the wall comprises cyclic olefin copolymer (COC).

Embodiment 39. The solid support of embodiment 19, wherein the ceiling comprises a gas permeable material, optionally, wherein the gas permeable material is polydimethylsiloxane (PDMS), or a cyclic olefin copolymer (COC) membrane, optionally wherein the COC membrane has a thickness of about 100 μm.

Embodiment 40. The solid support of embodiment 19, wherein the bioprocessing chamber comprises a height of at least 0.1 mm, 0.2 mm, 0.3 mm, 0.4 mm, or 0.5 mm.

Embodiment 41. The solid support of embodiment 19, wherein the bioprocessing chamber is treated with a coating.

Embodiment 42. The solid support of embodiment 41, wherein the coating interacts with or adheres to the bottom surface via curing or incubation.

Embodiment 43. A system comprising the solid support of any one of embodiments 1-42 coupled to an agitation device.

Embodiment 44. A method, comprising:

providing the solid support of any of embodiments 1-7; and flowing a fluid through the microfluidic feeding input channel and the bioprocessing chamber.

Embodiment 45. The method of embodiment 44, wherein the fluid comprises solid particles.

Embodiment 46. The method of embodiment 45, further comprising seeding the solid particles in the bioprocessing chamber, thereby providing seeded solid particles.

Embodiment 47. The method of embodiment 46, further comprising agitating the solid support to homogenously distribute the solid particles in the bioprocessing chamber.

Embodiment 48. The method of embodiment 47, wherein the seeded solid particles comprise cells.

Embodiment 49. The method of embodiment 48, further comprising expanding the cells in the bioprocessing chamber.

Embodiment 50. The method of embodiment 49, further comprising harvesting the expanded cells through the collection output.

Embodiment 51. The method of embodiment 50, wherein the harvesting comprises using positive pressure, negative pressure, or both.

Embodiment 52. A method, comprising:

providing the solid support of any one of embodiments 11-16;

flowing a fluid through the bioprocessing chamber and a feeding output channel fluidically connected to the bioprocessing chamber.

Embodiment 53. The method of embodiment 52, wherein the fluid comprises the solid particles, and the solid particles comprise cells.

Embodiment 54. The method of embodiment 53, wherein the filter membrane prevents the cells from entering the feeding output channel during seeding or perfusion.

Embodiment 55. The method of embodiment 54, wherein the cells comprise human cells.

Embodiment 56. A method, comprising:
providing the solid support of any of embodiments 19-42; and flowing a fluid through the bioprocessing chamber and the feeding output channel.

Embodiment 57. The method of embodiment 56, wherein the fluid comprises solid particles.

Embodiment 58. The method of embodiment 57, wherein the solid particles comprise cells.

Embodiment 59. The method of embodiment 58, further comprising seeding the cells in the bioprocessing chamber, thereby providing seeded cells.

Embodiment 60. The method of embodiment 59, wherein, during the flowing, the cells do not enter the collection output or the feeding output channel.

Embodiment 61. The method of embodiment 59, further comprising contacting the seeded cells with a reagent.

Embodiment 62. A microfluidic system comprising one or more bioprocessing chambers, wherein the system is configured for i) culturing over 20,000 cells in the one or more bioprocessing chambers and ii) harvesting at least 90% of the cells to yield recovered cells, wherein at least 90% of the recovered cells are viable.

Embodiment 63. The microfluidic system of embodiment 62, further comprising a feeding input channel, wherein the one or more bioprocessing chambers are fluidically connected to the feeding input channel.

Embodiment 64. The microfluidic system of embodiment 62, further comprising one or more collection outputs fluidically connected to the one or more bioprocessing chambers.

Embodiment 65. The microfluidic system of embodiment 64, wherein the one or more collection outputs are fluidically connected to the one or more bioprocessing chambers via a bottom surface of the one or more bioprocessing chambers.

Embodiment 66. The microfluidic system of embodiment 62, further comprising one or more filters that selectively prevent solid particles from passing from the one or more bioprocessing chambers to a feeding output channel of the microfluidic system.

Embodiment 67. A microfluidic system comprising one or more bioprocessing chambers, wherein the microfluidic system is configured for: i) culturing over 20,000 cells in the one or more bioprocessing chambers, ii) at greater than 90% cell seeding efficiency in under 5 minutes.

Embodiment 68. The microfluidic system of embodiment 67, further comprising a feeding input channel, wherein the one or more bioprocessing chambers are fluidically connected to the feeding input channel.

Embodiment 69. The microfluidic system of embodiment 67, further comprising one or more collection outputs fluidically connected to the one or more bioprocessing chambers.

Embodiment 70. The microfluidic system of embodiment 69, wherein the one or more collection outputs are fluidically connected to the one or more bioprocessing chambers via a bottom surface of the one or more bioprocessing chambers.

Embodiment 71. The microfluidic system of embodiment 67, further comprising one or more filters that selectively prevent solid particles from passing from the one or more bioprocessing chambers to a feeding output channel of the microfluidic system.

Embodiment 72. A microfluidic system comprising one or more bioprocessing chambers, wherein the system is configured for homogenous cell distribution of at least 20,000 cells in the one or more bioprocessing chambers.

Embodiment 73. The microfluidic system of embodiment 72, further comprising a feeding input channel, wherein the one or more bioprocessing chambers are fluidically connected to the feeding input channel.

Embodiment 74. The microfluidic system of embodiment 72, further comprising one or more collection outputs fluidically connected to the one or more bioprocessing chambers.

Embodiment 75. The microfluidic system of embodiment 74, wherein the one or more collection outputs are fluidically connected to the one or more bioprocessing chambers via a bottom surface of the one or more bioprocessing chambers.

Embodiment 76. The microfluidic system of embodiment 72, further comprising one or more filters that selectively prevent solid particles from passing from the one or more bioprocessing chambers to a feeding output channel of the microfluidic system.

Embodiment 77. The solid support of embodiment 11, further comprising an additional feeding output channel fluidically connected to the bioprocessing chamber.

Embodiment 78. The solid support of embodiment 77, wherein the additional feeding output channel is located upstream or downstream of the feeding output channel.

Embodiment 79. The solid support of embodiment 77, wherein the additional feeding output channel is located adjacent or proximal to the feeding output channel.

Embodiment 80. The solid support of embodiment 77, wherein the additional feeding output channel is configured to close while the feeding output channel is used to receive a filtered flow from the bioprocessing chamber.

Embodiment 81. The solid support of embodiment 77, wherein the feeding output channel is configured to close while the additional feeding output channel is open to allow fluids to exit through the additional feeding output channel during perfusion.

Embodiment 82. The solid support of embodiment 11, wherein the ceiling comprises a permeable polymer membrane.

Embodiment 83. The solid support of embodiment 11, wherein the ceiling comprises one or more fillets.

Embodiment 84. The solid support of embodiment 1, wherein the bioprocessing chamber comprises one or more fillets configured to distribute pressure across a portion of the bioprocessing chamber to reduce a likelihood of fracture or deformation of the bioprocessing chamber.

Embodiment 85. The solid support of embodiment 84, wherein the one or more fillets are located on an upper perimeter portion of the bioprocessing chamber.

Embodiment 86. The solid support of embodiment 1, further comprising a plurality of feeding output channels connected to the bioprocessing chamber via a ceiling of the bioprocessing chamber.

Embodiment 87. A solid support comprising:
a bioprocessing chamber comprising a bottom surface for culturing cells and a ceiling for enclosing at least a portion of the bioprocessing chamber to form a bioprocessing region;

a collection output configured for harvesting at least one cell cultured in the bioprocessing chamber, wherein the collection output is fluidically connected to the bioprocessing chamber via the ceiling or the bottom surface of the bioprocessing chamber;

a feeding output channel fluidically connected to the bioprocessing chamber via the ceiling, wherein the feeding output channel is configured to receive a flow of a fluid from the bioprocessing chamber; and a flow path for directing the fluid along a streamline from a feeding input channel of the solid support through the bioprocessing chamber to the feeding output channel, wherein the flow path is configured to reduce or minimize (i) a turbulent flow of the fluid and (ii) a shear stress on at least one cell cultured in the bioprocessing chamber.

Embodiment 88. The solid support of embodiment 87, further comprising a filter configured to selectively prevent a passage of solid particles from the bioprocessing chamber to the feeding output channel.

Embodiment 89. The solid support of embodiment 88, wherein the filter is positioned within the feeding output channel or upstream of the feeding output channel.

Embodiment 90. The solid support of embodiment 88, wherein the filter comprises a filter membrane that comprises a pore size of less than 10 μm, less than 7.5 μm, less than 5 μm, or less than 2.5 μm.

Embodiment 91. The solid support of embodiment 87, further comprising a plurality of feeding input channels comprising the feeding input channel, wherein the plurality of feeding input channels is fluidically coupled to the bioprocessing chamber.

Embodiment 92. The solid support of embodiment 91, wherein the plurality of feeding input channels comprises or form a binary tree network.

Embodiment 93. The solid support of embodiment 87, wherein the feeding input channel is located on a first plane, and wherein the bottom surface of the bioprocessing chamber is located on a second plane that is different than the first plane.

Embodiment 94. The solid support of embodiment 93, wherein the second plane is below the first plane.

Embodiment 95. The solid support of embodiment 93, wherein the collection output is located on a third plane that is below the second plane or above the first plane.

Embodiment 96. The solid support of embodiment 87, further comprising an additional feeding output channel fluidically connected to the bioprocessing chamber.

Embodiment 97. The solid support of embodiment 96, wherein the additional feeding output channel is a collection output.

Embodiment 98. The solid support of embodiment 96, wherein the additional feeding output channel is located upstream or downstream of the feeding output channel.

Embodiment 99. The solid support of embodiment 96, wherein the additional feeding output channel is located adjacent or proximal to the main feeding output channel.

Embodiment 100. The solid support of embodiment 96, wherein the additional feeding output channel is configured to close while the feeding output channel is used to receive the flow from the bioprocessing chamber.

Embodiment 101. The solid support of embodiment 87, wherein the bioprocessing chamber comprises a rounded or curved edge or surface.

Embodiment 102. The solid support of embodiment 87, wherein the bioprocessing chamber comprises a fillet configured to distribute pressure due to fluid flow across a portion of the bioprocessing chamber.

Embodiment 103. The solid support of embodiment 102, wherein the fillet is configured to reduce or minimize a likelihood of fracture or deformation of the bioprocessing chamber due to the fluid flow.

Embodiment 104. The solid support of embodiment 102, wherein the fillet is located on an upper perimeter portion of the bioprocessing chamber.

Embodiment 105. The solid support of embodiment 87, wherein the flow path comprises a first flow path between the feeding input channel and the feeding output channel for transporting the fluid or cell medium.

Embodiment 106. The solid support of embodiment 105, wherein the flow path comprises a second flow path for harvesting the at least one cell through the collection output.

Embodiment 107. The solid support of embodiment 106, wherein the first flow path and the second flow path extend along a same direction.

Embodiment 108. The solid support of embodiment 106, wherein the first flow path and the second flow path at least partially coincide.

Embodiment 109. The solid support of embodiment 87, wherein the bioprocessing region is configured for cell seeding, media perfusion, cell washing, cell expansion, cell culturing, and cell harvesting without requiring a transport of cultured cells to different chambers or to an external chamber.

Embodiment 110. The solid support of embodiment 87, wherein the solid support is configured for i) culturing over 20,000 cells in the bioprocessing chamber and ii) harvesting at least 90% of the cells to yield recovered cells, wherein at least 90% of the recovered cells are viable.

Embodiment 111. The solid support of embodiment 87, wherein the microfluidic system is configured for: i) seeding over 20,000 cells in the bioprocessing chamber, ii) at greater than 90% cell retention efficiency, (iii) in under 5 minutes.

Embodiment 112. The solid support of embodiment 87, wherein the bioprocessing chamber is elongated and comprises a first end wall and a second end wall opposite the first end wall, and wherein the ceiling of the bioprocessing chamber is substantially orthogonal to the first end wall and the second end wall.

Embodiment 113. The solid support of embodiment 112, wherein the feeding input channel is fluidically connected to the first end wall of the bioprocessing chamber and feeding output channel is fluidically connected to the ceiling nearer the second wall end of the bioprocessing chamber than the first end wall.

Embodiment 114. The solid support of embodiment 87, wherein a length dimension of the bioprocessing chamber is at most about 60 cm, wherein a width dimension of the bioprocessing chamber is at most about 10 cm, and wherein a height dimension of the bioprocessing chamber is at most about 5 mm.

Embodiment 115. The solid support of embodiment 87, wherein the bioprocessing chamber is treated with a coating, wherein the coating interacts with or adheres to the bottom surface via curing or incubation.

Embodiment 116. The solid support of embodiment 87, wherein the cells comprise human cells.

EXAMPLES

Example 1

A sample of T-cells is taken from a cancer patient. The T-cells are modified by transduction in a chip to produce chimeric antigen receptors that target the patient's cancer. The chip (solid support comprising a bioprocessing chamber) of FIG. 1A is provided, and a cell culture medium comprising the T-cells is flowed from the feeding input channel (101) near the first end wall (1002) into the bioprocessing chamber (105). In some cases, prior to actual seeding, a priming step is performed or initiated. After seeding, the T-cells are retained in the bioprocessing chamber, in part because of the filter (104), while the cell culture medium fluid flows through an opening in the ceiling (1004) of the bioprocessing chamber (105), across the filter (104), and out feeding output channel (103) near the second end wall (1003). During the introduction of the T-cells into the bioprocessing chamber (105), the collection output (108) is filled with fluid and does not permit the cell culture medium to pass through the collection output (108). The output is primed with fluid and a valve placed in or within the tubing outside the chip can be closed such that there is no fluid flow through the output. The chip is agitated on a shaker, and the T-cells in the bioprocessing chamber are allowed to homogenously seed on the bottom surface (1001). After seeding and before proliferation, T-cells are activated by flowing an activation agent through the perfusion inlet. The reagent is left to react with the cells for a certain amount of time. The T-cells are subsequently washed with a washing reagent (e.g., PBS) via the perfusion inlet. The T-cells are subsequently transduced via a viral vector (e.g. lentivirus) via the perfusion inlet. The reagent is left to react with the cells for a certain amount of time. The T-cells are subsequently washed with a washing reagent (e.g., PBS) via the perfusion inlet. Agitation can be done at any time to re-homogenize the cells across the chip surface.

Perfusion is performed to introduce media; the perfusion does not disturb the seeded modified T-cells because they are in the recess on the bottom surface (1001). The modified T-cells are expanded on the bottom surface for 72 hours. A wash fluid is then provided through the feeding input channel (101) while suction is applied through the collection output (108) to collect the expanded modified T-cells. After the wash and before the harvest, the cells are mixed with a formulation reagent (e.g. a cryopreservant) via the perfusion inlet. The cells are then harvested via the collection output using the push and pull methods described herein. Enzymes may not or need not be required to facilitate harvesting. Agitation can be used to further increase harvesting efficiency. The collected, expanded modified T-cells are then introduced into the patient to treat the patient's cancer.

While preferred embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein can be employed in practicing the disclosure. It is therefore contemplated that the disclosure shall also cover any such alternatives, modifications, variations or equivalents. It is intended that the following claims define the scope of the invention and that methods and structures within the scope of these claims and their equivalents be covered thereby.

What is claimed is:

1. A solid support comprising:
a bioprocessing chamber comprising a first bottom surface for culturing cells and a first ceiling opposite of the first bottom surface, wherein the first bottom surface and the first ceiling are connected by one or more first sidewalls, wherein the bioprocessing chamber comprises a first height measured between the first bottom surface and the first ceiling;
a collection output fluidically connected to the bioprocessing chamber via the first ceiling or the first bottom surface of the bioprocessing chamber;
a feeding input channel configured to receive a fluid, wherein the feeding input channel is fluidically connected to the bioprocessing chamber, wherein the feeding input channel comprises a second bottom surface and a second ceiling opposite of the second bottom surface, wherein the second bottom surface and the second ceiling are connected by one or more second sidewalls, wherein the feeding input channel comprises a second height measured between the second bottom surface and the second ceiling of the feeding input channel, wherein the first bottom surface and the second bottom surface are parallel, and wherein the second height is less than the first height;
a feeding output channel fluidically connected to the bioprocessing chamber via the first ceiling; and
a filter connected to the feeding output channel or the bioprocessing chamber, wherein the filter is configured to selectively prevent a passage of the at least one cell from the bioprocessing chamber to the feeding output channel.

2. The solid support of claim 1, wherein the filter comprises a filter membrane that comprises one or more pores, and wherein the one or more pores have a diameter of less than 10 μm, less than 7.5 μm, less than 5 μm, or less than 2.5 μm.

3. The solid support of claim 1, further comprising a plurality of feeding input channels comprising the feeding input channel, wherein the plurality of feeding input channels is fluidically coupled to the bioprocessing chamber.

4. The solid support of claim 3, wherein the plurality of feeding input channels comprises or form a binary tree network.

5. The solid support of claim 1, further comprising an additional feeding output channel fluidically connected to the bioprocessing chamber.

6. The solid support of claim 1, wherein the bioprocessing chamber comprises a rounded or curved edge or surface.

7. The solid support of claim 1, wherein the bioprocessing chamber comprises a fillet comprising a curved or rounded surface, wherein the fillet is located at an interface between (i) the first ceiling and the one or more first sidewalls or (ii) the first bottom surface and the one or more first sidewalls.

8. The solid support of claim 7, wherein the fillet is located on an upper perimeter of the bioprocessing chamber.

9. The solid support of claim 1, wherein the bioprocessing chamber comprises a first end wall and a second end wall opposite the first end wall, and wherein the first ceiling, the one or more first sidewalls, and the first bottom surface of the bioprocessing chamber are orthogonal to the first end wall and the second end wall.

10. The solid support of claim 9, wherein the feeding input channel is fluidically connected to the first end wall of the bioprocessing chamber, and wherein the feeding output channel is fluidically connected to the first ceiling nearer to the second wall end of the bioprocessing chamber than the first end wall.

11. The solid support of claim 1, wherein a length dimension of the bioprocessing chamber is at most 60 cm, wherein a width dimension of the bioprocessing chamber is at most 10 cm, and wherein a height dimension of the bioprocessing chamber is at most 5 mm.

12. The solid support of claim 1, wherein the bioprocessing chamber comprises the at least one cell.

13. The solid support of claim 1, wherein the collection output is positioned below the filter.

14. The solid support of claim 9, wherein a distance between the first end wall and the second end wall is at most 60 cm.

15. The solid support of claim 1, wherein a distance between the first bottom surface and the first ceiling is at most 5 mm.

* * * * *